United States Patent
Nakatsuru et al.

(10) Patent No.: US 7,786,266 B2
(45) Date of Patent: Aug. 31, 2010

(54) METHODS FOR DAMAGING CELLS USING EFFECTOR FUNCTION OF ANTI-DSC2 ANTIBODY

(75) Inventors: Shuichi Nakatsuru, Kawasaki (JP); Takashi Iwamoto, Kawasaki (JP); Megumi Yoshikawa, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 11/912,848

(22) PCT Filed: May 11, 2006

(86) PCT No.: PCT/JP2006/309886

§ 371 (c)(1),
(2), (4) Date: Jun. 9, 2008

(87) PCT Pub. No.: WO2006/121207

PCT Pub. Date: Nov. 16, 2006

(65) Prior Publication Data

US 2008/0260748 A1    Oct. 23, 2008

Related U.S. Application Data

(60) Provisional application No. 60/680,609, filed on May 12, 2005.

(51) Int. Cl.
| | |
|---|---|
| *C07K 16/00* | (2006.01) |
| *C12P 21/08* | (2006.01) |
| *A61K 39/395* | (2006.01) |
| *C07H 21/04* | (2006.01) |

(52) U.S. Cl. ............ 530/387.1; 530/388.1; 530/388.85; 424/130.1; 424/138.1; 424/141.1; 536/23.53

(58) Field of Classification Search ....................... None
See application file for complete search history.

(56) References Cited

U.S. PATENT DOCUMENTS

2005/0215770 A1*  9/2005  Bell et al. .............. 530/388.22

FOREIGN PATENT DOCUMENTS

| WO | WO 0157226 A1 * | 8/2001 |
| WO | WO 2004066931 A2 * | 8/2004 |
| WO | WO 2004/101511 A | 11/2004 |
| WO | WO 2004101511 A2 * | 11/2004 |
| WO | WO 2005005638 A2 * | 1/2005 |

OTHER PUBLICATIONS

Campbell. Monoclonal Antibody Technology, 1984. pp. 1-32.*
Holton, J., et al., "Desmosomal glycoproteins 2 and 3 (desmocollins) show N-terminal similarity to calcium-dependent cell-cell adhesion molecules," *Journal of Cell Science*, vol. 97, No. 2, pp. 239-246 (Oct. 1990).
Lorimer, J., et al., "Cloning, sequence analysis and expression pattern of mouse desmocollin 2 (DSC2), a cadherin-like adhesion molecule," *Molecular Membrane Biology*, vol. 11, No. 4, pp. 229-236 (Oct. 1994).
Schaefer, S., et al., "Immunological identification and characterization of the desmosomalcadherin DSG2 in coupled and uncoupled epithelial cells and in human tissues," *Differentiation*, vol. 60, No. 2, pp. 99-108 (May 1996).

* cited by examiner

*Primary Examiner*—Larry R. Helms
*Assistant Examiner*—Anne M. Gussow
(74) *Attorney, Agent, or Firm*—Townsend and Townsend and Crew LLP

(57) ABSTRACT

The present invention is based on the discovery that the cytoxicity of anti-desmocollin 2 (DSC2) antibodies can be used for treating various cancers including lung, colon, pancreatic, prostate, breast, gastric or liver cancers. Specifically, the present invention provides antibodies against DSC2 that have effector function. Furthermore, the present invention provides methods and pharmaceutical compositions that comprise anti-DSC2 antibody as an active ingredient for damaging DSC2-expressing cells via the effector function of the antibody.

16 Claims, 6 Drawing Sheets

METHODS FOR DAMAGING CELLS USING EFFECTOR FUNCTION OF ANTI-DSC2 ANTIBODY

CROSS-REFERENCES TO RELATED APPLICATIONS

This application is a U.S. National Stage Application of PCT/JP2006/309886, filed May 11, 2006, which claims the benefit of U.S. Provisional Application Ser. No. 60/680,609 filed May 12, 2005, the contents of which all of which are hereby incorporated by reference in their entirety.

TECHNICAL FIELD

DSC2 has been found to be specifically expressed in various cancer cells including lung, colon, pancreatic, prostate, breast, gastric, and liver cancer cells. The present invention relates to antibodies against desmocollin 2 (DSC2) having effector function, and the use of the antibodies in methods and compositions for damaging DSC2-expressing cells via the effector function of the anti-DSC2 antibodies.

BACKGROUND ART

Lung cancer is one of the most common lethal human tumors. Non-small-cell lung cancer (NSCLC) is the most common form, accounting for nearly 80% of lung tumors (American Cancer Society, Cancer Facts and Figures 2001, Am. Chem. Soc. Atlanta, 2001). The majority of NSCLCs are not diagnosed before advanced stage, and thus the overall 10-year survival rate has stayed as low as 10%, despite recent advances in multimodality therapies (Fry et al, Cancer 86: 1867-76, 1999). Currently, chemotherapy using platinum is considered to be a fundamental therapy for NSCLCs. However, the therapeutic action of pharmaceutical agents has not progressed beyond the point of being able to prolong the survival of advanced NSCLC patients to a certain extent (Non-small Cell Lung Cancer Collaborative Group, Bmj 311: 899-909, 1995). A number of targeting therapies are being investigated, including those that use tyrosine kinase inhibitors. However, to date, promising results have been achieved only in a limited number of patients, and in some patients, therapeutic effects have accompanied severe side effects (Kris et al., Proc Am Soc Clin Oncol 21: 292a (A1166), 2002).

Colorectal carcinoma is a leading cause of cancer deaths in developed countries. Specifically, more than 130,000 new cases of colorectal cancer in USA are reported each year. Colorectal cancer represents about 15% of all cancers. Of these, approximately 5% are directly related to inherited genetic defects. In spite of recent progress in therapeutic strategies, prognosis of patients with advanced cancers remains very poor. Although molecular studies have revealed the involvement of alterations in tumor suppressor genes and/or oncogenes in carcinogenesis, the precise mechanisms still remain to be elucidated.

Pancreatic cancer has one of the highest mortality rates of any malignancy, and the 5-year-survival rate of patients is 4%. 28,000 people are diagnosed as having pancreatic cancer each year, and nearly all of these patients die of their disease (Greenlee R T et al., Cancer statistics, 2001. CA Cancer J Clin 51: 15-36, 2001). The poor prognosis of this malignancy is a result of the difficulty of early diagnosis and poor response to current therapeutic methods (Greenlee R T et al., Cancer statistics, 2001. CA Cancer J Clin 51: 15-36, 2001; Klinkenbijl J H et al., Ann Surg 230: 776-82, and discussion 782-4, 1999). In particular, currently no tumor marker is identified that allows reliable screening at an early, potentially curative stage of the disease.

Prostate cancer (PRC) is one of the most common malignancies in men and represents a significant worldwide health problem. It is the second most frequent cause of cancer death in USA (Greenlee R T et al., Cancer statistics, 2001 CA Cancer J Clin 51: 15-36, 2001). Incidence of PRC is steadily increasing in developed countries according to the prevalence of Western-style diet and increasing number of senior population. Increasing number of patients also die from this disease in Japan due to adoption of a Western life style (Kuroishi T, Epidemiology of prostate cancer. Klinika 25: 43-8, 1995). Currently, the diagnosis of PRC is based on an increased level of the serum prostate specific antigen (PSA). Early diagnosis provides an opportunity for curative surgery. Patients with organ confined PRC are usually treated and approximately 70% of them are curable with radical prostatectomy (Roberts W W et al., Urology 57: 1033-7, 2001; Roberts S G et al., Mayo Clin Proc 76: 576-81, 2001). Most of patients with advanced or relapsed disease are treated with androgen ablation therapy due to the androgen-dependent initial growth of PRC. Although most of these patients initially respond to androgen ablation therapy, the disease eventually progresses to androgen-independent PRC, at which point the tumor is no longer responsive to androgen ablation therapy.

One of the most serious clinical problems in the treatment for PRC is that this androgen-independent PRC is unresponsive to any other known therapies. Thus, clarifying the mechanism of androgen-independent growth and establishing new therapies other than androgen ablation therapy against PRC are urgent issues for the management of PRC.

Breast cancer, a genetically heterogeneous disease, is the most common malignancy in women. An estimation of approximately 800,000 new cases is reported each year worldwide (Parkin D M, et al., CA Cancer J Clin 49: 33-64, 1999). Mastectomy is the first concurrent option for the treatment of this disease. Despite surgical removal of the primary tumors, relapse at local or distant sites may occur due to micrometastasis that is undetectable at the time of diagnosis (Saphner T, et al., J Clin Oncol 14: 2738-46, 1996). Cytotoxic agents are usually administered as adjuvant therapy after surgery aiming to kill those residual or premalignant cells.

Treatment with conventional chemotherapeutic agents is often empirical and is mostly based on histological tumor parameters, and in the absence of specific mechanistic understanding. Target-directed drugs are therefore becoming the bedrock treatment for breast cancer. Tamoxifen and aromatase inhibitors, two representatives of its kind, have been proved to achieve great responses when used as adjuvant or chemoprevention in patients with metastasized breast cancer (Fisher B et al. J Natl Cancer Inst 90: 1371-88, 1998; Cuzick J, Lancet 360: 817-24, 2002). However, the drawback is that only patients who express estrogen receptors are sensitive to these drugs. Further, regarding their side effects, long term tamoxifen treatment may cause endometrial cancer as well as deleterious effect of bone fracture in the postmenopausal women in aromatase prescribed patients (Coleman R E Oncology 18(5 Suppl 3): 16-20, 2004). Owing to the emergence of side effects and drug resistance, it is obviously necessarily to search novel molecular targets for selective smart drugs on the basis of characterized mechanisms of action.

Gastric cancer is a leading cause of cancer death in the world, particularly in the Far East, with approximately 700,000 new cases diagnosed worldwide annually. Surgery is the mainstay in terms of treatment, because chemotherapy remains unsatisfactory. Gastric cancers at an early stage can be cured by surgical resection, but prognosis of advanced gastric cancers remains very poor.

Hepatocellular carcinoma (HCC) is one of the most common cancers worldwide and its incidence is gradually increasing in Japan as well as USA (Akriviadis E A et al., Br J Surg 85(10): 1319-31, 1998.). Although recent medical advances have made great progress in diagnosis, a large number of patients with HCCs are still diagnosed at advanced stages and their complete cures from the disease remain difficult. In addition, since patients with hepatic cirrhosis or chronic hepatitis have a high risk to HCCs, they may develop multiple liver tumors, or new tumors even after complete removal of initial tumors. Therefore, development of highly effective chemotherapeutic drugs and preventive strategies are matters of pressing concern.

Research aiming at the elucidation of carcinogenic mechanisms has revealed a number of candidate target molecules for anti-tumor agents. For example, the farnesyltransferase inhibitor (FTI) is effective in the therapy of Ras-dependent tumors in animal models (Sun J. et al., Oncogene.; 16:1467-73, 1998.). This pharmaceutical agent was developed to inhibit growth signal pathways related to Ras, which is dependant on post-transcriptional farnesylation. Human clinical trials where anti-tumor agents were applied in combination with the anti-HER2 monoclonal antibody trastuzumab with the aim of antagonizing the proto-oncogene HER2/neu have succeeded in improving clinical response, and improved the overall survival rate of breast cancer patients.

Tyrosine kinase inhibitor STI-571 is an inhibitor which selectively deactivates bcr-abl fusion protein. This pharmaceutical agent was developed for the therapy of chronic myeloid leukemia, where the constant activation of bcr-abl tyrosine kinase has a significant role in the transformation of white blood cells. Such pharmaceutical agents are designed to inhibit the carcinogenic activity of specific gene products (O'Dwyer M E & Druker B J. Curr Opin Oncol.; 12:594-7, 2000.). Today, gene products with promoted expression in cancer cells are usually potential targets for the development of novel anti-tumor agents.

Another strategy for cancer therapy is the use of antibodies which bind to cancer cells. The following are representative mechanisms of antibody-mediated cancer therapy:

(I) Missile therapy: in this approach, a pharmaceutical agent is bound to an antibody that specifically binds to cancer cells, and the agent then specifically acts on the cancer cells. Through this method the pharmaceutical agent intensively acts on the cancer cells, therefore, even agents with strong side effects can be used with less side effects. In addition to pharmaceutical agents, there are also reports of approaches where precursors of pharmaceutical agents, enzymes which metabolize the precursors to an active form, and so on are bound to the antibodies;

(II) The use of antibodies which target functional molecules: this approach inhibits the binding between growth factors and cancer cells using, for example, antibodies that bind to growth factor receptors or growth factors. Some cancer cells proliferate depending on the activity of growth factors. For example, cancers dependent on epithelial growth factor (EGF) or vascular endothelial growth factor (VEGF) are known. For such cancers, inhibiting the binding between a growth factor and the cancer cells can be expected to have a therapeutic effect; and (III) Antibody cytotoxicity: antibodies that bind to some kinds of antigens on cancer cells can exert cytotoxicity to the cancer cells. These types of antibodies have itself a direct anti-tumor effect. Antibodies that display cytotoxicity to cancer cells are gaining attention as antibody agents expected to be highly effective against tumors.

The object and features of the present invention will become more fully apparent when the following disclosure of the invention is read in conjunction with the accompanying figures and examples. However, it is to be understood that the following disclosure is of preferred embodiments, and not restrictive of the invention or other alternate embodiments of the invention.

DISCLOSURE OF THE INVENTION

Definitions

The words "a", "an", and "the" used herein mean "at least one" unless otherwise specifically indicated.

The terms "isolated" and "purified" used in relation with a substance (e.g., polypeptide, antibody, polynucleotide, etc.) indicates that the substance is substantially free from at least one substance that may else be included in the natural source. Thus, an isolated or purified antibody refers to antibodies that is substantially free of cellular material such as carbohydrate, lipid, or other contaminating proteins from the cell or tissue source from which the protein (antibody) is derived, or substantially free of chemical precursors or other chemicals when chemically synthesized. The term "substantially free of cellular material" includes preparations of a polypeptide in which the polypeptide is separated from cellular components of the cells from which it is isolated or recombinantly produced. Thus, a polypeptide that is substantially free of cellular material includes preparations of polypeptide having less than about 30%, 20%, 10%, or 5% (by dry weight) of heterologous protein (also referred to herein as a "contaminating protein"). When the polypeptide is recombinantly produced, it is also preferably substantially free of culture medium, which includes preparations of polypeptide with culture medium less than about 20%, 10%, or 5% of the volume of the protein preparation. When the polypeptide is produced by chemical synthesis, it is preferably substantially free of chemical precursors or other chemicals, which includes preparations of polypeptide with chemical precursors or other chemicals involved in the synthesis of the protein less than about 30%, 20%, 10%, 5% (by dry weight) of the volume of the protein preparation. That a particular protein preparation contains an isolated or purified polypeptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, antibodies of the present invention are isolated or purified.

An "isolated" or "purified" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the present invention are isolated or purified.

The terms "polypeptide", "peptide", and "protein" are used interchangeably herein to refer to a polymer of amino acid residues including antibodies. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" refers to naturally occurring and synthetic amino acids, as well as amino acid analogs and amino acid mimetics that similarly functions to the naturally occurring amino acids. Naturally occurring amino acids are those encoded by the genetic code, as well as those modified after translation in cells (e.g., hydroxyproline, γ-carboxyglutamate, and O-phosphoserine). The phrase "amino acid analog" refers to compounds that have the same basic chemical structure (an α carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides", "nucleic acids", and "nucleic acid molecules" are used interchangeably unless otherwise specifically indicated and are similarly to the amino acids referred to by their commonly accepted single-letter codes.

The term "antigen" refers to proteins that have the binding ability to a corresponding antibody and induce the antigen-antibody reaction in vivo. On the other hand, the term "immunogen" refers to the group of proteins among the antigens that further have the ability to induce the production of antibody in vivo.

"Antibodies" and "immunoglobulins" are glycoproteins having the same structural characteristics. While antibodies exhibit binding specificity to a specific antigen, immunoglobulins include both antibodies and other antibody-like molecules, for which antigen specificity has not been defined. Polypeptides of the latter kind are, for example, produced at low levels by the lymph system and at increased levels by myelomas.

Herein, the term "antibody" refers to molecules belonging to any class or subclass of immunoglobulins. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" herein includes both monoclonal and polyclonal antibodies. The term also includes modified antibodies that retain the specific antigen-binding ability of the original antibody, for example, antibodies bound to other molecules, chimeric antibodies (humanized antibodies etc.), antibodies wherein one or more amino acids therein are substituted, deleted, added, or inserted, and the like. Furthermore, the term is intended to encompass fragments of antibodies so long as they retain their specific binding ability to its antigen. Such fragments include, for example, Fv, Fab, $F(ab')_2$, scFv, etc., however, the present invention is not restricted thereto and includes much smaller portions of the antibody that still possess the specific binding ability of the original antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they can be synthesized by hybridoma culture, uncontaminated by other immunoglobulins. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler and Milstein, (Nature 256: 495-7, 1975), or can be made by recombinant DNA methods (Cabilly et al., Proc Natl Acad Sci USA 81:3273-7, 1984).

The monoclonal antibodies herein specifically include "chimeric" antibodies or immunoglobulins, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., Proc Natl Acad Sci USA 81:3273-7, 1984; Morrison et al., Proc Natl Acad Sci USA 81:6851-5, 1984). Most typically, chimeric antibodies or immunoglobulins comprise human and murine antibody fragments, generally human constant and mouse variable regions.

The "effector function" refers to the cytotoxicity of an antibody. The cytotoxicity is usually involved with the Fc region of the antibody, however, the present invention is not restricted thereto and "antibodies with effector function" encompasses all kinds of antibodies that cause damage to cells on which the antigen of the antibodies are expressed.

Specifically, antibody-dependent cell-mediated cytotoxicity (ADCC; also referred to as antibody-dependent cellular cytotoxicity), complement-dependent cytotoxicity (CDC), and neutralizing activity are known as antibody effector functions, and are detailed below. These biological activities of the antibody can independently damage cells, however, in practice, they function in composite in living cells. Thus, an antibody of the invention may have one, two or all of these effector functions. Preferable effector functions herein are either, ADCC, CDC, or both.

(1) Antibody Dependent Cell-mediated Cytotoxicity (ADCC)

Antibody dependent cell-mediated cytotoxicity (ADCC) refers to a cell damaging reaction which is caused on a target cell via the action of effector cell and antibody, in particular IgG class antibodies. Hence the amount of antibody required for causing this effect is quite small, this cytotoxic function is considered to be important where only weak antibody production reaction is caused, like in tumors, autoimmune diseases, etc. It is known that ADCC is an important mechanism in cancer therapies using antibodies (Clynes R A, et al., Nature Med 6: 443-6, 2000). For example, ADCC is reported to be an important effector mechanism for the treatment of cancer using anti-CD20 chimeric antibody (Cartron G, et al., Blood 99: 754-8, 2002). Thus, when applying the present invention for cancer therapies, the effector function of ADCC becomes particularly important.

Cells involved in this reaction are called effector cells and acquire cytotoxicity by binding to the antigen bound antibodies. Example of such cells includes lymphocytes (T cells, NK cells, etc.), macrophages, polymorphonuclear leukocyte (neutophils), K cell, and the like. These cells carry receptors, called Fc receptors that bind to the Fc region of antibodies bound on the cell surface through an antigen. It is known that each of the Fc receptors specifically recognize and bind to the Fc region of a specific class and/or subclass of the immunoglobulins. For example, cells comprising Fc receptors specific to the Fc region of the immunoglobulin class IgG include T cells, NK cells, neutrophils, and macrophages, and are activated by the Fc region of IgG class antibodies to exert cytotoxicity against cells to which these antibodies have bound.

ADCC can be classified based on the involved effector cell to IgG-dependent macrophage-mediated cytotoxicity (ADMC) and IgG-dependent NK-cell-mediated cytotoxicity (narrow sense ADCC). Herein, the term ADCC is used in the broad sense and encompasses ADMC, where macrophages function as the effector cell.

Antibody ADCC is known to be an important mechanism of anti-tumor effects caused in a living body, particularly important in cancer therapies that use antibodies (Clynes R A, et al., Nature Med 6: 443-6, 2000). For example, a close relationship between the therapeutic effect of anti-CD20 antibody chimeric antibodies and ADCC has been reported (Cartron G, et al., Blood 99: 754-8, 2002). Thus, ADCC is particularly important among the antibody effector functions in the present invention.

At present, the mechanism of ADCC is roughly explained as follows: first, an antibody binds to the target cell, then an effector cell recognizing the Fc region of the antibody, binds to the antibody. The effector cell, which is bridged to the target cell via the antibody bound to the cell surface, is thought to induce target cell apoptosis by transmitting some sort of lethal signal to the target cell.

(2) Complement-Dependent Cytotoxicity (CDC)

The Fc region of antibodies of an antibody-antigen complex is known to activate the complement system. The complements involved in this system are sequentially activated through enzymatic reaction or binding with other activated complements and form molecules that show biological activities, such as induction of histamine release, acting as chemotactic factors for neutrophils and macrophages, opsonin activity, etc. Among these activated molecules, C5b-9 membrane attack complex (MAC) damage viral particles and cell membranes independent of effector cells. MAC exerts a strong binding affinity for cell membranes, and the molecule bound on a cell membrane opens a hole, making it easy for water to flow in and out of the cell. As a result, the cell membrane gets destabilized, or the cell is destroyed through the change in osmotic pressure. The biological activity caused by an activated complement or complex of the complements only extends to a region close to the antigen-antibody complex which activated the complement system. In particular, the function of lysing cells to which the antibody variable region has been bound is defined as CDC.

Further, the pathway to activate the complement system has been revealed to differ depending on the immunoglobulin class of the antibody inducing the pathway. For example, among the human antibodies, IgM and IgG activate the classical pathway. On the other hand, IgA, IgD, and IgE do not activate this pathway.

(3) Neutralizing Activity

Some antibodies are known to have the function of depriving infectivity of pathogens and/or activity of toxins. Such neutralization of pathogens and toxins can be achieved through the binding of the antigenic variable region of an antibody to an antigen included in the pathogens or toxin. Sometimes, the neutralization is known to require not only the antibody but complement mediation to deprive a virus of its infectivity. Thus, in case of using an antibody with neutralizing activity which requires complement mediation in therapy and such, the Fc region, essential for activating the complement system, is necessary in addition to the antigenic variable region.

Unless otherwise defined, all technical and scientific terms used herein have the same meaning as commonly understood by one of ordinary skill in the art to which this invention belongs. In case of conflict, the present specification, including definitions, will control.

DETAILED DESCRIPTION OF THE INVENTION

Conditions required for destroying cancer cells using effector function of an antibody are, for example, as follows:
(a) expression of large numbers of antigenic molecules on the membrane surface of target cancer cells;
(b) uniform distribution of antigens within target cancerous tissues; and
(c) lingering of antigens bound to antibodies on the cell surface for a long time.

More specifically, for example, antigens recognized by antibodies are required to be expressed on the surface of the cell membrane of target cancer cell. In addition, it is preferable that the ratio of antigen-positive cells is as high as possible in cells forming cancerous tissues. For example, an ideal situation may be where all target cancer cells in the objective tissue are positive to that antigen. When an antigen existing only in a portion of a cancer cell population of the objective tissue is used as the target, no clinical therapeutic effect may be expected for antibodies against that antigen. Usually, the higher the expression of the antigen used as the target on the cell surface, the stronger the effector functions to be expected.

Furthermore, it is also important that antibodies bound to antigens on the cell surface are not taken up into cells. Some receptors are taken up into cells (endocytosis) after binding to a ligand, which phenomenon is called internalization. Similarly, internalization may also occur for antibodies bound to cell surface antigens. When internalization occurs, the Fc region responsible for most effector functions caused by the antibody is also taken up into the cell, which as a result inhibits the binding to the Fc region of effector cells or complements that are outside the antigen-expressing cells, and finally the antibody effector function. Therefore, when selecting an antibody with effector function, it is important to choose antigens that cause less antibody internalization.

Further, to treat cancer by using antibodies, it is also important to select antigens which expression level is low in normal organs to avoid side effects.

Thus, the present inventors identified a number of genes with specifically enhanced expression in the cancer cells but showing low expression levels in normal cells through gene expression analysis with cDNA microarrays of lung cancer cells and normal cells collected from lung cancer patients. Among these genes, those showing low expression levels in major organs were selected as candidate target genes for lung cancer therapy.

The candidate target genes included the desmocollin 2 (DSC2) gene. The amino acid sequence coded by the DSC2 gene is expected to comprise a signal peptide at its N-terminus, and thus was expected to be a protein expressed on the surface of the cytoplasmic membrane. Through a forced expression system, localized expression of c-myc-His-tagged DSC2 on the cytoplasmic membrane was confirmed via Immuno-fluorescence microscopy, and DSC2 was thought to be a transmembrane protein. Thus, the present inventors expected that DSC2 serves as a useful clinical marker and therapeutic target for lung cancer.

Specifically, antibodies against proteins encoded by these candidate target genes were examined for their ability of effector function to induce potent cytotoxicity and to finally damage lung cancer cells. As a result, anti-DSC2 antibodies could be confirmed to have effector function against DSC2-expressing cells. Furthermore, these antibodies were confirmed to cause similar effects on other cancer cell lines, such as colon, pancreatic, prostate, breast, gastric, and liver cancer cell lines wherein DSC2 was over-expressed. According to these discoveries, the inventors contemplated that antibodies against DSC2 can be used for cancer therapy with little danger of side effects.

I-1. Polypeptides

According to an aspect of the present invention, polypeptides having any of the following amino acid sequences are provided:

```
FSSFGMH,                    (SEQ ID NO: 26)
YISSGSSTIYYADTVK,           (SEQ ID NO: 27)
VHYYYFDY,                   (SEQ ID NO: 28)
KASQDINKYIA,                (SEQ ID NO: 29)
YTSTLQP,                    (SEQ ID NO: 30)
LQYDNLW,                    (SEQ ID NO: 31)
DYSMH,                      (SEQ ID NO: 32)
WINTETGEPTYADDFKG,          (SEQ ID NO: 33)
WLLFDY,                     (SEQ ID NO: 34)
KSSQSLLNSSNQKNYLA,          (SEQ ID NO: 35)
FASTRES,                    (SEQ ID NO: 36)
QQHYSTPL,                   (SEQ ID NO: 37)
GNYWS,                      (SEQ ID NO: 39)
EINHSGNTKYNPSLKS,           (SEQ ID NO: 40)
VPFDWFHPPGEPPFYYYYGMDV,     (SEQ ID NO: 41)
TGSSSNIGAGYDVH,             (SEQ ID NO: 44)
GNSNRPS,                    (SEQ ID NO: 45)
QSYDSSLSGWV,                (SEQ ID NO: 46)
GYFWS,                      (SEQ ID NO: 49)
EINHSGSTSYNPSLKS,           (SEQ ID NO: 50)
GQGYYSSLDP,                 (SEQ ID NO: 51)
SGSSSNIGSNTVN,              (SEQ ID NO: 53)
SNNQRPS,                    (SEQ ID NO: 54)
and
AAWDDSLNGVV.                (SEQ ID NO: 55)
```

Each of the above-mentioned amino acid sequences are the sequence determined for the complementarity determining regions (CDR) of mouse antibodies which regions were used for constructing chimeric antibodies or human antibodies that were confirmed to be effective to damage cells expressing DSC2. It is known that a CDR region alone even weak can recognize and specifically bind to its antigen. Further, it is generally known that the role of CDR3 among the three CDRs is particularly high in the binding of the antibody to its antigen. Thus, in some cases, the above-mentioned polypeptides of the present invention may be used alone in the diagnosis or treatment of diseases wherein the expression of DSC2 is involved.

CDR graft technology is known in the art ("Immunoglobulin genes", Academic Press (London), pp 260-74, 1989; Michael A et al., Proc Natl Acad Sci USA 91: 969-73, 1994). According to this technology, the CDRs of an antibody are replaced with the CDRs of another antibody. Through such replacement, the binding specificity of the former antibody is changed to that of the latter antibody. Among such chimeric antibodies, those whose framework amino acids are derived from a human antibody are called humanized antibodies, and are expected to cause less side effects when used in cancer therapy for human. Thus, the present polypeptide consisting of any of the aforementioned CDR amino acid sequences can also be used for preparing such chimeric antibody.

When the present polypeptide is used for preparing a chimeric antibody, it is preferable to use them in combination as follows:

```
group 1-1:
FSSFGMH (SEQ ID NO: 26) as VH CDR1,

YISSGSSTIYYADTVK (SEQ ID NO: 27) as VH CDR2,
and

VHYYYFDY (SEQ ID NO: 28) as VH CDR3;

group 1-2:
KASQDINKYIA (SEQ ID NO: 29) as VL CDR1,

YTSTLQP (SEQ ID NO: 30) as VL CDR2,
and

LQYDNLW (SEQ ID NO: 31) as VL CDR3;

group 2-1:
DYSMH (SEQ ID NO: 32) as VH CDR1,

WINTETGEPTYADDFKG (SEQ ID NO: 33) as VH CDR2,
and

WLLFDY (SEQ ID NO: 34) as VH CDR3;

group 2-2:
KSSQSLLNSSNQKNYLA (SEQ ID NO: 35) as VL CDR1,

FASTRES (SEQ ID NO: 36) as VL CDR2,
and

QQHYSTPL (SEQ ID NO: 37) as VL CDR3;

group 3-1:
GNYWS (SEQ ID NO: 39) as VH CDR1,

EINHSGNTKYNPSLKS (SEQ ID NO: 40) as VH CDR2,
and

VPFDWFHPPGEPPFYYYYGMDV (SEQ ID NO: 41) as VH CDR3;

group 3-2:
TGSSSNIGAGYDVH (SEQ ID NO: 44) as VL CDR1,
```

-continued
GNSNIRPS (SEQ ID NO: 45) as VL CDR2,
and

QSYDSSLSGWV (SEQ ID NO: 46) as VL CDR3;

group 4-1:
GYFWS (SEQ ID NO: 49) as VH CDR1,

EINHSGSTSYNPSLKS (SEQ ID NO: 50) as VH CDR2,
and

GQGYYSSLDP (SEQ ID NO: 51) as VII CDR3;
and group 4-2:
SGSSSNIGSNTVN (SEQ ID NO: 53) as VL CDR1, SNNQRPS (SEQ ID NO: 54) as VL CDR2,
and AAWDDSLNGVV (SEQ ID NO: 55) as VL CDR3.

Polypeptides which comprise the amino acid sequence in a combination as above, wherein the CDR1, CDR2, and CDR3 are separated by framework amino acid sequences are also encompassed by the present polypeptide. Furthermore, the present polypeptides may comprise both the VH and VL regions. Namely, a polypeptide of the present invention may comprise all the amino acid sequences of pairs of aforementioned groups 1-1 and 1-2, groups 2-1 and 2-2, groups 3-1 and 3-2, or groups 4-1 and 4-2 separated by appropriate amino acid sequences (e.g., framework amino acid sequence, etc.) to retain the specific binding ability of the original antibodies.

According to another aspect, the present invention provides polypeptides having any of the amino acid sequences selected from the group of:

(SEQ ID NO: 20)
MDSRLNLVFLVLILKGVQCDVQLVESGGGLVQPGGSRKLSCAASGFTFSS

FGMHWVRQAPEKGLEWVAYISSGSSTIYYADTVKGRFTISRDNPKNTLFL

QMTSLRSEDTAMYYCARVHYYYFDYWGQGTTLTVSS, (SEQ ID NO: 21)
MRPSIQFLGLLLFWLHGAQCDIQMTQSPSSLSASLGGKVTITCKASQDIN

KYIAWYQHKPGKGPRLLIHYTSTLQPGIPSRFSGSGSGRDYSFSISNLEP

EDIATYYCLQYDNLWTFGGGTKL, (SEQ ID NO: 22)
MAWVWTLLFLMAAAQSIQAQIQLVQSGPELKKPGETVKISCKASGYTFTD

YSMHWVKQAPGKGLKWMGWINTETGEPTYADDFKGRFAFSLETSASTAYL

QINNLKNEDTATYFCARWLLFDYWGQGTTLTVSS, (SEQ ID NO: 23)
MESQTQVLMFLLLWVSGACADIVMTQSPSSLAMSVGQKVTMSCKSSQSLL

NSSNQKNYLAWYQQKPGQSPKLLVYFASTRESGVPDRFIGSGSGTDFTLT

ISSVQAEDLADYFCQQHYSTPLTFGAGTKL, (SEQ ID NO: 16)
QVQLQQWGAGLLKPSETLSLTCAVYGGSFSGNYWSWIRQPPGKGLEWIGE

INHSGNTKYNPSLKSRVAISADTSKNQFSLRLSSVTAADTAVYYCARVPF

DWFHPPGEPPFYYYYGMDVWGQGTTVTVSS, (SEQ ID NO: 17)
HVILTQPPSVSGAPGQRVTISCTGSSSNIGAGYDVHWYQQLPGTAPKLLI

YGNSNRPSGVPDRFSGSKSGTSASLAITGLQAEDEADYYCQSYDSSLSGW

VFGGGTKLTVPG, (SEQ ID NO: 18)
QVQLQQWGAGLLKPSETLSLTCAVYGGSFSGYFWSWIRQAPGKGLEWIGE

INHSGSTSYNPSLKSRVTMTIDTSRKQFSLKLSSVTAADAAVYYCARGQG

YYSSLDPWGQGTLVTVSS
and (SEQ ID NO: 19)
SYELTQPPSASGTPGQRVTISCSGSSSNIGSNTVNWYQQLPGTAPKLLIY

SNNQRPSGVPDRFSGSKSGTSASLAISGLQSEDEADYYCAAWDDSLNGVV

FGGGTKLTVLG.

Each of the above-mentioned amino acid sequences are the sequence determined for the variable regions of either the light chain or the heavy chain of mouse or human antibodies that were confirmed to be effective to damage cells expressing DSC2.

Various chimeric antibodies are known in the art. For example, the Fc region of an antibody may be linked with arbitrary variable regions. The Fc region of IgA, IgE, or IgG class antibody is essential for generating ADCC. Similarly, the Fc region of IgM or IgG class antibody is required for generating CDC. Therefore, for utilization in cancer therapy on human, the antibody preferably has the Fc region of a human antibody to achieve the generation of ADCC and/or CDC. Thus, a polypeptide consisting of any of the aforementioned VH and VL amino acid sequences can be used for preparing such chimeric antibody wherein the Fc region of a human antibody is linked to the variable region that had been confirmed to be effective to damage cells expressing DSC2 by the present inventors. Since the IgG1 class antibodies triggers both ADCC and CDC, the Fc region of an IgG1 class antibody is preferable for the present invention. Much preferred may be the Fc region of a human IgG1 antibody.

Generally, it is known that modifications of one or more amino acid in a protein do not influence the function of the protein. One of skill in the art will recognize that individual additions, deletions, insertions, or substitutions to an amino acid sequence which alters a single amino acid or a small percentage of amino acids is a "conservative modification" wherein the alteration of a protein results in a protein with similar functions. Conservative substitution tables providing functionally similar amino acids are well known in the art. For example, the following eight groups each contain amino acids that are conservative substitutions for one another:

1) Alanine (A), Glycine (G);
2) Aspartic acid (d), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cystein (C), Methionine (M) (see, e.g., Creighton, Proteins, 1984).

Such conservatively modified polypeptides are included in the present polypeptides. However, proteins applicable for the method are not restricted thereto and may include non-conservative modifications so long as they retain the specific binding ability to DSC2.

In addition to the above-mentioned modification, the present polypeptides may be further linked to other substances so long as they retain their specific binding ability. Usable such other substances include: peptides, lipids, sugar and sugar chains, acetyl groups, natural and synthetic polymers, etc. These kinds of modifications may be performed to confer additional functions or to stabilize the polypeptides.

The present polypeptides may be obtained from nature as naturally occurring polypeptides via conventional purification methods, however, for smaller molecules, it is preferred to obtain them through chemical synthesis based on the selected amino acid sequence. For example, conventional peptide synthesis methods that can be adopted for the synthesis includes:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the polypeptides may be obtained adopting any known genetic engineering methods for producing polypeptides (e.g., Morrison J, J. Bacteriology 132: 349-51, 1977; Clark-Curtiss & Curtiss, Methods in Enzymology (eds. Wu et al.) 101: 347-62, 1983). For example, first, a suitable vector comprising a polynucleotide encoding the objective protein in an expressible form (e.g., downstream of a regulatory sequence comprising a promoter) is prepared, transformed into a suitable host cell, and then the host cell is cultured to produce the protein. The protein may also be produced in vitro adopting an in vitro translation system.

I-2. Antibodies

As an aspect of the present invention, a polypeptide of the invention may be an antibody. The antibody of the present invention may belong to any class or subclass of immunoglobulins. Since the IgG1 class antibodies triggers both ADCC and CDC, and non-specific binding of this class of antibody is considered to be lowest among the immunoglobulin classes and subclasses, an IgG1 class antibody is particularly preferable for the present invention.

Further, when the antibodies are used for therapy for animals, it is preferred to select an antibody derived from the same species or at least, those having the Fc region or the constant region of an antibody from the same species. Namely, when used for treating humans, it is preferred to use human antibodies or humanized antibodies.

Further, the present invention includes monoclonal and polyclonal antibodies, modified antibodies such as chimeric antibodies (humanized antibodies, scFv, etc.) that retain the specific antigen-binding ability of the original antibody, and antibody fragments (e.g., Fv, Fab, F(ab')$_2$, etc.) so long as they retain their specific binding ability to its antigen. However, the present invention is not restricted to any of the aforementioned antibodies.

As an embodiment, the present antibody includes the following sequences as the CDRs:

```
group 1:
FSSFGMH (SEQ ID NO: 26) as VH CDR1,

YISSGSSTIYYADTVK (SEQ ID NO: 27) as VH CDR2,
and

VHYYYFDY (SEQ ID NO: 28) as VH CDR3,

KASQDINKYIA (SEQ ID NO: 29) as VL CDR1,

YTSTLQP (SEQ ID NO: 30) as VL CDR2,
and
LQYDNLW (SEQ ID NO: 31) as VL CDR3;

group 2:
DYSMH (SEQ ID NO: 32) as VH CDR1,

WINTETGEPTYADDFKG (SEQ ID NO: 33) as VH CDR2,

WLLFDY (SEQ ID NO: 34) as VH CDR3;

KSSQSLLNSSNQKNYLA (SEQ ID NO: 35) as VL CDR1,

FASTRES (SEQ ID NO: 36) as VL CDR2,
and

QQHYSTPL (SEQ ID NO: 37) as VL CDR3;

group 3:
GNYWS (SEQ ID NO: 39) as VH CDR1,

EINHSGNTKYNPSLKS (SEQ ID NO: 40) as VH CDR2,

VPFDWFHPPGEPPFYYYYGMDV (SEQ ID NO: 41) as VH CDR3,

TGSSSNIGAGYDVH (SEQ ID NO: 44) as VL CDR1,

GNSNRPS (SEQ ID NO: 45) as VL CDR2,
and

QSYDSSLSGWV (SEQ ID NO: 46) as VL CDR3;
or group 4:
GYFWS (SEQ ID NO: 49) as VH CDR1, EINHSGSTSYNPSLKS (SEQ ID NO: 50) as VH CDR2, GQGYYSSLDP (SEQ ID NO: 51) as VH CDR3, SGSSSNIGSNTVN (SEQ ID NO: 53) as VL CDR1, SNNQRPS (SEQ ID NO: 54) as VL CDR2,
and AAWDDSLNGVV (SEQ ID NO: 55) as VL CDR3.
```

Preferably, the CDR1, CDR2, and CDR3 sequences therein are separated by appropriate framework amino acid sequences. More preferably, the antibody of the present invention has the VH and VL sequences selected from the group of:

```
                                              (SEQ ID NO: 20)
MDSRLNLVFLVLILKGVQCDVQLVESGGGLVQPGGSRKLSCAASGFTFSS

FGMHWVRQAPEKGLEWVAYISSGSSTIYYADTVKGRFTISRDKPKNTLFL

QMTSLRSEDTAMYYCARVHYYYFDYWGQGTTLTVSS
and (SEQ ID NO: 21)
MRPSIQFLGLLLFWLHGAQCDIQMTQSPSSLSASLGGKVTITCKASQDIN

KYIAWYQHKPGKGPRLLIHYTSTLQPGIPSRFSGSGSGRDYSFSISNLEP

EDIATYYCLQYDNLWTFGGGTKL;
```

-continued (SEQ ID NO: 22)
MAWVWTLLFLMAAAQSIQAQIQLVQSGPELKKPGETVKISCKASGYTFTD

YSMHWVKQAPGKGLKWMGWINTETGEPTYADDFKGRFAFSLETSASTAYL

QINNLKNEDTATYFCARWLLFDYWGQGTTLTVSS
and (SEQ ID NO: 23)
MESQTQVLMFLLLWVSGACADIVMTQSPSSLAMSVGQKVTMSCKSSQSLL

NSSNQKNYLAWYQQKPGQSPKLLVYFASTRESGVPDRFIGSGSGTDFTLT

ISSVQAEDLADYFCQQHYSTPLTFGAGTKL;

(SEQ ID NO: 16)
QVQLQQWGAGLLKPSETLSLTCAVYGGSFSGNYWSWIRQPPGKGLEWIGE

INHSGNTKYNPSLKSRVAISADTSKNQFSLKLSSVTAADTAVYYCARVPF

DWFHPPGEPPFYYYYGMDVWGQGTTVTVSS
and (SEQ ID NO: 17)
HVILTQPPSVSGAPGQRVTISCTGSSSNIGAGYDVHWYQQLPGTAPKLLI

YGNSNRPSGVPDRFSGSKSGTSASLAITGLQAEDEADYYCQSYDSSLSGW

VFGGGTKLTVPG;
or (SEQ ID NO: 18)
QVQLQQWGAGLLKPSETLSLTCAVYGGSFSGYFWSWIRQAPGKGLEWIGE

INHSGSTSYNPSLKSRVTMTIDTSRKQFSLKLSSVTAADAAVYYCARGQG

YYSSLDPWGQGTLVTVSS
and (SEQ ID NO: 19)
SYELTQPPSASGTPGQRVTISCSGSSSNIGSNTVNWYQQLPGTAPKLLIY

SNNQRPSGVPDRFSGSKSGTSASLAISGLQSEDEADYYCAAWDDSLNGVV

FGGGTKLTVLG.

Such preferred examples of antibodies may be, for example, 48-5, s10-4, ch48-5, chs10-4, 332, and 545, all of which were prepared in the Example; but the present invention is not restricted thereto.

It is particularly preferred that the antibody of the present invention generates effector function. Thus, the present invention further relates to antibodies against DSC2 that show at least one effector function. Suitable antibodies of the invention show effector function such as ADCC, CDC, or both. Antibodies comprising the Fc region of IgA, IgE, or IgG are essential for expressing ADCC. Equally, the antibody Fc region of IgM or IgG is preferable for expressing CDC. However, the antibodies of the present invention are not limited so long as they drive a desired effector function.

Variants, analogs or derivatives of the Fc portion may be constructed by, for example, making various substitutions of residues or sequences, and may be used for the present antibody. Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include, for example, fusion proteins and proteins including amino acid tags or labels. For example, the Fc molecule may optionally contain an N-terminal Met, especially when the molecule is to be expressed recombinantly in a bacterial cell such as E. coli.

In Fc deletion variants, one or more amino acid residues are removed in the Fc. Deletions can be included at one or both termini of the Fc polypeptide, or with removal of one or more residues within the Fc amino acid sequence. Deletion variants, therefore, include all kind of fragments of an Fc polypeptide sequence.

In Fc substitution variants, one or more amino acid residues of an Fc polypeptide are removed and replaced with alternative residues. In one aspect, the substitutions are conservative in nature, however, the invention embraces substitutions that are non-conservative.

Preferably, the parent polypeptide Fc region used in the present antibody having effector function is a human Fc region, e.g., native human Fc region like those from human IgG$_1$ (A and non-A allotypes) or human IgG$_3$. In one embodiment, the variant with improved ADCC mediates ADCC substantially more effectively than an antibody with a native sequence IgG$_1$ or IgG$_3$ Fc region and the antigen-binding region of the variant. Preferably, the variant comprises, or consists essentially of, substitutions of two or three of the residues at positions 298, 333 and 334 of the Fc region. The numbering of the residues in an immunoglobulin heavy chain is that of the EU index as in Kabat et al., (Sequences of Proteins of Immunological Interest, Fifth Edition, National Institute of Health, Bethesda, Md., 1991), expressly incorporated herein by reference. Most preferably, residues at positions 298, 333 and 334 are substituted, (e.g., with alanine residues). Moreover, in order to generate the Fc region variant with improved ADCC activity, one will generally engineer an Fc region variant with improved binding affinity for FcγRIII, which is thought to be an important FcR for mediating ADCC. For example, one may introduce an amino acid modification (e.g., an insertion, a deletion, or a substitution) into the parent Fc region at any one or more of amino acid positions 256, 290, 298, 312, 326, 330, 333, 334, 360, 378 or 430 to generate such a variant. The variant with improved binding affinity for FcγRIII may further have reduced binding affinity for FcγRII, especially reduced affinity for the inhibiting FcγRIIB receptor.

In any event, any variant amino acid insertions, deletions and/or substitutions (e.g., from 1-50 amino acids, preferably, from 1-25 amino acids, more preferably, from 1-10 amino acids) are contemplated and are within the scope of the present invention. Conservative amino acid substitutions will generally be preferred. Furthermore, alterations may be in the form of altered amino acids, such as peptidomimetics or D-amino acids, as already explained for the present polypeptides including antibodies.

DSC2 or a fragment thereof can be used as immunogen to obtain an antibody of the present invention. DSC2 can be derived from any species, preferably from a mammal such as a human, mouse, or rat, and more preferably from a human through conventional purification techniques. Moreover, the nucleotide and amino acid sequences of human DSC2 are known (cDNA nucleotide sequence of DSC2 type 2b (GenBank Accession No. NM_004949; SEQ ID NO: 1) and DSC2 type 2a (GenBank Accession No. NM_024422; SEQ ID NO:2), and the corresponding amino acid sequences are described in SEQ ID NOs: 3 (GenBank Accession No. NP_004940) and 4 (GenBank Accession No. NP_077740), respectively). Thus, to obtain an immunogen for preparing the present DSC2 antibody, a person may chemically synthesize or genetically produce DSC2 or antigenic fragments thereof based on these sequence information. For example, one skilled in the art can routinely isolate or construct a polynucleotide comprising the objective nucleotide sequence, insert the gene into a suitable expression vector to transform a suitable host cell, and obtain a protein comprising the target amino acid sequence by culturing the host cell under suitable conditions for expression of the protein from the cells or the culture supernatant. Furthermore, cells expressing the DSC2 protein or a fragment thereof can themselves be used as immunogens.

When using a fragment of DSC2 as the immunogen, it is particularly preferable to select an amino acid sequence which comprises a region predicted to be an extra-cellular domain. The region of positions 1 to 32 of the N-terminus of DSC2 is predicted to correspond to a signal sequence (Greenwood M D et al., Genomics 44: 330-5, 1997.). Thus, it is preferred to avoid the use of this region as an immunogen. Further, it is preferred to adopt the extra-cellular domains of the DSC2 as the immunogen to obtain an antibody of the present invention.

Methods for immunizing animals with antigens are well known in the art, and include intraperitoneal and subcutaneous antigen injections. Specifically, antigens can be diluted and suspended in an appropriate amount of phosphate buffered saline (PBS), physiological saline, or the like. As desired, antigen suspensions can be mixed with an appropriate amount of standard adjuvant such as Freund's complete adjuvant, and administered to mammals after emulsification. Subsequently, it is preferable that antigens mixed with an appropriate amount of Freund's incomplete adjuvant are administered in multiple doses every four to 21 days. An appropriate carrier can also be used for immunization. After carrying out immunization as outlined above, the antibody level in the serum of the immunized animal may be examined through standard methods.

Polyclonal antibodies against the DSC2 protein can be prepared from the immunized mammal for which an increase in the level of desired antibody could be confirmed. This can be achieved by collecting blood or serum from these animals. The polyclonal antibody of the present invention may be the collected serum itself or may be purified from the serum. For example, chromatography using affinity columns equipped with DSC2 protein or antigenic fragments thereof may be used for such purification. Furthermore, IgG and IgM can be prepared by further purification using protein A or protein G column.

To prepare monoclonal antibodies, first, antibody-forming cells are collected from mammals immunized with immunogens and that have been confirmed to show increased level of the desired antibody in serum. The cells are preferably collected from the spleen. The collected antibody-forming cells are fused with preferable parent cells, for example, mammalian myeloma cells, and more preferably, myeloma cells that have acquired properties for selection of fusion cells by pharmaceutical agents. The fusion can be achieved through any known methods, for example the methods of Milstein et al. (Galfre G and Milstein C, Methods Enzymol 73: 3-46, 1981).

Then, the hybridomas produced by cell fusion may be selected by culturing in a standard selective medium such as HAT medium (medium comprising hypoxanthine, aminopterin, and thymidine). Cell culture in HAT medium is usually continued for several days to several weeks, a period sufficient enough to kill all cells other than the desired hybridomas (unfused cells). Standard limiting dilutions are then carried out, and hybridoma cells that produce the desired antibodies are screened and cloned.

The obtained hybridomas are then transplanted to mice abdominal cavities, and ascites containing the objective monoclonal antibodies are collected. The antibodies can be purified from the ascite through conventional protein separation and/or purification methods including, for example, selected combinations of column chromatography, comprising but not limited to affinity chromatography, filtration, ultrafiltration, salt precipitation, dialysis, SDS polyacrylamide gel electrophoresis, isoelectric focusing, and so on (Antibodies: A Laboratory Manual, Harlow and David, Lane (edit.), Cold Spring Harbor Laboratory, 1988).

Protein A columns and Protein G columns can be used as affinity columns. Exemplary protein A columns in use include Hyper D, POROS, and Sepharose F. F (Pharmacia).

Exemplary chromatography (excluding affinity chromatography) include ion exchange chromatography, hydrophobic chromatography, gel filtration, reverse phase chromatography, and adsorption chromatography ("Strategies for Protein Purification and Characterization: A Laboratory Course Manual" Daniel R Marshak et al., Cold Spring Harbor Laboratory Press, 1996). The chromatography can be performed according to the procedure of liquid phase chromatographies such as HPLC or FPLC.

Any mammal can be immunized with the immunogen for the production of the present antibody. However, when preparing a monoclonal antibody by producing a hybridoma, it is preferable to consider compatibility with the parent cell used in the cell fusion for producing the hybridoma.

Generally, rodents, lagomorphs, or primates are used for such immunization. Rodents include, for example, mice, rats, and hamsters. Lagomorphs include, for example, rabbits. Primates include, for example, catarrhine (old world) monkeys such as *Macaca fascicularis, Macaca mulatta*, Sacred baboons, and chimpanzees.

Furthermore, the use of transgenic animals comprising a repertoire of human antibody genes is also known in the art (Ishida I, et al., Cloning and Stem Cells 4: 91-102, 2002). Similarly with other animals, to obtain a human monoclonal antibody, the transgenic animals are immunized, antibody-producing cells are then recovered from the animals, fused with myeloma cells to yield hybridomas, and anti-protein human antibodies can be prepared from these hybridomas (see International Publications Nos. 92-03918, 94-02602, 94-25585, 96-33735, and 96-34096).

Alternatively, lymphocytes that are immortalized with cancer genes can be used for monoclonal antibody production. For example, human lymphocytes infected with EB virus or the like, can be immunized in vitro with immunogens. The immunized lymphocytes are then fused with human-derived myeloma cells able to divide unlimitedly (U266, etc.), thus obtaining hybridomas that produce the desired human antibodies (Japanese Patent Application Kokai Publication No. (JP-A) Sho 63-17688).

Once a monoclonal antibody has been obtained via any of the above-mentioned methods, it also can be prepared using genetic engineering methods (e.g., see Borrebaeck C A K and Larrick J W, Therapeutic Monoclonal Antibodies, MacMillan Publishers, UK, 1990). For example, a recombinant antibody can be prepared by cloning the DNA that encodes an objective antibody from the antigen-producing cell, such as hybridoma or immunized lymphocyte that produce the antibody; then inserting the cloned DNA into an appropriate vector; and transforming the vector into a suitable host cell. Such recombinant antibodies are also encompassed by the present invention.

Modified antibodies are also included in the present invention. Such modified antibodies can be obtained, for example, by chemical modification. For example, an antibody can be modified by linking to a molecule, such as polyethylene glycols (PEGs). Such chemical modification methods for antibodies are conventional to those skilled in the art and any known method may be adopted in the present invention. The antibodies can also be modified by other proteins. For example, an antibody linked with another protein molecule may be produced through genetic engineering. That is, a fusion protein of the antibody and the other protein can be expressed from an expression vector which includes a gene wherein the antibody gene and the gene coding for the other protein are linked. As a preferred example of the present invention, to enhance the effector function of the antibody, it may be linked with a cytokine or chemokine. It has been reported that the antibody effector function is enhanced via the linkage with IL-2, GM-CSF, or the like (Human Antibody 10: 43-9, 2000). IL-2, IL-12, GM-CSF, TNF, eosinophil chemotactic substance (RANTES) and the like can be used in the present invention to enhance the effector function of an antibody.

Moreover, modified antibodies include chimeric antibodies which, for example, are represented by humanized antibodies, wherein a variable region derived from a non-human antibody is conjugated to the constant region of a human antibody, or wherein CDRs from a non-human antibody is fused with the framework region (FR) derived from a human antibody (CDR-grafted antibody). Such chimeric antibodies may be obtained via standard techniques of molecular biology (see, e.g., Jones et al., Nature 321:522-5, 1986; Riechmann et al., Nature 332:323-7, 1988; and Presta, Curr Opin Struct Biol 2:593-6, 1992) for the production of humanized antibodies.

For example, first, genes encoding the variable region or CDR of an antibody of interest are prepared by polymerase chain reaction (PCR) or the like from RNA of antibody-producing cells (see, e.g., Larrick et al., "Methods: a Companion to Methods in Enzymology", Vol. 2: 106, 1991; Courtenay-Luck, "Genetic Manipulation of Monoclonal Antibodies" in Monoclonal Antibodies: Production, Engineering and Clinical Application; Ritter et al. (eds.), page 166, Cambridge University Press, 1995, and Ward et al., "Genetic Manipulation and Expression of Antibodies" in Monoclonal Antibodies: Principles and Applications; Birch et al. (eds.), page 137, Wiley-Liss, Inc., 1995). The prepared variable region-encoding genes are linked with genes that code for the constant region or framework regions. The genes encoding the constant region or framework regions may be determined similarly to the CDR-encoding genes, or it is also possible to prepare them based on sequence information of pre-existing antibodies. DNA sequences coding for the chimeric and CDR-grafted products may be synthesised completely or in part using oligonucleotide synthesis techniques. For example, oligonucleotide directed synthesis as described by Jones et al. (Nature 321:522-5, 1986) may be used. Further, in some cases, site-directed mutagenesis and polymerase chain reaction techniques may be used as appropriate. Techniques for oligonucleotide directed mutagenesis of a pre-existing variable region described by Verhoeyen et al. (Science 239: 1534-6, 1988) or Riechmann et al. (Nature 332: 323-7, 1988) may be employed for modifying the sequence of the variable region to, for example, enhance the binding ability of the chimeric antibody. In addition, if needed, enzymatic filling in of gapped oligonucleotides using T4 DNA polymerase as, for example, described by Queen et al., (Proc Natl Acad Sci USA 86: 10029-33, 1989; WO 90/07861) may be used.

In addition, the present antibodies encompass those wherein one or more amino acids have been replaced with other amino acids, or those wherein one or more amino acids are deleted, or added (including insertion) so long as the resulting antibody retains the binding ability to DSC2. Conventional methods used for other polypeptide, such as site-directed mutagenesis, may be employed for obtaining this kind of modified antibodies.

Similarly, fragments of any of the aforementioned present antibodies are also encompassed by the present invention so long as the resulting fragment retains the binding ability to DSC2. Such fragments are represented by Fv, Fab, and F(ab')$_2$, that can be obtained by treating antibodies with appropriate enzymes, such as papain or pepsin. However, much smaller fragments of the variable region of an antibody is included in the present invention. The fragments can be also obtained through chemical synthesis or conventional gene engineering methods by constructing genes encoding the fragments and expressing them.

Single-chain Fv (scFv) is also included in the present antibody. An sFv comprises the $V_H$ and $V_L$ domains of an antibody, wherein these domains are present in a single polypeptide chain. Preferably, the Fv polypeptide further comprises a polypeptide linker between the $V_H$ and $V_L$ domains which enables the scFv to form the desired structure for antigen binding. A number of methods have been described to discern chemical structures for converting the naturally aggregated but chemically separated light and heavy polypeptide chains from an antibody V region into an scFv molecule which will fold into a three dimensional structure substantially similar to the structure of an antigen-binding site (U.S. Pat. Nos. 5,091,513, 5,132,405, and 4,946,778; Pluckthun in The Pharmacology of Monoclonal Antibodies, vol. 113, Rosenburg and Moore eds., Springer-Verlag, New York, pp. 269-315, 1994) which all can be employed in the present invention.

Any suitable host cell/vector system may be used for expression of the DNA sequences coding for the modified antibodies. Bacterial, e.g., *E. coli*, and other microbial systems may be used, in particular for expression of antibody fragments such as FAb and (Fab')$_2$ fragments, and especially Fv fragments and single-chain antibody fragments, e.g., sc Fvs. Eucaryotic, e.g., mammalian, host cell expression systems may be used, in particular for production of larger CDR-grafted antibody products, including complete antibody molecules. Suitable mammalian host cells include CHO cells and myeloma or hybridoma cell lines.

The antigen-binding ability of an antibody of the present invention can be measured by using absorbance measurements, enzyme linked immunosorbent assays (ELISA), enzyme immunoassays (EIA), radioimmunoassays (RIA) and/or immunofluorescence methods. In ELISA, the antibody is immobilized on a plate, and an antigen thereto (e.g., the whole DSC2 protein or a fragment thereof) is added to the plate, and then a sample comprising the desired antibody such as the culture supernatant of cells that produce the antibody or purified antibody is added. A secondary antibody that recognizes the primary antibody and has been tagged with an enzyme such as alkaline phosphatase is then added, and the plate is incubated. After washing, an enzyme substrate such as p-nitrophenyl phosphate is added to the plate, absorbance is measured, and the antigen-binding ability of the objective sample is evaluated. The evaluation may be achieved using BIAcore (Pharmacia).

In addition, the effector function of the antibodies may be examined, for example, to select monoclonal antibodies which comprise more powerful effector function. For example, to assess ADCC activity of a molecule of interest, an in vitro ADCC assay, such as that described in U.S. Pat. No. 5,500,362 or U.S. Pat. No. 5,821,337 may be performed. Alternatively, ADCC activity of the molecule of interest may be assessed in vivo, e.g., in a animal model such as that disclosed in Clynes et al. (Proc Natl Acad Sci USA 95: 652-56, 1998). In addition, by following the methods outlined in the Example, the antibody effector function can also be evaluated. For example, target DSC2-expressing cells are incubated with effector cells in the presence of an antibody whose effector function is to be evaluated. If target cell destruction is detected, the antibody can be confirmed to have effector function that induces ADCC. The level of observed target cell destruction, in the absence of either antibodies or effector cells, can be compared as a control. Cells expressing DSC2 can be used as the target cells, including the variety of cell lines confirmed to express DSC2 in the Examples. These cell lines can be obtained from cell banks.

Further, to assess CDC activity of a molecule of interest, a CDC assay, e.g., as described by Gazzano-Santoro et al. (J Immunol Methods 202: 163-71, 1997) may be performed.

The antibodies of the present invention can be used not only for purifying or detecting DSC2, but also serve as candidates for agonists and antagonists of this protein. These antibodies can also be applied to antibody therapies for diseases wherein the expression of DSC2 is implicated. When using for treating humans, human antibodies or humanized antibodies are preferred due to their low immunogenicity.

II. Polynucleotides

Furthermore, the present invention provides polynucleotides encoding the above-described polypeptides of the present invention, including the antibodies. Any form of the polynucleotide of the present invention can be used so long as it encodes the present polypeptides, including mRNA, RNA, cDNA, genomic DNA, chemically synthesized polynucleotides, and the like. The present polynucleotides include those comprising a given nucleotide sequences as well as their degenerate sequences, so long as the resulting substance encodes the objective polypeptide of the present invention or equivalents thereof.

Preferably, the polynucleotide of the present invention includes a sequence coding for a polypeptide which consists of or comprises the amino acid sequence selected from the group of:

```
FSSFGMH,                (SEQ ID NO: 26)
YISSGSSTIYYADTVK,       (SEQ ID NO: 27)
VHYYYFDY,               (SEQ ID NO: 28)
KASQDINKYIA,            (SEQ ID NO: 29)
YTSTLQP,                (SEQ ID NO: 30)
LQYDNLW,                (SEQ ID NO: 31)
DYSMH,                  (SEQ ID NO: 32)
WINTETGEPTYADDFKG,      (SEQ ID NO: 33)
WLLFDY,                 (SEQ ID NO: 34)
KSSQSLLNSSNQKNYLA,      (SEQ ID NO: 35)
FASTRES,                (SEQ ID NO: 36)
QQHYSTPL,               (SEQ ID NO: 37)
GNYWS,                  (SEQ ID NO: 39)
EINHSGNTKYNPSLKS,       (SEQ ID NO: 40)
VPFDWFHPPGEPPFYYYGMDV,  (SEQ ID NO: 41)
```

-continued
```
TGSSSNIGAGYDVH,         (SEQ ID NO: 44)
GNSNRPS,                (SEQ ID NO: 45)
QSYDSSLSGWV,            (SEQ ID NO: 46)
GYFWS,                  (SEQ ID NO: 49)
EINHSGSTSYNPSLKS,       (SEQ ID NO: 50)
GQGYYSSLDP,             (SEQ ID NO: 51)
SGSSSNIGSNTVN,          (SEQ ID NO: 53)
SNNQRPS,                (SEQ ID NO: 54)
and
AAWDDSLNGVV.            (SEQ ID NO: 55)
```

The present polynucleotide may encode an antibody. Such antibody encoding polynucleotide of the present invention may encode an antibody that comprises a complementarity determining region (CDR) having sequences as follows:

```
group 1-1:
FSSFGMH (SEQ ID NO: 26) as VH CDR1,

YISSGSSTIYYADTVK (SEQ ID NO: 27) as VH CDR2,
and

VHYYYFDY (SEQ ID NO: 28) as VH CDR3;

group 1-2:
KASQDINKYIA (SEQ ID NO: 29) as VL CDR1,

YTSTLQP (SEQ ID NO: 30) as VL CDR2,
and

LQYDNLW (SEQ ID NO: 31) as VL CDR3;

group 2-1:
DYSMH (SEQ ID NO: 32) as VH CDR1,

WINTETGEPTYADDFKG (SEQ ID NO: 33) as VH CDR2,
and

WLLFDY (SEQ ID NO: 34) as VH CDR3;

group 2-2:
KSSQSLLNSSNQKNYLA (SEQ ID NO: 35) as VL CDR1,

FASTRES (SEQ ID NO: 36) as VL CDR2,
and

QQHYSTPL (SEQ ID NO: 37) as VL CDR3;

group 3-1:
GNYWS (SEQ ID NO: 39) as VH CDR1,

EINHSGNTKYNPSLKS (SEQ ID NO: 40) as VH CDR2,
and

VPFDWFHPPGEPPFYYYGMDV (SEQ ID NO: 41) as VH CDR3;

group 3-2:
TGSSSNIGAGYDVH (SEQ ID NO: 44) as VL CDR1,

GNSNRPS (SEQ ID NO: 45) as VL CDR2,
and

QSYDSSLSGWV (SEQ ID NO: 46) as VL CDR3;

group 4-1:
GYFWS (SEQ ID NO: 49) as VH CDR1,

EINHSGSTSYNPSLKS (SEQ ID NO: 50) as VH CDR2,
```

-continued and

GQGYYSSLDP (SEQ ID NO: 51) as VH CDR3;
and group 4-2:
SGSSSNIGSNTVN (SEQ ID NO: 53) as VL CDR1, SNNQRPS (SEQ ID NO: 54) as VL CDR2,
and AAWDDSLNGVV (SEQ ID NO: 55) as VL CDR3.

Preferably, the above-described CDR1, CDR2, and CDR3 sequences are separated by appropriate framework amino acid sequences so that the resulting fragment shows binding affinity to DSC2.

In addition, a polynucleotide of the present invention may encode an antibody that comprises the mouse VH amino acid sequence of SEQ ID NO: 20 or 22, and mouse VL amino acid sequence of SEQ ID NO: 21 or 23, or an antibody that comprises the human VH amino acid sequence of SEQ ID NO: 16 or 18, and the human VL amino acid sequence of SEQ ID NO: 17 or 19.

Furthermore, the present polynucleotide encoding an antibody may comprise a region that encodes for an Fc region of the antibody. Preferable Fc region encoded by the polynucleotide includes that of human IgG1, but the present invention is not restricted thereto.

The polynucleotide of the present invention can be prepared by methods known to those skilled in the art including genetic engineering methods and chemical synthesis. For example, it can be prepared by: preparing a cDNA library from cells which express the objective protein (e.g., antibody) of the invention, and conducting hybridization using a known partial sequence of the objective protein (e.g., if the objective protein is an antibody, the sequence coding for the constant region or framework region) as a probe. cDNA library construction can be achieved, for example, by the method described in Sambrook et al. (Molecular Cloning, Cold Spring Harbor Laboratory Press, 1989) or commercially available cDNA libraries may be used. Such library can also be prepared by extracting RNAs from cells expressing the objective protein, synthesizing oligo DNAs based on the known sequence of the objective protein, conducting PCR using the oligo DNAs as primers, and amplifying cDNAs encoding the objective protein.

In addition, by sequencing the nucleotide sequence of the obtained cDNA, the translation region encoded by the cDNA can be routinely determined, and the amino acid sequence of the objective protein can also be easily deduced. Moreover, the genomic DNA library can also be screened for the present protein using similar probes as screening the cDNA library to isolate genomic DNA of the objective protein.

More specifically, mRNAs may first be prepared from a cell, tissue, or organ in which the objective protein is expressed. Known methods can be used to isolate mRNAs, for instance, total RNA may be prepared by guanidine ultracentrifugation (Chirgwin et al, Biochemistry 18: 5294-9, 1979) or AGPC method (Chomczynski and Sacchi, Anal Biochem 162: 156-9, 1987). In addition, mRNA may be purified from total RNA using mRNA Purification Kit (Pharmacia) and the like, or may be directly purified by QuickPrep mRNA Purification Kit (Pharmacia).

The obtained mRNA is used to synthesize cDNA using reverse transcriptase. cDNA may be synthesized using commercially available kits such as AUV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002, 1988; Belyavsky et al., Nucleic Acids Res 17: 2919-32, 1989), which utilizes a primer, 5'-Ampli FINDER RACE Kit (Clontech), and PCR.

A desired DNA fragment is prepared from the PCR products and ligated with a vector DNA. The recombinant vectors are used to transform *E. coli* and the like, and a desired recombinant vector is prepared from a selected colony. The nucleotide sequence of the desired DNA can be verified by conventional methods including dideoxynucleotide chain termination.

The nucleotide sequence of a polynucleotide of the invention may be designed to be expressed more efficiently by taking into account the frequency of codon usage in the host used for the expression (Grantham et al., Nucleic Acids Res 9: 43-74, 1981). The sequence of the polynucleotide of the present invention may be altered by commercially available kits or conventional methods. For instance, the sequence may be altered by digestion with restriction enzymes, insertion of synthetic oligonucleotides or appropriate polynucleotide fragments, addition of linkers, and/or insertion of an initiation codon (ATG) and/or a stop codon (TAA, TGA, or TAG).

The present polynucleotide may be used for preparing a polypeptide of the invention. Furthermore, it may also be used for diagnosis and gene therapy against various diseases where DSC2 expressing cells are involved.

III. Vectors and Host Cells

The present invention also provides a vector into which the above polynucleotide of the present invention has been inserted. A vector of the invention is useful to keep a polynucleotide, especially a DNA, of the present invention in host cell, to express the polypeptide of the present invention, or to administer the polynucleotide of the present invention for gene therapy.

When *E. coli* is used a host cell and the vector is amplified and produced in a large amount in *E. coli* (e.g., JM109, DH5alpha, HB101, XL1Blue, etc.) the vector should have "ori" to be amplified in *E. coli* and a marker gene for selecting transformed *E. coli* (e.g., a drug-resistance gene selected by a drug such as ampicillin, tetracycline, kanamycin, chloramphenicol, etc.). For example, M13-series vectors, pUC-series vectors, pBR322, pBluescript, pCR-script, and the like can be used. In addition, pGEM-T, pDIRECT, and pT7 can also be used for subcloning and extracting cDNA as well as the vectors described above.

When, a vector is used to produce the polypeptide of the present invention, an expression vector is especially useful. For example, an expression vector to be expressed in *E. coli* should have the above characteristics to be amplified in *E. coli*. When *E. coli*, such as JM109, DHSalpha, HB101, or XL1Blue, are used as a host cell, the vector should have a promoter or the like, for example, lacZ promoter (Ward et al., Nature 341: 544-6, 1989; FASEB J 6: 2422-7, 1992), araB promoter (Better et al., Science 240: 1041-3, 1988) or T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for protein secretion. An exemplary signal sequence that directs the protein to be secreted to the periplasm of the *E. coli* is the pelB signal sequence (Lei et al., J Bacteriol 169: 4379-83, 1987). Means for introducing the vectors into the target host cells include, for example, the calcium chloride method and the electroporation method.

In addition to *E. coli*, for example, expression vectors derived from mammals (e.g., pcDNA3 (Invitrogen) and pEGF-BOS (Mizushima S and Nagata S., Nucleic Acids Res 18: 5322, 1990), pEF, pCDM8), expression vectors derived from insect cells (e.g., "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "Pichia Expression Kit" (Invitrogen), pNV11, SP-Q01), and expression vectors derived from *Bacillus subtilis* (e.g., pPL608, pKTH50) can be used for producing the polypeptide of the present invention.

In order to express the vector in animal cells, such as CHO, COS, or NIH3T3 cells, the vector should have a promoter necessary for expression in such cells, for example, the SV40 promoter (Mulligan et al., Nucleic Acids Res 277: 108, 1979), the MMLV-LTR promoter, the EF1alpha promoter (Mizushima et al., Nucleic Acids Res 19: 5322, 1990), the CMV promoter, and the like, and preferably a marker gene for selecting transformants (e.g., a drug resistance gene selected by a drug (neomycin, G418, etc.)). Examples of known vector with these characteristics include, for example, pMAM, pDR2, PBK-RSV, pBK-CMV, pOPRSV, and pOP13.

As has been mentioned above, when the polypeptide to be expressed is an antibody fragment, such as FAb and (Fab')$_2$ fragments, or sc Fvs, bacterial, e.g., *E. coli*, and other microbial systems are suitably used. Alternatively, eucaryotic, e.g., mammalian, host cell expression systems may be used, in particular, for production of larger polyeptides of the present invention like CDR-grafted antibody products, and complete antibody molecules. Suitable mammalian host cells include CHO cells and myeloma or hybridoma cell lines.

IV. Pharmaceutical Compositions

The present invention provides a pharmaceutical composition which comprises an anti-DSC2 antibody as an active ingredient, wherein the anti-DSC2 antibody damages (i.e., kills cells, is toxic to cells, or otherwise inhibits growth or division of cells) DSC2-expressing cells through antibody effector function.

The pharmaceutical composition can be used to treat any pathological condition associated with the expression of DSC2. In typical embodiments, the cell damaged by the present pharmaceutical composition is a cancer cell, such as lung, colon, pancreatic, prostate, breast, gastric, or liver cancer cell. More specifically, non-small cell lung cancer (NSCLC), colorectal carcinoma, pancreatic carcinoma, prostate carcinoma, breast duct carcinoma, tubular adenocarcinoma of the stomach, hepatocellular carcinoma (HCC) may be treated using the present compositions.

Any of the natural antibodies and modified antibodies described above under the item of "I-2. Antibodies" may be adopted for the present pharmaceutical composition so long as they show antibody effector function. It is preferred to use an isolated or purified antibody for the present composition. The antibody contained in the present pharmaceutical composition typically is a monoclonal antibody. However, the present invention is not limited thereto and any antibodies may be used for the present pharmaceutical composition so long as they comprise a desired effector function. Preferred effector functions include ADCC, CDC, and both. For example, antibodies comprising the Fc region of IgA, IgE, or IgG are essential for expressing ADCC. Similarly, the antibody Fc region of IgM or IgG is preferable for expressing CDC. Particularly preferred antibodies included in the composition are those belonging to the immunoglobulin class of IgG1. When the composition is used for treating human, human-derived antibodies belonging to these classes are particularly preferable in the present invention.

Furthermore, the antibody included in the present pharmaceutical composition may, in some embodiments, linked to cytotoxic agents via well known techniques. Numerous cytotoxic agents are known in the art and those that can be used in the present invention include, but are not limited to, cytotoxic drugs, toxins, and active fragments of such toxins. Suitable toxins and their corresponding fragments include diphtheria, A chain, exotoxin A chain, ricin A chain, abrin A chain, curcin, crotin, phenomycin, enomycin, auristatin and the like. Cytotoxic agents also include radiochemicals made by conjugating radioisotopes to the antibody or binding of a radionuclide to a chelating agent that has been covalently attached to the antibody. Methods for preparing such conjugates are well known in the art.

The present pharmaceutical composition can be administered to humans or other animals. In the present invention, animals other than humans to which the composition can be administered include mice, rats, guinea pigs, rabbits, chickens, cats, dogs, sheep, pigs, cows, monkeys, baboons, and chimpanzees.

The composition is formulated into a dosage form using known pharmaceutical formulation methods. For example, depending on requirements, it can be prepared to an injectable form that can be parenterally administered by making it as a sterile solution or suspension with water or other arbitrary pharmaceutically acceptable fluid. For example, the antibody to be included in the pharmaceutical composition can be mixed with acceptable carriers or solvents, specifically sterile water, physiological saline, vegetable oils, emulsifiers, suspension agents, surfactants, stabilizers, flavoring agents, excipients, solvents, preservatives, binding agents and the like, into a generally accepted unit dosage essential for use as a pharmaceutical agent. The phrase "pharmaceutically acceptable" indicates that the substance is inert and includes conventional substances used as diluent or vehicle for a drug. Suitable excipients and their formulations are described, for example, in Remington's Pharmaceutical Sciences, $16^{th}$ ed. (1980) Mack Publishing Co., ed. Oslo et al.

Other isotonic solutions comprising physiological saline, glucose, and adjuvants (such as D-sorbitol, D-mannose, D-mannitol, and sodium chloride) can be used as the injectable aqueous solution. They can also be used with appropriate solubilizers such as alcohols, specifically ethanols and polyalcohols (for example, propylene glycols and polyethylene glycol), and non-ionic surfactants (for example polysorbate 80™ or HCO-50).

Sesame oils or soybean oils can be used as an oleaginous solution, and benzyl benzoate or benzyl alcohols can be used with them as a solubilizer. Buffer solutions (phosphate buffers, sodium acetate buffers, etc.), analgesics (procaine hydrochloride, etc.), stabilizers (benzyl alcohol, phenols, etc.), and antioxidants can be used in the formulation. The prepared injections can be packaged into appropriate ampules.

Alternatively, nucleic acids comprising sequences encoding antibodies or functional derivatives thereof, are administered to treat or prevent diseases associated with DSC2-expressing cells, such as pancreatic, lung, colon, prostate, breast, gastric, and liver cancer, by way of gene therapy. Gene therapy refers to therapy performed by the administration to a subject of an expressed or expressible nucleic acid. In this embodiment of the invention, the nucleic acids produce their encoded antibody or antibody fragment that mediates a prophylactic or therapeutic effect.

Any of the methods for gene therapy available in the art can be used according to the present invention. Exemplary methods are described below.

For general reviews of the methods of gene therapy, see Goldspiel et al., Clin Pharm 2: 488-505, 1993; Wu and Wu, Biotherapy 3: 87-95, 1991; Tolstoshev, Ann Rev Pharmacol Toxicol 32: 573-96, 1993; Mulligan, Science 260: 926-32, 1993; Morgan and Anderson, Ann Rev Biochem 62: 191-217, 1993; Trends Biotechnol 11(5): 155-215, 1993. Methods commonly known in the art of recombinant DNA technology which can be used are described in Ausubel et al. (eds.), Current Protocols in Molecular Biology, John Wiley & Sons, NY, 1993; Kriegler, Gene Transfer and Expression, A Laboratory Manual, Stockton Press, NY, 1990.

In a preferred aspect, a composition of the invention comprises nucleic acids encoding an antibody, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc Natl Acad Sci USA 86:8932-5, 1989; Zijlstra et al., Nature 342:435-8, 1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J Biol Chem 262: 4429-32, 1987) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180, WO 92/22635, WO92/20316, WO93/14188 or WO 93/20221). Alternatively, the nucleic acid can be introduced intracellularly and incorporated within host cell DNA for expression, by homologous recombination (Koller and Smithies, Proc Natl Acad Sci USA 86:8932-5, 1989; Zijlstra et al., Nature 342:435-8, 1989).

In a specific embodiment, viral vectors that contains nucleic acid sequences encoding an antibody of the invention are used. For example, a retroviral vector can be used (see Miller et al., Methods Enzymol 217: 581-99, 1993). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a subject. More detail about retroviral vectors can be found in Boesen et al., (Biotherapy 6: 291-302, 1994) which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J Clin Invest 93: 644-51, 1994; Kleim et al., Blood 83: 1467-73, 1994; Salmons and Gunzberg, Hum Gene Ther 4: 129-41, 1993; Grossman and Wilson, Curr Opin Genet Dev 3: 110-4, 1993.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (Curr Opin Genet Dev 3: 499-503, 1993) present a review of adenovirus-based gene therapy. Bout et al. (Hum Gene Ther 5: 3-10, 1994) demonstrates the use of adenovirus vectors to transfer genes to the respiratory epithelia of rhesus monkeys. Other instances of the use of adenoviruses in gene therapy can be found in Rosenfeld et al., Science 252: 431-4, 1991; Rosenfeld et al., Cell 68: 143-55, 1992; Mastrangeli et al., J Clin Invest 91: 225-34, 1993; WO94/12649; Wang et al., Gene Ther 2: 775-83, 1995. In a preferred embodiment, adenovirus vectors are used.

Adeno-associated virus (AAV) has also been proposed for use in gene therapy (Walsh et al., Proc Soc Exp Biol Med 204: 289-300, 1993; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, Methods Enzymol 217: 599-618, 1993; Cotten et al., Methods Enzymol 217: 618-44, 1993; Cline M J, Pharmacol Ther 29: 69-92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the subject.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., WO 94/08598; Stemple and Anderson, Cell 71: 973-85, 1992; Rheinwald, Methods Cell Biol 21A: 229-54, 1980; Pittelkow and Scott, Mayo Clin Proc 61: 771-7, 1986).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The pharmaceutical compositions comprise the active ingredients (a polypeptide or polynucleotide of the present invention) at a pharmaceutically effective amount. A "pharmaceutically effective amount" of a compound is a quantity that is sufficient to treat and/or prevent disorders wherein the expression of DSC2 plays important roles. An example of a pharmaceutically effective amount may an amount that is needed to decrease the number of DSC2 expressing cells in a cancerous tissue when administered to a patient, so as to thereby treat or prevent the disorders. The decrease may be, for example, at least a decrease of about 5%, 10%, 20%, 30%, 40%, 50%, 75%, 80%, 90%, 95%, 99%, or 100%. Alternatively, a pharmaceutically effective amount may be an amount that leads to a decrease in size, prevalence, or metastatic potential of the tumor in a subject.

The assessment to determine such a pharmaceutically effective amount of an antibody of the present invention can be made using standard clinical protocols including histopathologic diagnosis or through identification of symptomatic anomalies such as chronic cough, hoarseness, coughing up blood, weight loss, loss of appetite, shortness of breath, wheezing, repeated bouts of bronchitis or pneumonia, and chest pain.

The dose employed will depend upon a number of factors, including the age and sex of the subject, the precise disorder being treated, and its severity. Also the route of administration may vary depending upon the condition and its severity. However, the determination of an effective dose range for the identified compounds is well within the capability of those skilled in the art, especially in light of the detailed disclosure provide herein. The pharmaceutically or preventively effective amount (dose) of a compound can be estimated initially from cell culture assays and/or animal models.

If needed, a pharmaceutical composition comprising the antibody may include any other therapeutic substance as an active ingredient so long as the substance does not inhibit the in vivo effector function of the antibody. It should be understood that in addition to the ingredients particularly mentioned above, the formulations may include other agents conventional in the art having regard to the type of formulation in question.

In one embodiment of the present invention, a pharmaceutical composition comprising the antibody may be included in articles of manufacture and kits containing materials useful for treating the pathological conditions of object. The article of manufacture may comprise a container of any of the compounds with a label. Suitable containers include bottles, vials, and test tubes. The containers may be formed from a variety of materials, such as glass or plastic. The label on the container should indicate the composition is used for treating or preventing one or more conditions of the disease. The label may also indicate directions for administration and so on.

In addition to the container described above, a kit comprising a pharmaceutical composition comprising the antibody may optionally comprise a second container housing a pharmaceutically-acceptable diluent. It may further include other materials desirable from a commercial and user standpoint, including other buffers, diluents, filters, needles, syringes, and package inserts with instructions for use.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

V. Method for Damaging DSC2-Expressing Cells

The present invention also provides a method for damaging DSC2-expressing cells. Specifically, the method comprises the step of contacting the DSC2-expressing cells with anti-DSC2 antibodies. Through the contact of the antibody, the cells are expected to be damaged due to the effector function of the antibody.

Through the method of the present invention, any DSC2-expressing cell can be damaged or killed. For example, lung, colon, pancreatic, prostate, breast, gastric, or liver cancer cells are preferable as the DSC2-expressing cells of the present invention. Of these, non-small cell lung cancer (NSCLC), colorectal carcinoma, pancreatic carcinoma, prostate carcinoma, breast duct carcinoma, tubular adenocarcinoma of the stomach, hepatocellular carcinoma (HCC), or cells are preferable.

Cells and antibodies can be contacted in vivo or in vitro. When targeting in vivo cancer cells as the DSC2-expressing cells, the methods of the present invention are in fact therapeutic methods or preventative methods for cancers. Specifically, the present invention provides therapeutic methods for cancers which comprise the following steps:

1) administering an antibody that binds DSC2 to a cancer patient, and
2) damaging cancer cells in the patient through the effector function of the antibody that bound to those cells.

Any of the natural antibodies and modified antibodies described above under the item of "I-2. Antibodies" may be employed for the present method so long as they show antibody effector function. It is preferred to use isolated or purified antibodies for the present method. Alternatively, any of the pharmaceutical compositions described above under the item of "IV. Pharmaceutical Compositions" may be adopted for the present method.

In the present invention, humans or other animals including mice, rats, guinea pigs, rabbits, chickens, cats, dogs, sheep, pigs, cows, monkeys, baboons, and chimpanzees may be treated.

In the present invention, the antibodies or pharmaceutical compositions can be administered to patients, for example, intraarterially, intravenously, or percutaneously, or intranasally, transbronchially, locally, or intramuscularly. Intravascular (intravenous) administration by drip or injection is an example of a general method for systematic administration to lung, colon, pancreatic, prostate, breast, gastric or liver cancer patients. Methods of locally concentrating the administered agent to the primary focus or metastatic focus in the lung include local injection using a bronchoscope (bronchoscopy) and local injection under CT guidance or with thoracoscopy. Methods of locally concentrating the agents to the primary focus or metastatic focus in the liver include local injection using a hepatic portal injection or arterial infusion. In addition, methods in which an intraarterial catheter is inserted near a vein that supplies nutrients to cancer cells to locally inject anti-cancer agents, are effective as local control therapies for metastatic focuses as well as primary focuses of lung, colon, pancreatic, prostate, breast, gastric or liver cancer.

Although dosage and administration methods vary according to patient body weight and age, and administration method, these can be routinely selected by one skilled in the art. For example, anti-DSC2 antibodies can be administered to living bodies in an amount such that cytotoxicity based on effector function against DSC2-expressing cells can be confirmed. For example, although there is a certain amount of difference depending on symptoms, anti-DSC2 antibody dosage is 0.1 mg to 250 mg/kg per day. Usually, the dosage for an adult (of weight 60 kg) is 5 mg to 17.5 g/day, preferably 5 mg to 10 g/day, and more preferably 100 mg to 3 g/day. The dosage schedule is from one to ten times over a two to ten day interval, and for example, progress is observed after a three to six times administration.

VI. Immunogenic Compositions

According to the present invention, it was discovered that the administration of anti-DSC2 antibody damages cancer cells through the effector function of the antibody. Therefore, the present inventors considered that a composition inducing DSC2 antibodies with effector function has equivalent therapeutic effects with the present pharmaceutical composition comprising an antibody with effector function. It is expected that such vaccinating effect can be achieved by administering DSC2 polypeptide, or a nucleic acid molecule that expresses the polypeptide. Thus, the present invention provides immunogenic compositions for inducing antibodies with at least one effector function against DSC2-expressing cells in vivo. The compositions typically comprise as an active ingredient, a DSC2 polypeptide, or a nucleic acid molecule that expresses the polypeptide. It is preferred that the polypeptide or the nucleic acid molecule is an isolated or purified substance.

The immunogenic compositions of the present invention are particularly useful in vaccine therapy against diseases associated with DSC2-expressing cells.

The immunogenic compositions of the present invention are effective as, for example, vaccine compositions for lung, colon, pancreatic, prostate, breast, gastric or liver cancer therapies. They may be used against humans and other animals, including mice, rats, guinea pigs, rabbits, chickens, cats, dogs, sheep, pigs, cows, monkeys, baboons, and chimpanzees.

The DSC2 polypeptide included in the present immunological composition may be either the whole DSC2 protein or a fragment thereof so long as the fragment retains the ability to induce in vivo antibodies that recognize DSC2 and have effector function. Herein after, such fragments will be called immunologically active fragments.

The DSC2 polypeptide can be derived from any species, preferably from a mammal such as a human, mouse, or rat, and more preferably from a human to be treated with the composition through conventional purification techniques. Moreover, the nucleotide and amino acid sequences of human DSC2 are known (cDNA nucleotide sequence of DSC2 type 2b (GenBank Accession No. NM_004949; SEQ ID NO: 1) and DSC2 type 2a (GenBank Accession No. NM_024422; SEQ ID NO:2), and the corresponding amino acid sequences are described in SEQ ID NOs: 3 (GenBank Accession No. NP_004940) and 4 (GenBank Accession No. NP_077740), respectively). Thus, to obtain the DSC2 polypeptide, a person may chemically synthesize or genetically produce the polypeptide based on these sequence information. For example, one skilled in the art can routinely isolate or construct a polynucleotide comprising the objective nucleotide sequence, insert the gene into a suitable expression vector to transform a suitable host cell, and obtain a protein comprising the target amino acid sequence by culturing the host cell under suitable conditions for expression of the polypeptide from the cells or the culture supernatant.

An immunologically active fragment of the whole DSC2 protein may also be prepared based on the above sequence information. Since the region of positions 1 to 32 of the N-terminus of DSC2 is predicted to correspond to a signal sequence (Greenwood M D. et al., Genomics 44(3): 330-5, 1997 Sep. 15), it is preferred to avoid this region for the fragment. The extra-cellular domains (position 144 to 540 of DSC2) are particularly preferred as the immunologically active fragment to be included in the present composition. However, the present invention is not restricted thereto, and much shorter polypeptides may be adopted as the immunologically active fragment.

Furthermore, the DSC2 polypeptide may be a protein which has been modified from the natural occurring DSC2 protein so long as the modified molecule has the ability to induce in vivo antibodies that recognize DSC2 and have effector function. Such modifications include those mentioned above for the antibody of the present invention.

In addition to the immunogenic proteins (whole DSC2 polypeptides, immunologically active fragments thereof, and modified molecules thereof), the present immunogenic composition may comprise pharmaceutically acceptable carriers. Similar substances to those mentioned for the pharmaceutical composition of the invention may be employed as pharmaceutically acceptable carriers for the present immunogenic composition. If necessary, the compositions can also be combined with an adjuvant. Killed tuberculosis bacteria, diphtheria toxoid, saponin and the like can be used as the adjuvant.

Alternatively, DNAs coding for the immunogenic proteins, or cells retaining those DNAs in an expressible state, can be used as the active ingredient of the present immunogenic compositions. Methods for using DNAs expressing the target antigen as immunogens, so-called DNA vaccines, are well known in the art. For example, DNA vaccines can be obtained by inserting a DNA encoding a whole DSC2 polypeptide, immunologically active fragment thereof, or a modified molecule thereof into an appropriate expression vector.

Retrovirus vectors, adenovirus vectors, adeno-associated virus vectors, Sendai virus vectors or such can be used as the vector. In addition, DNAs in which a DNA encoding an immunogenic protein is functionally connected downstream of a promoter can be directly introduced into cells as naked DNA, and then expressed. Naked DNA can be encapsulated in ribosomes or viral envelope vectors and introduced into cells.

When DNAs encoding the immunogenic proteins, or cells transformed with the same are used as immunogenic compositions of the present invention, they can be combined with immunogenic proteins as well as carrier proteins that enhance their immunogenic properties. For more details, the explanation on pharmaceutical compositions containing nucleic acids comprising sequences encoding antibodies or functional derivatives thereof can be referred.

Whether a given polypeptide or polynucleotide induces antibodies against the polypeptide in vivo can be determined by actually immunizing an animal, and confirming the activity of the induced antibodies. Similarly, the induction of anti-tumor immunity by a polypeptide can be confirmed by observing the induction of antibody production against tumors in an animal immunized with the polypeptide. For example, when antibodies against a polypeptide are induced in a laboratory animal immunized with the polypeptide, the suppression of tumor cell growth indicates the ability of the polypeptide to induce anti-tumor immunity. The ability for antibody induction and confirmation of the property of the induced antibody of a polypeptide can be carried out, for example, using methods described in Examples.

VII. Induction of Immune Response

Moreover, the present invention provides a method for inducing antibodies with at least one effector function against DSC2-expressing cells in vivo. Specifically, the method comprises administering the aforementioned immunogenic composition of the present invention to a subject. For example, each day, 0.1 mg to 250 mg per kilogram of the immunogenic composition of the present invention can be administered orally or parenterally. Parenteral administration includes subcutaneous injection and intravenous injection. The administrative dose for a single adult is usually 5 mg to 17.5 g/day, preferably 5 mg to 10 g/day, and more preferably 100 mg to 3 g/day.

The method may be employed for treating diseases associated with DSC2-expressing cells, like lung, colon, pancreatic, prostate, breast, gastric or liver cancers.

Furthermore, the DSC2 polypeptide and nucleic acid molecules encoding the polypeptide can also be used for the induction of immune response in vivo other than the production of antibodies against the DSC2 polypeptide. Namely, it is known that cytotoxic T lymphocytes (CTL) specific for a protein can be induced by presenting the protein to a T cell via an antigen presenting cell (APC) either in vivo or ex vivo. Thus, similarly, the DSC2 polypeptide may be presented to T cells either in vivo or ex vivo for the induction of CTL. It is preferred to use purified or isolated polypeptides or nucleic acid molecule for such induction of immune response.

For example, patient blood cells e.g., peripheral blood mononuclear cells (PBMC) are collected, transformed with a vector that expresses an immunogenic protein, and returned to the patient. Transformed blood cells produce the immunogenic protein inside the body of the patient, and induce objective antibodies.

Alternatively, PBMCs of the patient are collected, the cells are contacted with the immunogenic protein ex vivo, and following the induction of APCs or CTLs, the APCs or CTLs may be administered to the subject. Further, if needed, APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells have been derived, but also for other individuals with similar types of tumors.

Generally, when using a polypeptide for cellular immunotherapy, efficiency of the CTL-induction is known to be increased by combining a plurality of polypeptides having different structures and contacting them with APCs, particularly, dendritic cells. Therefore, when stimulating APCs with protein fragments, it is advantageous to use a mixture of multiple types of fragments.

All prior art references cited herein are incorporated by reference in their entirety.

BEST MODE FOR CARRYING OUT THE INVENTION

Figure 1:
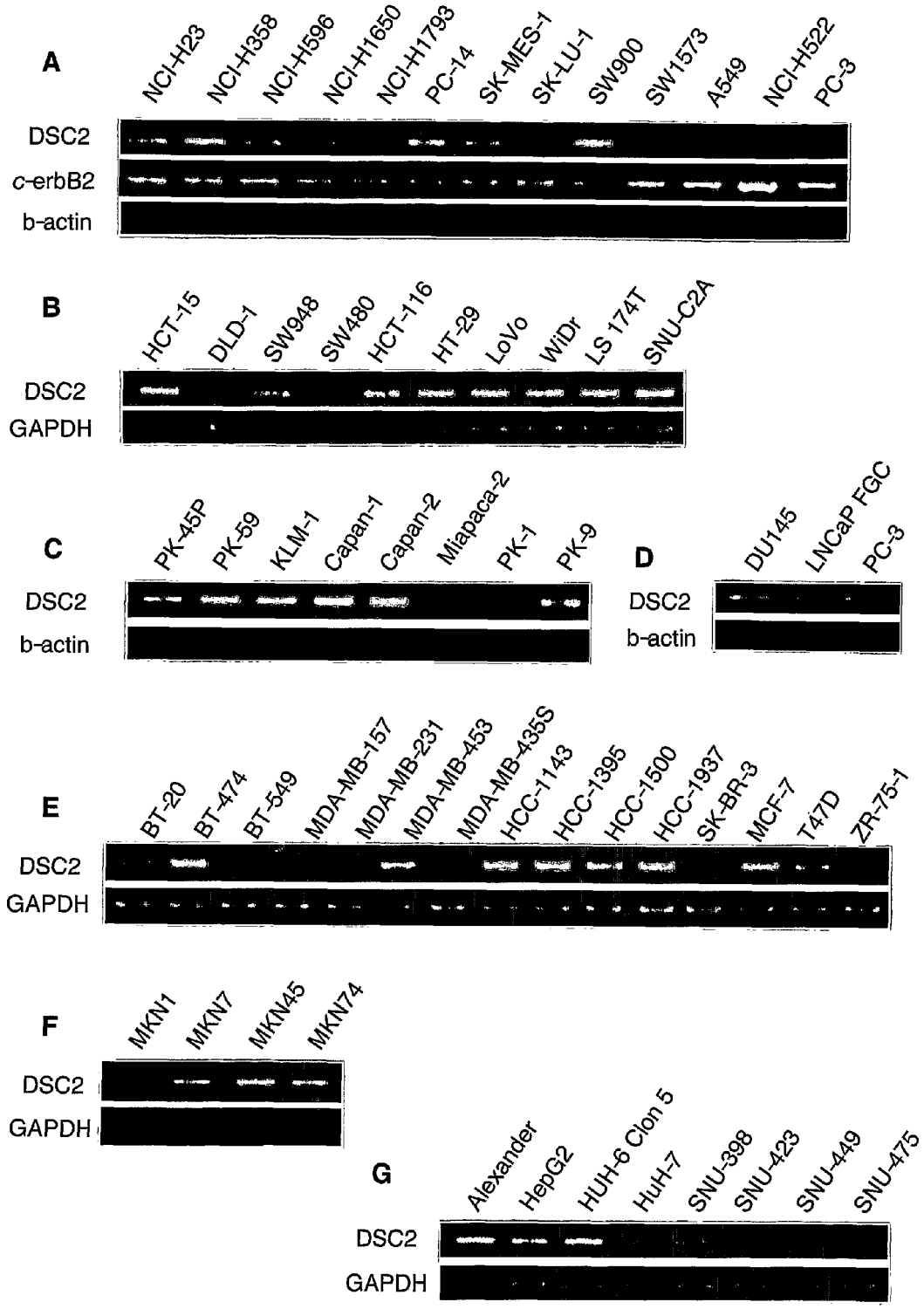
FIG. 1 depicts the result of Semiquantitative RT-PCR analysis for the DSC2 gene in cancer cells. Panel A: lung cancer cell lines; panel B: colon cancer cell lines; panel C: pancreatic cancer cell lines; panel D: prostate cancer cell lines; panel E: breast cancer cell lines; panel F: gastric cancer cell lines; panel G: liver cancer cell lines. The expression level of Herceptin target gene c-erbB2 gene for breast cancer is indicated in panel A as positive control.

Below, the present invention is further explained based on Examples. However, materials, methods and such described therein only illustrate aspects of the invention and in no way are intended to limit the scope of the present invention. As such, materials, methods and such similar or equivalent to those described therein may be used in the practice or testing of the present invention.

(1) Cell Lines

Human lung, colon, pancreatic, prostate, breast, gastric and liver cancer cell lines were propagated as a monolayer in an appropriate medium supplemented with 10% fetal bovine serum. The cell lines used in the experiment are shown in Table 1.

TABLE 1

| Cell line | Medium | Source |
|---|---|---|
| Lung cancer Cell lines | | |
| NCI-H23 | RPMI + 10% FBS | American Type Culture Collection (ATCC) CRL-5800 |
| NCI-H358 | RPMI + 10% FBS | ATCC CRL-5807 |
| NCI-H596 | RPMI + 10% FBS | ATCC HTB-178 |
| NCI-H1650 | RPMI + 10% FBS | ATCC CRL-5883 |
| NCI-H1793 | F12*1 + D-MEM*2 + 10% FBS | ATCC CRL-5896 |
| PC-14 | RPMI + 10% FBS | RIKEN Bioresource Center |
| SK-MES-1 | E-MEM*3 + 10% FBS + 2 mM L-glutamin | ATCC HTB-58 |
| SK-LU-1 | E-MEM*3 + 10% FBS + 2 mM L-glutamin | ATCC HTB-57 |
| SW900 | L15*4 + 10% FBS | ATCC HTB-59 |
| SW1573 | L15*4 + 10% FBS | ATCC CRL-2170 |
| A549 | RPMI + 10% FBS | ATCC CCL-185 |
| NCI-H522 | RPMI + 10% FBS | ATCC CRL-5810 |
| PC-3 | E-MEM*3 + 10% FBS | Health Science Research Resources Bank (HSRRB): JCRB0077 |
| Colon cancer Cell lines | | |
| HCT-15 | RPMI + 20% FBS | ATCC CCL-225 |
| DLD-1 | RPMI + 10% FBS | ATCC CCL-221 |
| SW948 | L15*4 + 10% FBS | ATCC CCL-237 |
| SW480 | L15*4 + 10% FBS | ATCC CCL-228 |
| HCT-116 | McCoy*5 + 10% FBS | ATCC CCL-247 |
| HT-29 | McCoy*5 + 10% FBS | ATCC HTB-38 |
| LoVo | F12*1 + 20% FBS | ATCC CCL-229 |
| WiDr | E-MEM*3 + 10% FBS + 2 mM L-glutamin | ATCC CCL-218 |
| LS 174T | E-MEM*3 + 10% FBS | ATCC CL 188 |
| SNU-C2A | F12*1 + D-MEM*2 + 10% FBS + 2 mM L-glutamin | ATCC CCL-250.1 |
| Pancreatic cancer Cell lines | | |
| PK-45P | RPMI + 10% FBS | TKG*6: TKG 0493 |
| PK-59 | RPMI + 10% FBS | TKG*6: TKG 0492 |
| KLM-1 | RPMI + 10% FBS | TKG*6: TKG 0490 |
| Capan-1 | RPMI + 10% FBS | ATCC HTB-79 |
| Capan-2 | McCoy*5 + 10% FBS | ATCC HTB-80 |
| Miapaca-2 | E-MEM*3 + 10% FBS | HSRRB: JCRB0070 |
| PK-1 | RPMI + 10% FBS | TKG*6: TKG 0239 |
| PK-9 | RPMI + 10% FBS | TKG*6: TKG 0240 |
| Prostate cancer Cell lines | | |
| DU145 | E-MEM*3 + 10% FBS + 2 mM L-glutamin | ATCC HTB-81 |
| LNCap FGC | RPMI + 10% FBS + 2 mM L-glutamin | ATCC CRL-1740 |
| PC-3 | F12*1 + 10% FBS | ATCC CRL-1435 |
| Breast cancer Cell lines | | |
| BT-20 | E-MEM*3 + 10% FBS | ATCC HTB-19 |
| BT-474 | D-MEM*2 + 10% FBS | ATCC HTB-20 |
| BT-549 | RPMI + 10% FBS | ATCC HTB-122 |
| HCC1143 | RPMI + 10% FBS | ATCC CRL-2321 |
| HCC1395 | RPMI + 10% FBS + 2 mM L-glutamin | ATCC CRL-2324 |
| HCC1500 | RPMI + 10% FBS + 2 mM L-glutamin | ATCC CRL-2329 |
| HCC1937 | RPMI + 10% FBS + 2 mM L-glutamin | ATCC CRL-2336 |
| MCF-7 | E-MEM*3 + 10% FBS | ATCC HTB-22 |
| MDA-MB-157 | L15*4 + 10% FBS | ATCC HTB-24 |
| MDA-MB-231 | L15*4 + 10% FBS | ATCC HTB-26 |
| MDA-MB-435S | L15*4 + 10% FBS | ATCC HTB-129 |
| MDA-MB-453 | McCoy*5 + 10% FBS | ATCC HTB-131 |
| SK-BR-3 | RPMI + 10% FBS | ATCC HTB-30 |

TABLE 1-continued

| Cell line | Medium | Source |
|---|---|---|
| T47D | RPMI + 10% FBS + 2 mM L-glutamin | ATCC HTB-133 |
| ZR-75-1 | E-MEM*3 + 10% FBS | ATCC CRL-1500 |
| Gastric cancer Cell lines | | |
| MKN1 | RPMI + 10% FBS | HSRRB: JCRB0252 |
| MKN7 | RPMI + 10% FBS | HSRRB: JCRB1025 |
| MKN45 | RPMI + 10% FBS | HSRRB: JCRB0254 |
| MKN74 | RPMI + 10% FBS | HSRRB: JCRB0255 |
| Liver cancer Cell lines | | |
| Alexander | D-MEM*2 + 10% FBS | HSRRB: IFO50069 |
| HepG2 | D-MEM*2 + 10% FBS | HSRRB: JCRB1054 |
| HUH-6 Clone 5 | E-MEM*3 + 10% FBS | HSRRB: JCRB0401 |
| HuH-7 | D-MEM*2 + 10% FBS | HSRRB: JCRB0403 |
| SNU-398 | RPMI + 10% FBS (heat inactivated) | ATCC CRL-2233 |
| SNU-423 | RPMI + 10% FBS | ATCC CRL-2238 |
| SNU-449 | RPMI + 10% FBS | ATCC CRL-2234 |
| SNU-475 | RPMI + 10% FBS | ATCC CRL-2236 |

*1 F-12 Nutrient Mixture (HAM)
*2 Dulbecco's Modified Eagle's medium
*3 Eagle's Minimal Essential medium
*4 Leibovitz's L-15 medium
*5 McCoy's 5A medium Modified
*6 Cell Resource Center for Biomedical Research Institute of Development, Aging and Cancer, Tohoku University Furthermore, the following cell lines were used in ADCC assays using anti-DSC2 antibodies:

non-small cell lung carcinoma (NSCLC): NCI-H358;

colon adenocarcinoma: HT-29;

pancreatic carcinoma: KLM-1;

prostate carcinoma: LNCap FGC;

breast duct carcinoma: T47D;

stomach tubular adenocarcinoma: MKN-7; and hepatocellular carcinoma (HCC): HepG2.

(2) Antibody Production:

(2-1) Polyclonal Antibodies

According to standard protocols, individual protein specific polyclonal antibodies were produced using His-tagged fusion proteins expressed in bacteria as immunogens. These fusion proteins comprised a protein portion that corresponded to a specific portion of the protein (residues 144 to 540).

(2-2) Monoclonal Antibodies

First, to obtain monoclonal antibodies, antigen coding genes encoding a domain of DSC2 (representing amino acids 1 to 901) and the extracellular domain (i.e., secretory form antigen DSC2-s, representing amino acids 1 to 688), respectively were amplified from normal lung cDNA. The primer were designed: 5'-AATA TTAATTAACTCCATGGAGGCAGCCC-3' (SEQ ID NO: 5) and 5'-ATCG GGATCCTCTCTTCATGCATGCTTCTGCTA-3' (SEQ ID NO: 6) for DSC2; 5'-AATA TTAATTAACTCCATGGAGGCAGCCC-3' (SEQ ID NO: 5) and 5'-AATAGGATCCTCCACCGCCAATCC-3' (SEQ ID NO: 7) for DSC2-s.

The PCR products were subcloned into expression vector pQCXIP (Clontech)-modified pQCXmHIPG (including the myc-His domain, EGFP, and IRES-puromycin domain), respectively. The plasmids were dubbed pQC/DSC2 mH/IPG for DSC2 and pQC/DSC2-s/IPG for DSC2-s, respectively.

To produce the recombinant protein of DSC2, 293T cells were transiently transfected with the plasmid pQC/DSC2 mH/IPG, using Lipofectamine 2000 (Invitrogen) according to the manufacturer's instructions, and after 48 h incubation, the 293T cells were harvested.

On the other hand, to produce the secretory form recombinant protein DSC2-s, a cell line was established using Pantropic Retroviral Expression System (Clontech) according to the manufacturer's instructions. Specifically, GP2-293 cells were co-transfected with pQC/DSC2-s/IPG and pVSV-G (Clontech). After 48 h incubation, virus-containing supernatants were centrifuged. The retrovirus vector solution was prepared by resuspending the precipitation with TNE solution (Tris-HCl, pH7.8, 130 mM NaCl, 1 mM EDTA). 293T cells were transfected with pQC/DSC2-s/IPG using the retrovirus vector solution diluted by 8 μg/mL hexadimethrine bromide (SIGMA)-containing DMEM supplemented with 10% FBS. The selection of pQC/DSC2-s/IPG-transfected 293T cells, DSC2-s/293T, was performed using 5 μg/mL puromycin (SIGMA). The His-tagged proteins in DSC2-s/293T-culture supernatants were purified using TALON Purification kit (Clontech).

The immunization of animals with DSC2 was achieved by immunizing 2.5×10$^6$ cells of DSC2-transfected 293T cells suspended in PBS to 4-weeks-old female BALB/c mice. Before cell immunization, mice were immunized with PBS emulsified in complete Freund's adjuvant (Mitsubishi Kagaka Iatron, Inc.). Alternatively, for the immunization with DSC2-s, 4-weeks-old female BALB/c mice were immunized with DSC2-s purified antigen emulsified in complete Freund's adjuvant.

After three immunizations with 2-day interval, respectively, the mice were immunized with DSC2-transfected 293T cells or DSC2-s purified antigen in PBS. Then, cells from the lymph node of immunized mice were harvested and fused with myeloma cell line, P3U1. The hybridomas were subcloned by selection using flow cytometry and subsequent single-cell cloning by limiting dilution. Antibody in cell culture supernatants of isolated hybridomas was confirmed by Immunoprecipitation analysis. Antibody-containing supernatants from positive clones were tested by ELISA for the relative binding affinity against the DSC2 extracellular domain expressed on DSC2 over-expressing cell line, H358. The antibody against DSC2 (representing amino acids 1 to 901) was designed 48-5, and that against DSC2-s (representing amino acids 1 to 688) as s10-4.

(2-3) Humanized Chimeric Antibodies

Humanized chimeric antibodies ch48-5 and chs10-4 based on the mouse monoclonal antibodies 48-5 and s10-4, respectively, were prepared according to previously reported methods (Alvin Y Liu et al., Proc Natl Acad Sci USA 84: 3439-43, 1987; Mitchel E Reff et al., Blood 83(2): 435-45, 1994). Specifically, total RNA was extracted from mouse 48-5 or s10-4 hybridoma cells by RNeasy Mini Kit (QIAGEN, 74104), and then reverse-transcribed to single-stranded cDNA using GenenRacer™ kit (Invitrogen, L1502-02). Gene encoding the variable region of the antibody (Fab) was determined by PCR using this cDNA as template and the following set of primers:

```
5'primer:
5' primer of the GeneRacer ™ kit;
and

3'primer:
5'-AATTTTCTTGTCCACCTTGGTG-3' (SEQ ID NO: 24) for
CH1 (IgG2a),
and

5'-CTAACACTCATTCCTGTTGAAGCTCT-3' (SEQ ID NO: 25)

for CL1 (kappa).
```

The obtained products were cloned and subjected to sequence analysis.

As a result, the amino acid sequence of mouse Ig L-chain variable regions and H-chain variable regions were determined as follows:

48-5, H-chain variable region:

```
                                          (SEQ ID NO: 20)
MDSRLNLVFLVLILKGVQCDVQLVESGGGLVQPGGSRKLSCAASGFTFSS

FGMHWVRQAPEKGLEWVAYISSGSSTIYYADTVKGRFTISRDNPKNTLFL

QMTSLRSEDTAMYYCARVHYYYFDYWGQGTTLTVSS,
and
```

L-chain variable region:

```
                                          (SEQ ID NO: 21)
MRPSIQFLGLLLFWLHGAQCDIQMTQSPSSLSASLGGKVTITCKASQDIN

KYIAWYQHKPGKGPRLLIHYTSTLQPGIPSRFSGSGSGRDYSFSISNLEP

EDIATYYCLQYDNLWTFGGGTKL;
and
``` s10-4, H-chain variable region:

```
                                          (SEQ ID NO: 22)
MAWVWTLLFLMAAAQSIQAQIQLVQSGPELKKPGETVKISCKASGYTFTD

YSMHWVKQAPGKGLKWMGWINTETGEPTYADDFKGRFAFSLETSASTAYL

QINNLKNEDTATYFCARWLLFDYWGQGTTLTVSS,
and
```

L-chain variable region:

```
                                          (SEQ ID NO: 23)
MESQTQVLMFLLLWVSGACADIVMTQSPSSLAMSVGQKVTMSCKSSQSLL

NSSNQKNYLAWYQQKPGQSPKLLVYFASTRESGVPDRFIGSGSGTDFTLT

ISSVQAEDLADYFCQQHYSTPLTFGAGTKL.
```

Genes corresponding to each of the variable regions were amplified by PCR and cloned into an antibody expression cassette vector using a NotI-BamHI brachet. A retrovirus vector wherein the expression of the variable region gene is controlled by the CMV promoter was used as the antibody expression cassette vector. The vector for expressing the H-chain contained the hygromycin resistance gene (SEQ ID NO: 85), and that for the L-chain contained the puromycin resistance gene (SEQ ID NO: 86).

The vectors expressing the H-chain and L-chains were co-transfected into Chinese hamster ovary (CHO) cells for 48-5 and s10-4, respectively. The cells were selected using F-12 medium containing 500 µg/ml hygromycin and 10 µg/ml puromycin, the medium was exchanged with serum-free medium (CHO—S—SFM; GIBCO, 12052-098), and the chimeric antibody contained in the culture supernatant was purified via Protein A column.

(2-4) Human Antibodies (i) Screening of Phase Expression Libraries Using Culture Cells The screening of human scFV antibody against DSC2 was achieved using a phage library encoding human scFV antibodies created in the Institute for Antibodies (IFA; Nagoya, Japan). Specifically, the screening of human scFV antibody against DSC2 was performed using phage library AIMS4 coding for human scFV antibodies (WO 01/062907) following the method described in JP-A 2005-185281.

More specifically, the 1st screening was conducted as follows: MIAPaca-2 cells showing high expression of DSC2 were cultured on 15 cm dishes, harvested with the addition of 2 mg/ml collagenase I and a cell dissociation buffer (both Gibco BRL), and washed with cooled PBS. A solution of human antibody phage library ($2 \times 10^{113}$ cfu) was mixed with $4 \times 10^7$ of the cells, BSA and $NaN_3$/MEM were added at final concentrations of 1% and 0.1%, respectively, and the final volume was adjusted to 1.6 ml. The mixture was gently agitated for 4 hrs at 4° C., dispensed at equal volumes into two tubes, poured onto organic solution (dibutyl phthalate:cyclohexane=9:1) and centrifuged at 3,000 rpm for 2 min. The supernatant was removed, the pellet (cells) were resuspended in 0.7 ml of 1% BSA/MEM, and centrifuged on equal volume of low polarity solvent. This step was repeated twice. The supernatant was removed, the cells were resuspended in 0.3 ml of PBS, frozen with liquid nitrogen, and melted at 37° C. to obtain phages within the cells.

These phages were allowed to infect 20 ml of E. coli DH12S (OD=0.5) for 1 hr. The infected cells were transferred into 600 ml of 2×YTGA medium (2×YT, 200 µg/ml ampicillin sulfate, 1% glucose), and cultured overnight at 30° C. A 10 ml aliquot thereof was added to 200 ml of 2×YTA medium (2×YT, 200 µg/ml ampicillin sulfate) and cultured for 1.5 hrs at 37° C. After additional incubation, $1 \times 10^{11}$ of helper phage KO7 was added and further cultured for 1 hr at 37° C. 800 ml of 2×YTGAK (2×YT, 200 µg/ml ampicillin sulfate, 0.05% glucose, 50 µg/ml kanamycin) were added and cultured overnight at 30° C. The culture was centrifuged at 8,000 rpm for 10 min, the supernatant was mixed with 200 ml of PEG liquid (20% polyethylene glycol 6000, 2.5M NaCl) and centrifuged at 8,000 rpm for 10 min. The phages are contained in the pellet, and the pellet was suspended in 10 ml of PBS and a portion thereof was used for examining the number of E. coli infected with the phage.

The second screening was performed similarly to the first screening using 0.8 ml of reactive solution (1% BSA, 0.1% $NaN_3$/MEM), $2 \times 10^7$ culture cells, and $1 \times 10^{10}$ phages screened in the first screening, wherein the total volume of the mixture was half of that used in the first screening.

The third screening was performed similarly to the second screening except that $2 \times 10^7$ of 293T cells transfected with DSC2 and the phages screened in the second screening were used.

(ii) DNA Sequencing and Expression Confirmation

The screened E. coli was diluted and cultivated on nutrient agar supplemented with 100 µg/ml of ampicillin. Obtained colonies were picked up and incubated overnight at 30° C. in 2×YTGA medium.

1. For sequencing, DNA was obtained from the culture with PI-50 (Kanebo), and the nucleotide sequence was determined by the dideoxy method.

2. The expression of the protein was detected as the expression of cp3 fusion protein. Specifically, 0.05 ml of the culture was added to 1.2 ml of 2×YTAI (2×YT, 200 µg/ml ampicillin sulfate, 0.5 mM IPTG) and incubated at 30° C. The supernatant was collected by centrifugation at 15,000 rpm for 5 min, and reacted on Maxisorp™ high protein-binding capacity ELISA plate (NUNC) for 2 hrs at 37° C. After aspirating the solution on the plate, the antibody on the plate was blocked with 5% BSA for 2 hrs at 37° C., and the blocking solution was removed. Rabbit anti-cp3 antibody (MBL) diluted to 1:2,000 with 0.05% Tween/PBS was added to the plate and reacted at room temperature for 1 hr, and the plate was washed with PBS. Similarly, HRP tagged goat anti-rabbit IgG antibody (MBL) diluted to 1:2,000 with 0.05% Tween/PBS was added to the plate, reacted at room temperature for 1 hr. and the plate was washed with PBS. 100 µl of OPD solution was added to the plate and reacted at room temperature for 15 min, the reaction was quenched by the addition of 2M ammonium sulfate. The fusion protein was detected by measuring the absorbance at 492 nm with SPECTRAmax340PC (Molecular Devices).

(iii) Flow Cytometry

Flow cytometry analysis confirmed that two clones of human scFV antibody, clones 332 and 545, positively reacted to the antigen. These two clones consisted of the following amino acid sequences:

clone 332, heavy chain:

```
                                            (SEQ ID NO: 16)
QVQLQQWGAGLLKPSETLSLTCAVYGGSFSGNYWSWIRQPPGKGLEWIGE

INHSGNTKYNPSLKSRVAISADTSKNQFSLKLSSVTAADTAVYYCARVPF

DWFHPPGEPPFYYYYGMDVWGQGTTVTVSS,
and light chain:
                                            (SEQ ID NO: 17)
HVILTQPPSVSGAPGQRVTISCTGSSSNIGAGYDVHWYQQLPGTAPKLLI

YGNSNRPSGVPDRFSGSKSGTSASLAITGLQAEDEADYYCQSYDSSLSGW

VFGGGTKLTVPG;
and
``` clone 545, heavy chain:

```
                                            (SEQ ID NO: 18)
QVQLQQWGAGLLKPSETLSLTCAVYGGSFSGYFWSWIRQAPGKGLEWIGE

INHSGSTSYNPSLKSRVTMTIDTSRKQFSLKLSSVTAADAAVYYCARGQG

YYSSLDPWGQGTLVTVSS,
and light chain:
                                            (SEQ ID NO: 19)
SYELTQPPSASGTPGQRVTISCSGSSSNIGSNTVNWYQQLPGTAPKLLIY

SNNQRPSGVPDRFSGSKSGTSASLAISGLQSEDEADYYCAAWDDSLNGVV

FGGGTKLTVLG.
```

These human scFV antibodies were converted to complete IgG forms at IFA.

(3) Semiquantitative RT-PCR for DSC2 and c-erbB2

Total RNA was extracted from the cell lines using the RNeasy® Kit (QIAGEN). In addition, mRNA was purified from total RNA by Oligo (dT)-cellulose column (Amersham Biosciences) and converted into first-strand cDNA by reverse transcription (RT) using SuperScript First-Strand Synthesis System (Invitrogen). Appropriate dilutions of each first-stranded cDNA were prepared for subsequent PCR amplification by monitoring GAPDH as a quantitative control. The primer sequences used were as follows:

```
                                         (SEQ ID NO: 8)
         5'-GTGCCTGTCTTCAATTCACAA-3'
         and (SEQ ID NO: 9)
         5'-TCTGATTCAGGGAGTGCGAA-3'
         for DSC2, (SEQ ID NO: 10)
         5'-GTATTTGATGGTGACCTGGGAAT-3'
         and (SEQ ID NO: 11)
         5'-CCCCTGGGTCTTTATTTCATCT-3'
         for c-erbB2, (SEQ ID NO: 12)
         5'-GTCAGTGGTGGACCTGACCT-3'
         and (SEQ ID NO: 13)
         5'-GGTTGAGCACAGGGTACTTTATT-3'
         for GAPDH, and (SEQ ID NO: 14)
         5'-GAGGTGATAGCATTGCTTTCG-3'
         and (SEQ ID NO: 15)
         5'-CAAGTCAGTGTACAGGTAAGC-3'
         for β-actin.
```

All PCR reactions involved initial denaturation at 94° C. for 2 min, cycles of 94° C. for 30 s, 58° C. for 30 s, and 72° C. for 1 min, and annealing step, which were conducted on GeneAmp PCR system 9700 (PE Applied Biosystems). The reactions included 21 and 32 cycles for GAPDH and c-erbB2, respectively, and the annealing temperature was lowered gradually from 62° C. to 58° C. for these genes. For β-actin, the reaction included 20 cycles and the annealing temperature was lowered gradually from 62° C. to 57° C., which was 30 cycles and lowering gradually from 62° C. to 56° C. for DSC2.

The over-expression of DSC2 was found in lung cancer cell line NCI-H358 (FIG. 1A). In addition, to elucidate the efficacy of anti-DSC2 polyclonal antibody (BB049) on various cancers, the expression of DSC2 was confirmed. The over-expression of DSC2 was detected in colon cancer cell line HT-29, pancreatic cancer cell line KLM-1, prostate cancer cell line LNCap FGC, breast cancer cell line T47D, gastric cancer cell line MKN7, and liver cancer cell line HepG2 (FIG. 1B-G).

(4) Flow Cytometric Analysis

Cancer cells ($5\times10^6$) were incubated at 4° C. for 30 min with the purified polyclonal antibody (pAb: BB049), monoclonal antibodies (mAb), rabbit IgG (the control for pAb) or mouse IgG (the control for mAb). The cells were washed with phosphate buffer solution (PBS) and then incubated at 4° C. for 30 min in FITC-labeled Alexa Fluor 488. The cells were washed again in PBS, and analyzed on flow cytometer (FACSCalibur®, Becton Dickinson) and then analyzed by BD CellQuest™ Pro software (Becton Dickinson). Mean fluorescence intensity (MFI) was defined as a ratio of the flow cytometric intensity (intensity by each protein specific antibody/intensity by rabbit IgG).

Using DSC2 over-expressing cells, the binding proportions of anti-DSC2 antibodies on the cell surface were investigated. As a result, binding proportions of anti-DSC2 polyclonal antibody BB049 on NCI-H358, HT-29, KLM-1, LNCap FGC, T47D, MKN7, and HepG2 cell surfaces (MFI: 82.8, 56.8, 47.8, 15.8, 92.2, 51.8, and 20.7, respectively) were higher than that of rabbit IgG (control). Further, binding proportions of anti-DSC2 mouse monoclonal antibodies 48-5 and s10-4 on NCI-H358 cell surface (MFI: 10.0 and 11.1, respectively) were higher than that of mouse IgG (control), those of anti-DSC2 human-mouse chimeric antibodies ch48-5 and chs$10^{-4}$ on NCI-H358 cell surface (MFI: 34.3 and 54.8, respectively) were higher than that of mouse IgG (control), and those of anti-DSC2 human antibodies 332 and 545 on NCI-H358 cell surface (MFI: 9.48 and 5.52, respectively) were higher than that of human IgG (control).

(5) ADCC Assays

Target cells were exposed to 0.8 µM of calcein acetoxymethyl estel (Calcein-AM, DOJINDO) at 37° C. for 30 min. Calcein-AM becomes fluorescent after the cleavage of calcein-AM by cellular esterases that produce a fluorescent derivate calcein. Target cancer cells were washed twice before being added to the assay, and then plated on 96-well U-bottom plates ($4\times10^3$ cells/well). Human peripheral blood mononuclear cells (PMBC) were harvested from healthy person, separated using Ficoll-Paque (Amersham Biosciences) density gradient centrifugation, and then used as effector cells. Target cancer cells (T) and effector cells (E) were co-incubated in 250 µl of AIM-V medium in 96-well plates at various E:T ratios (200:1, 100:1, 50:1, 25:1, 12.5:1, and 6.25:1) with BB049 anti-DSC2 polyclonal antibody (2 µg/well) or control antibody Herceptin (2 µg/well, Roche). This incubation was carried out in triplicate, in 250 µL of AIM-V medium (Life Technologies, Inc), at 37° C. for six hrs. Control assays included the incubation of target cells with anti-DSC2 polyclonal antibody BB049 or effector cells alone. Herceptin was used as a control in some of the experiments.

The ADCC effects of anti-DSC2 polyclonal antibody (BB049) for these cells were evaluated based on the fluorescent images of viable cells that could be rapidly acquired using the IN Cell Analyzer 1000 (Amersham Bioscience). These images were numerically converted as viable cell counts (cell area for MKN7) by counting the fluorescent object or using Developer tool ver. 5.21 software (Amersham Bioscience).

Figure 2:
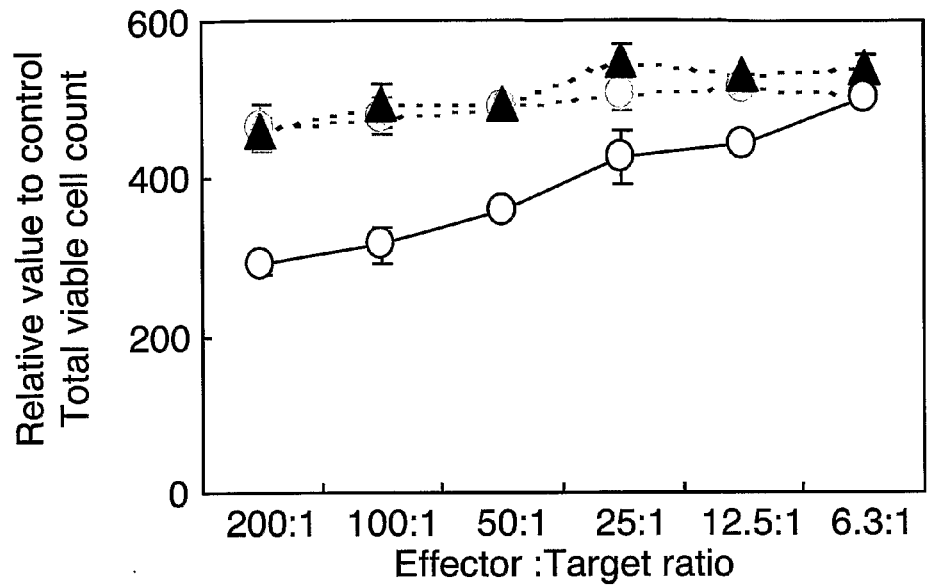
FIG. 2 depicts the results of ADCC assay using Herceptin against NCI-H358 over-expressed c-erbB-2 gene (A) and SK-LU-1 low-expressed c-erbB-2 gene (B).
Figure 2:
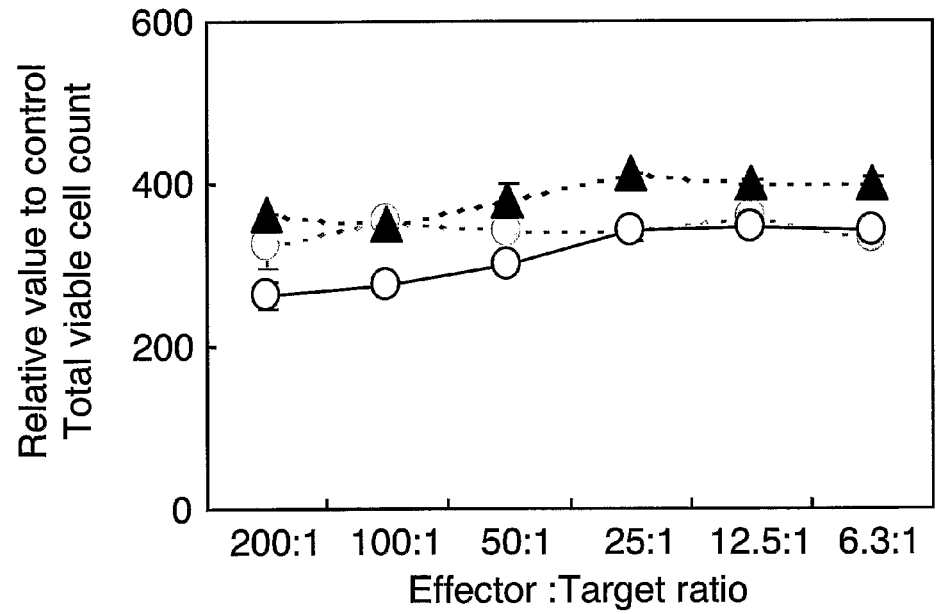
Figure 3:
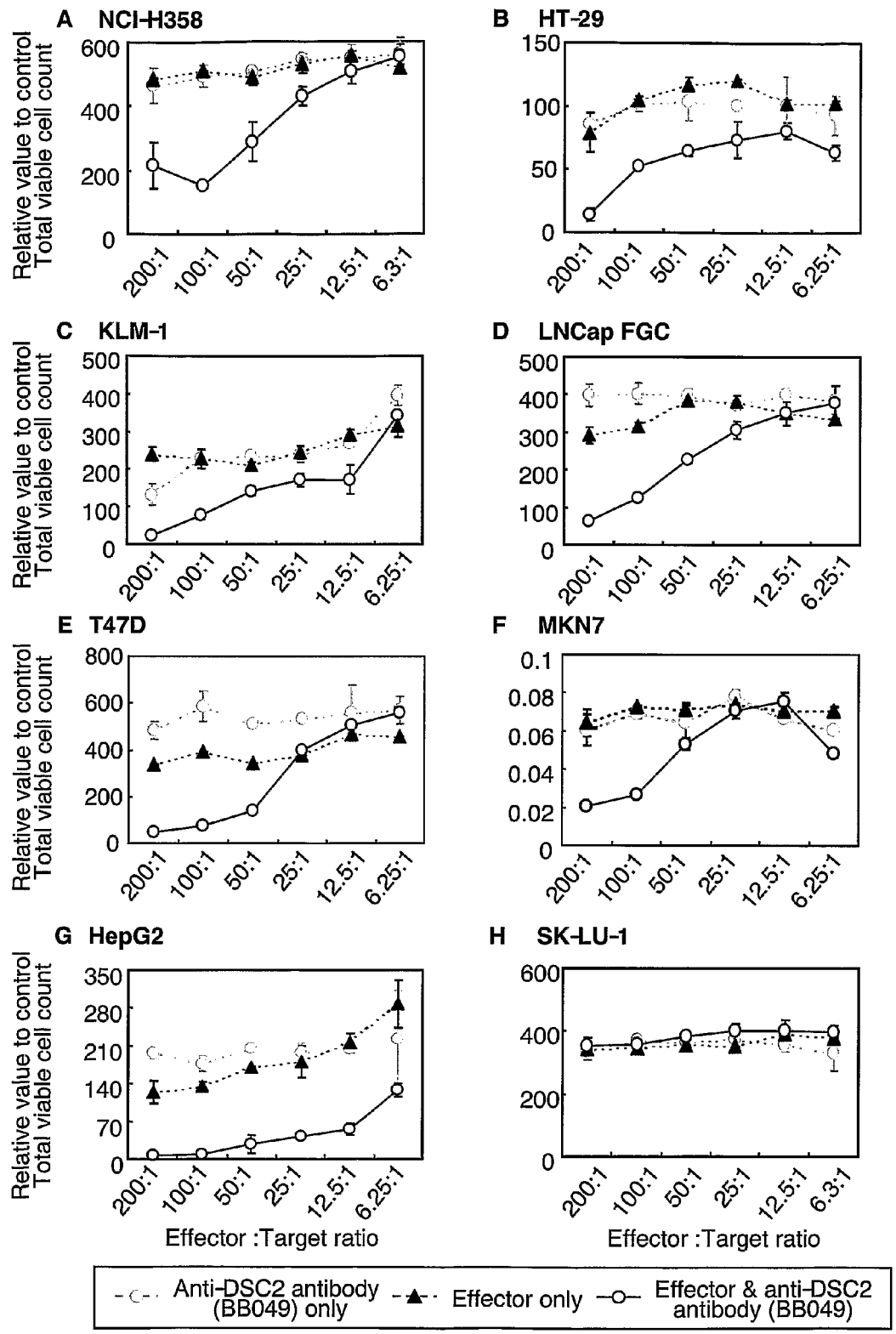
FIG. 3 depicts the results of ADCC assay using anti-DSC2 polyclonal antibodies BB049 against DSC2-over-expressing lung cancer cell line NCI-H358 (A), colon cancer cell line HT-29 (B), pancreatic cancer cell line KLM-1 (C), prostate cancer cell line LNCap FGC (D), breast cancer cell line T47D (E), gastric cancer cell line MKN-7 (F), and liver cancer cell line HepG2 (G), and DSC2-low-expressing lung cancer cell line SK-LU-1 (H), respectively.

Herceptin was used as a control in several experiments (FIGS. 2A and 2B). Direct cell damage of NCI-H358, HT-29, KLM-1, LNCap FGC, T47D, MKN7, and HepG2 cells by BB049 anti-DSC2 polyclonal antibody itself was not observed. However, BB049 induced ADCC in NCI-H358, HT-29, KLM-1, LNCap FGC, T47D, MKN7, and HepG2 cells that over-expressed DSC2 (FIG. 3A-G), while it caused no effect on SK-LU-1 cells with DSC2 low-expression (FIG. 3H).

Figure 4:
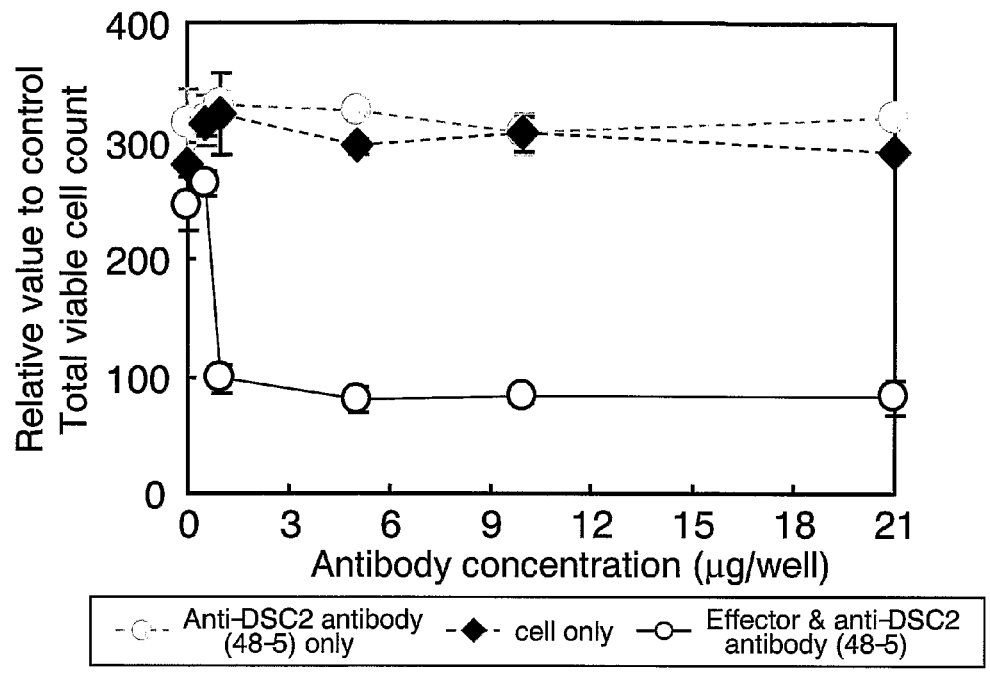
FIG. 4 depicts the results of ADCC assay using anti-DSC2 mouse monoclonal antibody 48-5 (A) and antibody s10-4 against DSC2-over-expressing lung cancer cell line NCI-H358 (B).
Figure 4:
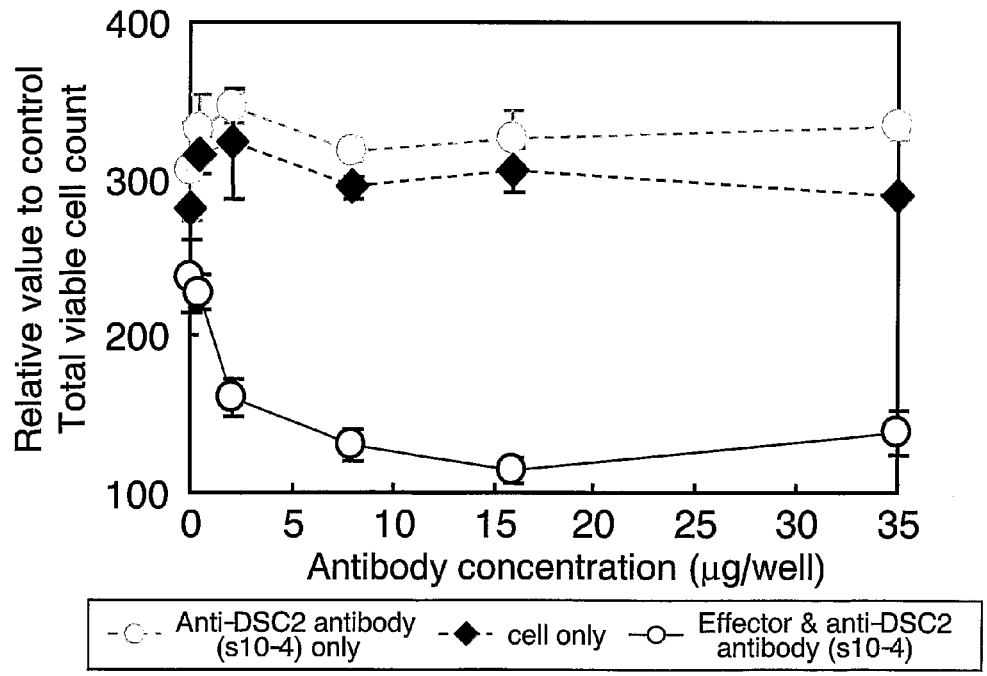

The ADCC effects of anti-DSC2 mouse monoclonal antibodies 48-5 and s10-4 on DSC2 over-expressing cell line NCI-H358 were estimated. As described above, target and effector cells were prepared. Under the condition at an E:T ratio of 100:1, at various concentrations (0, 0.5, 1.0, 5.0, 10.0, and 21.0 µg/well for 48-5; and 0, 0.5, 2.0, 8.0, 16.0, and 35.0 µg/well for s10-4), 48-5 and s10-4 induced ADCC in NCI- H358 cells (FIG. 4). No direct cell damage of NCI-H358 cells by anti-DSC2 monoclonal antibodies (48-5 and s10-4) was observed.

Figure 5:
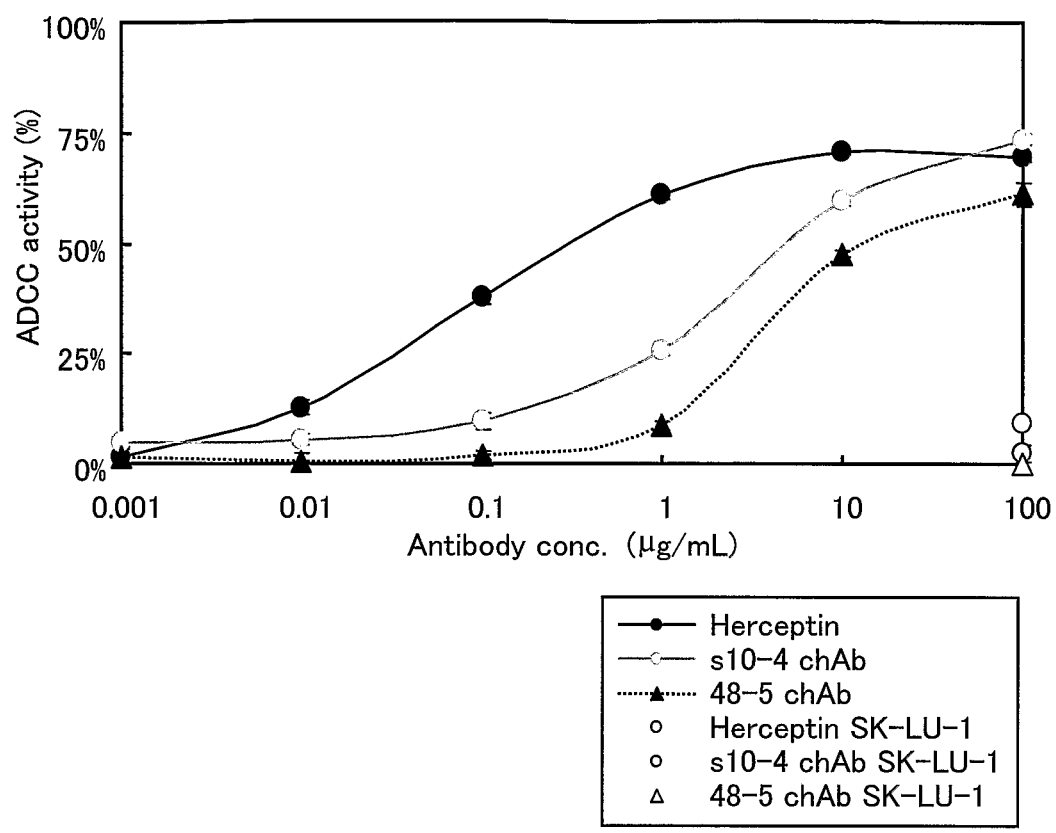
FIG. 5 depicts the results of ADCC assay using Herceptin and anti-DSC2 human-mouse chimeric antibodies ch48-5 and s10-4 against DSC2-over- and DSC2-low-expressing lung cancer cell lines, NCI-H358 and SK-LU-1, respectively.

The ADCC effects of anti-DSC2 human-mouse chimeric antibodies ch48-5 and chs10-4 on DSC2 over-expressing cell line NCI-H358 were estimated. As above, target and effector cells were prepared. Under the condition at an E:T ratio of 100:1, at various concentrations (0, 0.05, 0.1, 5.0, and 0.15 µg/well), ch48-5 and chs10-4 induced ADCC in NCI-H358 cells (FIG. 5). No direct cell damage of NCI-H358 cells by anti-DSC2 human-mouse chimeric antibodies (ch48-5 and chs10-4) was observed.

Figure 6:
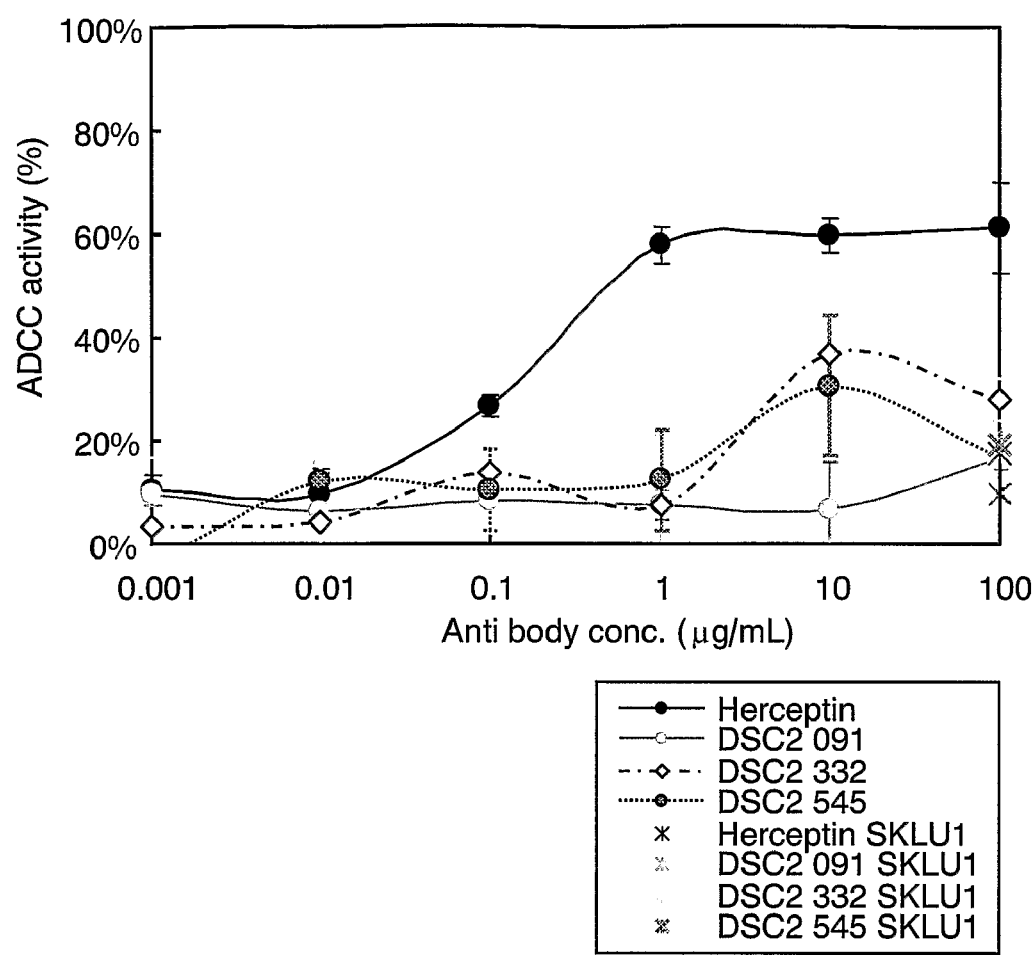
FIG. 6 depicts the results of ADCC assay using Herceptin and anti-DSC2 human antibodies 332 and 545 against DSC2-over- and DSC2-low-expressing lung cancer cell lines NCI-H358 and SK-LU-1, respectively.

The ADCC effects of anti-DSC2 human antibodies 332 and 545 on DSC2 over-expressing cell line NCI-H358 were estimated. As above, target and effector cells were prepared. Under the condition at an E:T ratio of 100:1, at various concentrations (0.001, 0.01, 0.1, 1.0, 10, and 100 µg/well), 332 and 545 induced ADCC in NCI-H358 cells (FIG. 6). No direct cell damage of NCI-H358 cells by anti-DSC2 human antibodies (332 and 545) was observed.

INDUSTRIAL APPLICABILITY

The present invention is based, at least in part, on the discovery that DSC2-expressing cells can be damaged by utilizing the cytotoxicity of antibodies. Strong expression of DSC2 gene was identified by the present inventors in lung, colon, pancreatic, prostate, breast, gastric and liver cancers. Herein, results demonstrating the effect of antibody dependent cell-mediated cytotoxicity (ADCC) of anti-DSC2 antibodies on lung, colon, pancreatic, prostate, breast, gastric and liver cancer cell lines are presented. Thus, the antibodies, compositions and methods of the present invention provide a novel approach for treating diseases associated with DSC2-expression, for example, lung, colon, pancreatic, prostate, breast, gastric and liver cancers.

While the invention has been described in detail with reference to specific embodiments thereof, it will be apparent to those skilled in the art that various changes and modifications can be made therein without departing from the spirit and scope of the invention, the metes and bounds of which are set by the appended claims.

The invention claimed is:

1. An isolated antibody against desmocollin 2 (DSC2) showing effector function, wherein the antibody comprises complementarity determining regions (CDRs) selected from the group consisting of:

group 1:
FSSFGMH (SEQ ID NO: 26) as VH CDR1,

YISSGSSTIYYADTVK (SEQ ID NO: 27) as VH CDR2, and

VHYYYFDY (SEQ ID NO: 28) as VH CDR3;

KASQDINKYIA (SEQ ID NO: 29) as VL CDR1,

YTSTLQP (SEQ ID NO: 30) as VL CDR2, and

LQYDNLW (SEQ ID NO: 31) as VL CDR3;

group 2:
DYSMH (SEQ ID NO: 32) as VH CDR1,

WINTETGEPTYADDFKG (SEQ ID NO: 33) as VH CDR2, and

WLLFDY (SEQ ID NO: 34) as VH CDR3;

KSSQSLLNSSNQKNYLA (SEQ ID NO: 35) as VL CDR1,

FASTRES (SEQ ID NO: 36) as VL CDR2, and

QQHYSTPL (SEQ ID NO: 37) as VL CDR3;

group 3:
GNYWS (SEQ ID NO: 39) as VH CDR1,

EINHSGNTKYNPSLKS (SEQ ID NO: 40) as VH CDR2, and

VPFDWFHPPGEPPFYYYYGMDV (SEQ ID NO: 41) as VH CDR3;

TGSSSNIGAGYDVH (SEQ ID NO: 44) as VL CDR1,

GNSNRPS (SEQ ID NO: 45) as VL CDR2, and

QSYDSSLSGWV (SEQ ID NO: 46) as VL CDR3;

group 4:
GYFWS (SEQ ID NO: 49) as VH CDR1,

EINHSGSTSYNPSLKS (SEQ ID NO: 50) as VH CDR2, and

GQGYYSSLDP (SEQ ID NO: 51) as VH CDR3; and

SGSSSNIGSNTVN (SEQ ID NO: 53) as VL CDR1,

SNNQRPS (SEQ ID NO: 54) as VL CDR2, and

AAWDDSLNGVV (SEQ ID NO: 55) as VL CDR3; and wherein the CDR1, CDR2, and CDR3 are separated by framework amino acid sequences.

2. The antibody of claim 1, which is a monoclonal antibody.

3. The antibody of claim 1, which is IgG1.

4. The antibody of claim 1, wherein the effector function is either antibody-dependent cytotoxicity, complement-dependent cytotoxicity, or both.

5. A composition for damaging DSC2-expressing cells, which composition comprises as an active ingredient the antibody of claim 1 or a polynucleotide encoding the antibody.

6. The composition of claim 5, wherein the DSC2-expressing cells are selected from the group of lung, colon, pancreatic, prostate, breast, gastric or liver cancer cells.

7. The composition of claim 5, wherein the antibody is a monoclonal antibody.

8. The composition of claim 5, wherein the antibody is IgG1.

9. The composition of claim 5, wherein the antibody effector function is either antibody-dependent cytotoxicity, complement-dependent cytotoxicity, or both.

10. The composition of claim 5, wherein the polynucleotide is contained in a vector.

11. A method for damaging DSC2-expressing cells, comprising the steps of:
a) contacting DSC2-expressing cells with the antibody of claim 1; and b) damaging the DSC2-expressing cells through the effector function of the antibody that bound to the cell.

12. A pharmaceutical composition for damaging DSC2-expressing cells, which composition comprises as an active ingredient the antibody of claim 1.

13. The pharmaceutical composition of claim 12, wherein the DSC2-expressing cells are selected from the group of lung, colon, pancreatic, prostate, breast, gastric or liver cancer cells.

14. The pharmaceutical composition of claim 12, wherein the antibody is a monoclonal antibody.

15. The pharmaceutical composition of claim 12, wherein the antibody is IgG1.

16. The pharmaceutical composition of claim 12, wherein the antibody effector function is either antibody-dependent cytotoxicity, complement-dependent cytotoxicity, or both.

* * * * *

UNITED STATES PATENT AND TRADEMARK OFFICE
Certificate

Patent No. 7,786,266 B2              Patented: August 31, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Shuichi Nakatsuru, Kawasaki (JP); Takashi Iwamoto, Kawasaki (JP); Megumi Yoshikawa, Kawasaki (JP); Ken-ichiro Ono, Aichi (JP); and Harue Katsumi, Aichi (JP).

Signed and Sealed this Twenty-fifth Day of October 2011.

Misook Yu
*Supervisory Patent Examiner*
Art Unit 1642
Technology Center 1600

SEQUENCE LISTING

<160> NUMBER OF SEQ ID NOS: 86

<210> SEQ ID NO 1
<211> LENGTH: 5186
<212> TYPE: DNA
<213> ORGANISM: Homo sapiens
<220> FEATURE:
<221> NAME/KEY: CDS
<222> LOCATION: (444)..(2984)

<400> SEQUENCE: 1

```
gcttctgctg ggcagggccg gctgttaatc tcgcctggcg gagcggacac cggggcgtgg      60
tgggggagat gggccttata ggtggcgtcc gctggtgaga aacaccttgc gcaggtaaaa     120
gggtggcggc gagagggagt tcccacccgt ggctttctta gagaaatgaa gtcttaagtc     180
ttaaatagac aacaaggagg ggccgatcgg tgtcttttgg acgcgtctgg agccctccc     240 tccgccaaag gaaaagcccc ttggatgaga ggcaggcgct tcagagaagc taagaaaagc     300
acctctccgc gcgccccacc tcctccgcct cgcgctcctc ctgagcagcg ggcccagact     360
gcgctccggc cgcggccctc gccccgcgga gccctcctac cccggcccga cgctcggccc     420
gcgacctgcc ccgagccctc tcc atg gag gca gcc cgc ccc tcc ggc tcc tgg    473
                        Met Glu Ala Ala Arg Pro Ser Gly Ser Trp
                         1               5                  10 aac gga gcc ctc tgc cgg ctg ctc ctg ctg acc ctc gcg atc tta ata       521
Asn Gly Ala Leu Cys Arg Leu Leu Leu Leu Thr Leu Ala Ile Leu Ile
                 15                  20                  25 ttt gcc agt gat gcc tgc aaa aat gtg aca tta cat gtt ccc tcc aaa       569
Phe Ala Ser Asp Ala Cys Lys Asn Val Thr Leu His Val Pro Ser Lys
             30                  35                  40 cta gat gcc gag aaa ctt gtt ggt aga gtt aac ctg aaa gag tgc ttt       617
Leu Asp Ala Glu Lys Leu Val Gly Arg Val Asn Leu Lys Glu Cys Phe
         45                  50                  55 aca gct gca aat cta att cat tca agt gat cct gac ttc caa att ttg      665
Thr Ala Ala Asn Leu Ile His Ser Ser Asp Pro Asp Phe Gln Ile Leu
```

-continued

```
              60                  65                  70
gag gat ggt tca gtc tat aca aca aat act att cta ttg tcc tcg gag      713
Glu Asp Gly Ser Val Tyr Thr Thr Asn Thr Ile Leu Leu Ser Ser Glu
 75              80                  85                  90 aag aga agt ttt acc ata tta ctt tcc aac act gag aac caa gaa aag      761
Lys Arg Ser Phe Thr Ile Leu Leu Ser Asn Thr Glu Asn Gln Glu Lys
                 95                 100                 105 aag aaa ata ttt gtc ttt ttg gag cat caa aca aag gtc cta aag aaa      809
Lys Lys Ile Phe Val Phe Leu Glu His Gln Thr Lys Val Leu Lys Lys
            110                 115                 120 aga cat act aaa gaa aaa gtt cta agg cgc gcc aag aga aga tgg gct      857
Arg His Thr Lys Glu Lys Val Leu Arg Arg Ala Lys Arg Arg Trp Ala
                125                 130                 135 cca att cct tgt tcg atg cta gaa aac tcc ttg ggt cct ttt cca ctt      905
Pro Ile Pro Cys Ser Met Leu Glu Asn Ser Leu Gly Pro Phe Pro Leu
140                 145                 150 ttc ctt caa cag gtt caa tct gac acg gcc caa aac tat acc ata tac      953
Phe Leu Gln Gln Val Gln Ser Asp Thr Ala Gln Asn Tyr Thr Ile Tyr
155                 160                 165                 170 tat tcc ata aga ggt cct gga gtt gac caa gaa cct cgg aat tta ttt     1001
Tyr Ser Ile Arg Gly Pro Gly Val Asp Gln Glu Pro Arg Asn Leu Phe
                175                 180                 185 tat gtg gag aga gac act gga aac ttg tat tgt act cgt cct gta gat     1049
Tyr Val Glu Arg Asp Thr Gly Asn Leu Tyr Cys Thr Arg Pro Val Asp
            190                 195                 200 cgt gag cag tat gaa tct ttt gag ata att gcc ttt gca aca act cca     1097
Arg Glu Gln Tyr Glu Ser Phe Glu Ile Ile Ala Phe Ala Thr Thr Pro
        205                 210                 215 gat ggg tat act cca gaa ctt cca ctg ccc cta ata atc aaa ata gag     1145
Asp Gly Tyr Thr Pro Glu Leu Pro Leu Pro Leu Ile Ile Lys Ile Glu
220                 225                 230 gat gaa aat gat aac tac cca att ttt aca gaa gaa act tat act ttt     1193
Asp Glu Asn Asp Asn Tyr Pro Ile Phe Thr Glu Glu Thr Tyr Thr Phe
235                 240                 245                 250 aca att ttt gaa aat tgc aga gtg ggc act act gtg gga caa gtg tgt     1241
Thr Ile Phe Glu Asn Cys Arg Val Gly Thr Thr Val Gly Gln Val Cys
                255                 260                 265 gct act gac aaa gat gag cct gac acg atg cac aca cgc ctg aag tac     1289
Ala Thr Asp Lys Asp Glu Pro Asp Thr Met His Thr Arg Leu Lys Tyr
            270                 275                 280 tcc atc att ggg cag gtg cca cca tca ccc acc cta ttt tct atg cat     1337
Ser Ile Ile Gly Gln Val Pro Pro Ser Pro Thr Leu Phe Ser Met His
        285                 290                 295 cca act aca ggc gtg atc acc aca aca tca tct cag cta gac aga gag     1385
Pro Thr Thr Gly Val Ile Thr Thr Thr Ser Ser Gln Leu Asp Arg Glu
300                 305                 310 tta att gac aag tac cag ttg aaa ata aaa gta caa gac atg gat ggt     1433
Leu Ile Asp Lys Tyr Gln Leu Lys Ile Lys Val Gln Asp Met Asp Gly
315                 320                 325                 330 cag tat ttt ggt cta cag aca act tca act tgt atc att aac att gat     1481
Gln Tyr Phe Gly Leu Gln Thr Thr Ser Thr Cys Ile Ile Asn Ile Asp
                335                 340                 345 gat gta aat gac cac ttg cca aca ttt act cgt act tct tat gtg aca     1529
Asp Val Asn Asp His Leu Pro Thr Phe Thr Arg Thr Ser Tyr Val Thr
            350                 355                 360 tca gtg gaa gaa aat aca gtt gat gtg gaa atc tta cga gtt act gtt     1577
Ser Val Glu Glu Asn Thr Val Asp Val Glu Ile Leu Arg Val Thr Val
        365                 370                 375 gag gat aag gac tta gtg aat act gct aac tgg aga gct aat tat acc     1625
```

```
Glu Asp Lys Asp Leu Val Asn Thr Ala Asn Trp Arg Ala Asn Tyr Thr
    380                 385                 390 att tta aag ggc aat gaa aat ggc aat ttt aaa att gta aca gat gcc     1673
Ile Leu Lys Gly Asn Glu Asn Gly Asn Phe Lys Ile Val Thr Asp Ala
395                 400                 405                 410 aaa acc aat gaa gga gtt ctt tgt gta gtt aag cct ttg aat tat gaa     1721
Lys Thr Asn Glu Gly Val Leu Cys Val Val Lys Pro Leu Asn Tyr Glu
                415                 420                 425 gaa aag caa cag atg atc ttg caa att ggt gta gtt aat gaa gct cca     1769
Glu Lys Gln Gln Met Ile Leu Gln Ile Gly Val Val Asn Glu Ala Pro
            430                 435                 440 ttt tcc aga gag gct agt cca aga tca gcc atg agc aca gca aca gtt     1817
Phe Ser Arg Glu Ala Ser Pro Arg Ser Ala Met Ser Thr Ala Thr Val
        445                 450                 455 act gtt aat gta gaa gat cag gat gag ggc cct gag tgt aac cct cca     1865
Thr Val Asn Val Glu Asp Gln Asp Glu Gly Pro Glu Cys Asn Pro Pro
    460                 465                 470 ata cag act gtt cgc atg aaa gaa aat gca gaa gtg gga aca aca agc     1913
Ile Gln Thr Val Arg Met Lys Glu Asn Ala Glu Val Gly Thr Thr Ser
475                 480                 485                 490 aat gga tat aaa gca tat gac cca gaa aca aga agt agc agt ggc ata     1961
Asn Gly Tyr Lys Ala Tyr Asp Pro Glu Thr Arg Ser Ser Ser Gly Ile
                495                 500                 505 agg tat aag aaa tta act gat cca aca ggg tgg gtc acc att gat gaa     2009
Arg Tyr Lys Lys Leu Thr Asp Pro Thr Gly Trp Val Thr Ile Asp Glu
            510                 515                 520 aat aca gga tca atc aaa gtt ttc aga agc ctg gat aga gag gca gag     2057
Asn Thr Gly Ser Ile Lys Val Phe Arg Ser Leu Asp Arg Glu Ala Glu
        525                 530                 535 acc atc aaa aat ggc ata tat aat att aca gtc ctt gca tca gac caa     2105
Thr Ile Lys Asn Gly Ile Tyr Asn Ile Thr Val Leu Ala Ser Asp Gln
    540                 545                 550 gga ggg aga aca tgt acg ggg aca ctg ggc att ata ctt caa gac gtg     2153
Gly Gly Arg Thr Cys Thr Gly Thr Leu Gly Ile Ile Leu Gln Asp Val
555                 560                 565                 570 aat gat aac agc cca ttc ata cct aaa aag aca gtg atc atc tgc aaa     2201
Asn Asp Asn Ser Pro Phe Ile Pro Lys Lys Thr Val Ile Ile Cys Lys
                575                 580                 585 ccc acc atg tca tct gcg gag att gtt gcg gtt gat cct gat gag cct     2249
Pro Thr Met Ser Ser Ala Glu Ile Val Ala Val Asp Pro Asp Glu Pro
            590                 595                 600 atc cat ggc cca ccc ttt gac ttt agt ctg gag agt tct act tca gaa     2297
Ile His Gly Pro Pro Phe Asp Phe Ser Leu Glu Ser Ser Thr Ser Glu
        605                 610                 615 gta cag aga atg tgg aga ctg aaa gca att aat gat aca gca gca cgt     2345
Val Gln Arg Met Trp Arg Leu Lys Ala Ile Asn Asp Thr Ala Ala Arg
    620                 625                 630 ctt tcc tat cag aat gat cct cca ttt ggc tca tat gta gta cct ata     2393
Leu Ser Tyr Gln Asn Asp Pro Pro Phe Gly Ser Tyr Val Val Pro Ile
635                 640                 645                 650 aca gtg aga gat aga ctt ggc atg tct agt gtc act tca ttg gat gtt     2441
Thr Val Arg Asp Arg Leu Gly Met Ser Ser Val Thr Ser Leu Asp Val
                655                 660                 665 aca ctg tgt gac tgc att acc gaa aat gac tgc aca cat cgt gta gat     2489
Thr Leu Cys Asp Cys Ile Thr Glu Asn Asp Cys Thr His Arg Val Asp
            670                 675                 680 cca agg att ggc ggt gga gga gta caa ctt gga aag tgg gcc atc ctt     2537
Pro Arg Ile Gly Gly Gly Gly Val Gln Leu Gly Lys Trp Ala Ile Leu
        685                 690                 695
```

```
gca ata ttg ttg ggc ata gca ttg ctc ttt tgc atc ctg ttt acg ctg    2585
Ala Ile Leu Leu Gly Ile Ala Leu Leu Phe Cys Ile Leu Phe Thr Leu
    700                 705                 710 gtc tgt ggg gct tct ggg acg tct aaa caa cca aaa gta att cct gat    2633
Val Cys Gly Ala Ser Gly Thr Ser Lys Gln Pro Lys Val Ile Pro Asp
715                 720                 725                 730 gat tta gcc cag cag aac cta att gta tca aac aca gaa gct cct gga    2681
Asp Leu Ala Gln Gln Asn Leu Ile Val Ser Asn Thr Glu Ala Pro Gly
                735                 740                 745 gat gac aaa gtg tat tct gcg aat ggc ttc aca acc caa act gtg ggc    2729
Asp Asp Lys Val Tyr Ser Ala Asn Gly Phe Thr Thr Gln Thr Val Gly
            750                 755                 760 gct tct gct cag gga gtt tgt ggc acc gtg gga tca gga atc aaa aac    2777
Ala Ser Ala Gln Gly Val Cys Gly Thr Val Gly Ser Gly Ile Lys Asn
        765                 770                 775 gga ggt cag gag acc atc gaa atg gtg aaa gga gga cac cag acc tcg    2825
Gly Gly Gln Glu Thr Ile Glu Met Val Lys Gly Gly His Gln Thr Ser
    780                 785                 790 gaa tcc tgc cgg ggg gct ggc cac cat cac acc ctg gac tcc tgc agg    2873
Glu Ser Cys Arg Gly Ala Gly His His His Thr Leu Asp Ser Cys Arg
795                 800                 805                 810 gga gga cac acg gag gtg gac aac tgc aga tac act tac tcg gag tgg    2921
Gly Gly His Thr Glu Val Asp Asn Cys Arg Tyr Thr Tyr Ser Glu Trp
                815                 820                 825 cac agt ttt act cag ccc cgt ctt ggt gaa gaa tcc att aga gga cac    2969
His Ser Phe Thr Gln Pro Arg Leu Gly Glu Glu Ser Ile Arg Gly His
            830                 835                 840 act ctg att aaa aat taaacaatga agaaagtgt atctgtgtaa tcaagatgaa    3024
Thr Leu Ile Lys Asn
        845 aatcacaagc atgcccaaga ctatgtcctg acatataact atgaaggaag aggatcggtg    3084 gctgggtctg taggttgttg cagtgaacga caagaagaag atgggcttga attttttggat   3144 aatttggagc ccaaatttag acactagca gaagcatgca tgaagagatg agtgtgttct    3204 aataagtctc tgaaagccag tggctttatg acttttaaaa aaaattacaa accaagaatt    3264 ttttaaagca gaagatgcta tttgtggggg ttttctctc attatttgga tggaatctct    3324 ttggtcaaat gcacatttac agagagacac tataaacaag tacacaaatt tttcaatttt    3384 tacatatttt taaattactt atcttctatc caaggaggtc tacagagaaa ttaaagtctg    3444 ccttatttgt tacatttggg tataatgaca acagccaatt tatagtgcaa taaaatgtaa    3504 ttaattcaag tccttattat agactatttg aagcacaacc taatgaaaaa ttgtagagac    3564 cttgctttaa cattatctcc agttaattaa gtgttcatgt ggtgcttgga aactgttgtt    3624 ttcctgaaca tctaaagtgt gtagactgca ttcttgctat tattttattc ttgtaatgtg    3684 acctttttcac tgtgcaaagg gagatttcta gccaggcatt gactattaca atttcattt     3744 ggtggagttt agttttaggt tttattgtat ataaatcct gcactgaatc tgtgtctcct     3804 ctgttaccta cttttgccag tgaaatttaa gttttaaaat acttcagaa tgtatttta     3864 ctactgcaag ttttggtct ttaaaatgtc aagtagcatc tctctctttc tctctgtctc    3924 tttctgtttc tctctccagt tttttttttt ttttaatttt ccatatgggc taaagaatcc    3984 aaatatttta aaaatctgtc tctcttttct tctctcataa agtgaattat tccttttttt    4044 tgttttatgt aagtgtatat attcttagtt tttcttgaaa tcattgtaat gttaactttg    4104 ttgtttcaaa tatcttggtg attgcttcat tatctcttca acaaaaaaaa cctttaattt    4164 tgccattgaa actgtagaac tatgccatgc ttttattaga agcagtgctc tgtgttaaca    4224
```

-continued

```
acaagaatgg tgtaattaga attgggatgt ggatatttac tgtatgacaa cacatttaca    4284
gttctgtaat gcaaggatgc agtttaaaaa tgtgaagtag tgatggtttt tgaaataagc    4344
tttaaaatat agggatcttg aaggctccct ggggtaacta ttttataact tagataaaat    4404
ggctagtcat atctgtgtgt tgtaaagtt attttttaa tattttaaga ttacaatttt      4464
aacaaatgta gaaatgagcc aaactattta aattttaaaa cagtaaaaca aaatgaaact    4524
taatagctca caaaattcca gtccatgttt catgacttat tttagtcaat gaattttcta    4584
tttatactaa acatatggac attttaaatg tgtttctaat attttgatt atctataatg     4644 tgcctgtctt caattcacaa gattgggtta taacaattat ttgccagatt aacactaggg    4704
aattatttga taaccagctt atcttatcag tagtttatt gctgatcagg caaaaatagt     4764
tttccaaagt tatttttaat aaagtatata caaaattctt atatattact agtcatgata    4824
aagtaaatta agcagttttt aaaacttagt gtgagtttgt tcatcacagg tctgatatga    4884
gtttaaggga tttcgcactc cctgaatcag agaagtaaga ccccttcctt agattcctgt    4944
tatacatttt ttaaaatgta gagtttgttt tggagacatt ttcagtgcat tgttattgcc    5004
atatttatat aatatgacta ttctaaaggc tgtgaggcca tggggtattg gttaagttgc    5064
ttgcttttgc tttgtccatt ttcatcattt taaaatgggg gataataaca gaacttgttt    5124
cctagggcca ttgtaagtca cttgaataaa aaatagtttt gaagcaaaaa aaaaaaaaaa    5184
aa                                                                   5186
```

<210> SEQ ID NO 2
<211> LENGTH: 847
<212> TYPE: PRT
<213> ORGANISM: Homo sapiens

<400> SEQUENCE: 2

```
Met Glu Ala Ala Arg Pro Ser Gly Ser Trp Asn Gly Ala Leu Cys Arg
1               5                   10                  15

Leu Leu Leu Leu Thr Leu Ala Ile Leu Ile Phe Ala Ser Asp Ala Cys
            20                  25                  30

Lys Asn Val Thr Leu His Val Pro Ser Lys Leu Asp Ala Glu Lys Leu
        35                  40                  45

Val Gly Arg Val Asn Leu Lys Glu Cys Phe Thr Ala Ala Asn Leu Ile
    50                  55                  60

His Ser Ser Asp Pro Asp Phe Gln Ile Leu Glu Asp Gly Ser Val Tyr
65                  70                  75                  80

Thr Thr Asn Thr Ile Leu Leu Ser Ser Glu Lys Arg Ser Phe Thr Ile
                85                  90                  95

Leu Leu Ser Asn Thr Glu Asn Gln Glu Lys Lys Lys Ile Phe Val Phe
            100                 105                 110

Leu Glu His Gln Thr Lys Val Leu Lys Lys Arg His Thr Lys Glu Lys
        115                 120                 125

Val Leu Arg Arg Ala Lys Arg Arg Trp Ala Pro Ile Pro Cys Ser Met
    130                 135                 140

Leu Glu Asn Ser Leu Gly Pro Phe Pro Leu Phe Leu Gln Gln Val Gln
145                 150                 155                 160

Ser Asp Thr Ala Gln Asn Tyr Thr Ile Tyr Tyr Ser Ile Arg Gly Pro
                165                 170                 175

Gly Val Asp Gln Glu Pro Arg Asn Leu Phe Tyr Val Glu Arg Asp Thr
            180                 185                 190
```

```
Gly Asn Leu Tyr Cys Thr Arg Pro Val Asp Arg Glu Gln Tyr Glu Ser
            195                 200                 205

Phe Glu Ile Ile Ala Phe Ala Thr Thr Pro Asp Gly Tyr Thr Pro Glu
210                 215                 220

Leu Pro Leu Pro Leu Ile Ile Lys Ile Glu Asp Glu Asn Asp Asn Tyr
225                 230                 235                 240

Pro Ile Phe Thr Glu Glu Thr Tyr Thr Phe Thr Ile Phe Glu Asn Cys
            245                 250                 255

Arg Val Gly Thr Thr Val Gly Gln Val Cys Ala Thr Asp Lys Asp Glu
            260                 265                 270

Pro Asp Thr Met His Thr Arg Leu Lys Tyr Ser Ile Ile Gly Gln Val
            275                 280                 285

Pro Pro Ser Pro Thr Leu Phe Ser Met His Pro Thr Thr Gly Val Ile
            290                 295                 300

Thr Thr Thr Ser Ser Gln Leu Asp Arg Glu Leu Ile Asp Lys Tyr Gln
305                 310                 315                 320

Leu Lys Ile Lys Val Gln Asp Met Asp Gly Gln Tyr Phe Gly Leu Gln
            325                 330                 335

Thr Thr Ser Thr Cys Ile Ile Asn Ile Asp Asp Val Asn Asp His Leu
            340                 345                 350

Pro Thr Phe Thr Arg Thr Ser Tyr Val Thr Ser Val Glu Glu Asn Thr
            355                 360                 365

Val Asp Val Glu Ile Leu Arg Val Thr Val Glu Asp Lys Asp Leu Val
            370                 375                 380

Asn Thr Ala Asn Trp Arg Ala Asn Tyr Thr Ile Leu Lys Gly Asn Glu
385                 390                 395                 400

Asn Gly Asn Phe Lys Ile Val Thr Asp Ala Lys Thr Asn Glu Gly Val
            405                 410                 415

Leu Cys Val Val Lys Pro Leu Asn Tyr Glu Glu Lys Gln Gln Met Ile
            420                 425                 430

Leu Gln Ile Gly Val Val Asn Glu Ala Pro Phe Ser Arg Glu Ala Ser
            435                 440                 445

Pro Arg Ser Ala Met Ser Thr Ala Thr Val Thr Val Asn Val Glu Asp
            450                 455                 460

Gln Asp Glu Gly Pro Glu Cys Asn Pro Pro Ile Gln Thr Val Arg Met
465                 470                 475                 480

Lys Glu Asn Ala Glu Val Gly Thr Thr Ser Asn Gly Tyr Lys Ala Tyr
            485                 490                 495

Asp Pro Glu Thr Arg Ser Ser Ser Gly Ile Arg Tyr Lys Lys Leu Thr
            500                 505                 510

Asp Pro Thr Gly Trp Val Thr Ile Asp Glu Asn Thr Gly Ser Ile Lys
            515                 520                 525

Val Phe Arg Ser Leu Asp Arg Glu Ala Glu Thr Ile Lys Asn Gly Ile
            530                 535                 540

Tyr Asn Ile Thr Val Leu Ala Ser Asp Gln Gly Gly Arg Thr Cys Thr
545                 550                 555                 560

Gly Thr Leu Gly Ile Ile Leu Gln Asp Val Asn Asp Asn Ser Pro Phe
            565                 570                 575

Ile Pro Lys Lys Thr Val Ile Cys Lys Pro Thr Met Ser Ser Ala
            580                 585                 590

Glu Ile Val Ala Val Asp Pro Asp Glu Pro Ile His Gly Pro Pro Phe
            595                 600                 605

Asp Phe Ser Leu Glu Ser Ser Thr Ser Glu Val Gln Arg Met Trp Arg
```

-continued

|  | 610 |  | 615 |  | 620 |  |
|---|---|---|---|---|---|---|

Leu Lys Ala Ile Asn Asp Thr Ala Ala Arg Leu Ser Tyr Gln Asn Asp
625                 630                 635                 640

Pro Pro Phe Gly Ser Tyr Val Val Pro Ile Thr Val Arg Asp Arg Leu
            645                 650                 655

Gly Met Ser Ser Val Thr Ser Leu Asp Val Thr Leu Cys Asp Cys Ile
        660                 665                 670

Thr Glu Asn Asp Cys Thr His Arg Val Asp Pro Arg Ile Gly Gly Gly
    675                 680                 685

Gly Val Gln Leu Gly Lys Trp Ala Ile Leu Ala Ile Leu Leu Gly Ile
690                 695                 700

Ala Leu Leu Phe Cys Ile Leu Phe Thr Leu Val Cys Gly Ala Ser Gly
705                 710                 715                 720

Thr Ser Lys Gln Pro Lys Val Ile Pro Asp Asp Leu Ala Gln Gln Asn
            725                 730                 735

Leu Ile Val Ser Asn Thr Glu Ala Pro Gly Asp Asp Lys Val Tyr Ser
        740                 745                 750

Ala Asn Gly Phe Thr Thr Gln Thr Val Gly Ala Ser Ala Gln Gly Val
    755                 760                 765

Cys Gly Thr Val Gly Ser Gly Ile Lys Asn Gly Gly Gln Glu Thr Ile
770                 775                 780

Glu Met Val Lys Gly Gly His Gln Thr Ser Glu Ser Cys Arg Gly Ala
785                 790                 795                 800

Gly His His His Thr Leu Asp Ser Cys Arg Gly His Thr Glu Val
            805                 810                 815

Asp Asn Cys Arg Tyr Thr Tyr Ser Glu Trp His Ser Phe Thr Gln Pro
            820                 825                 830

Arg Leu Gly Glu Glu Ser Ile Arg Gly His Thr Leu Ile Lys Asn
        835                 840                 845

<210> SEQ ID NO 3
<211> LENGTH: 5140
<212> TYPE: DNA
<213> ORGANISM: Homo sapiens
<220> FEATURE:
<221> NAME/KEY: CDS
<222> LOCATION: (444)..(3146)

<400> SEQUENCE: 3
gcttctgctg ggcagggccg gctgttaatc tcgcctggcg gagcggacac cggggcgtgg      60
tgggggagat gggccttata ggtggcgtcc gctggtgaga acaccttgc gcaggtaaaa      120 gggtggcggc gagagggagt tcccacccgt ggctttctta gagaaatgaa gtcttaagtc      180
ttaaatagac aacaaggagg ggccgatcgg tgtcttttgg acgcgtctgg agcccctccc      240
tccgccaaag gaaagccccc ttggatgaga ggcaggcgct tcagagaagc taagaaaagc      300
acctctccgc gcgccccacc tcctccgcct cgcgctcctc ctgagcagcg ggcccagact      360
gcgctccggc gcggccctc gccccgcgga gccctcctac cccggcccga cgctcggccc      420
gcgacctgcc ccgagccctc tcc atg gag gca gcc cgc ccc tcc ggc tcc tgg      473
              Met Glu Ala Ala Arg Pro Ser Gly Ser Trp
                1               5                  10 aac gga gcc ctc tgc cgg ctg ctc ctg ctg acc ctc gcg atc tta ata      521
Asn Gly Ala Leu Cys Arg Leu Leu Leu Leu Thr Leu Ala Ile Leu Ile
            15                  20                  25 ttt gcc agt gat gcc tgc aaa aat gtg aca tta cat gtt ccc tcc aaa      569
Phe Ala Ser Asp Ala Cys Lys Asn Val Thr Leu His Val Pro Ser Lys -continued

```
                  30                  35                  40
cta gat gcc gag aaa ctt gtt ggt aga gtt aac ctg aaa gag tgc ttt      617
Leu Asp Ala Glu Lys Leu Val Gly Arg Val Asn Leu Lys Glu Cys Phe
        45                  50                  55 aca gct gca aat cta att cat tca agt gat cct gac ttc caa att ttg      665
Thr Ala Ala Asn Leu Ile His Ser Ser Asp Pro Asp Phe Gln Ile Leu
60                  65                  70 gag gat ggt tca gtc tat aca aca aat act att cta ttg tcc tcg gag      713
Glu Asp Gly Ser Val Tyr Thr Thr Asn Thr Ile Leu Leu Ser Ser Glu
75                  80                  85                  90 aag aga agt ttt acc ata tta ctt tcc aac act gag aac caa gaa aag      761
Lys Arg Ser Phe Thr Ile Leu Leu Ser Asn Thr Glu Asn Gln Glu Lys
                95                  100                 105 aag aaa ata ttt gtc ttt ttg gag cat caa aca aag gtc cta aag aaa      809
Lys Lys Ile Phe Val Phe Leu Glu His Gln Thr Lys Val Leu Lys Lys
                110                 115                 120 aga cat act aaa gaa aaa gtt cta agg cgc gcc aag aga aga tgg gct      857
Arg His Thr Lys Glu Lys Val Leu Arg Arg Ala Lys Arg Arg Trp Ala
        125                 130                 135 cca att cct tgt tcg atg cta gaa aac tcc ttg ggt cct ttt cca ctt      905
Pro Ile Pro Cys Ser Met Leu Glu Asn Ser Leu Gly Pro Phe Pro Leu
        140                 145                 150 ttc ctt caa cag gtt caa tct gac acg gcc caa aac tat acc ata tac      953
Phe Leu Gln Gln Val Gln Ser Asp Thr Ala Gln Asn Tyr Thr Ile Tyr
155                 160                 165                 170 tat tcc ata aga ggt cct gga gtt gac caa gaa cct cgg aat tta ttt     1001
Tyr Ser Ile Arg Gly Pro Gly Val Asp Gln Glu Pro Arg Asn Leu Phe
                175                 180                 185 tat gtg gag aga gac act gga aac ttg tat tgt act cgt cct gta gat     1049
Tyr Val Glu Arg Asp Thr Gly Asn Leu Tyr Cys Thr Arg Pro Val Asp
                190                 195                 200 cgt gag cag tat gaa tct ttt gag ata att gcc ttt gca aca act cca     1097
Arg Glu Gln Tyr Glu Ser Phe Glu Ile Ile Ala Phe Ala Thr Thr Pro
        205                 210                 215 gat ggg tat act cca gaa ctt cca ctg ccc cta ata atc aaa ata gag     1145
Asp Gly Tyr Thr Pro Glu Leu Pro Leu Pro Leu Ile Ile Lys Ile Glu
        220                 225                 230 gat gaa aat gat aac tac cca att ttt aca gaa gaa act tat act ttt     1193
Asp Glu Asn Asp Asn Tyr Pro Ile Phe Thr Glu Glu Thr Tyr Thr Phe
235                 240                 245                 250 aca att ttt gaa aat tgc aga gtg ggc act act gtg gga caa gtg tgt     1241
Thr Ile Phe Glu Asn Cys Arg Val Gly Thr Thr Val Gly Gln Val Cys
                255                 260                 265 gct act gac aaa gat gag cct gac acg atg cac aca cgc ctg aag tac     1289
Ala Thr Asp Lys Asp Glu Pro Asp Thr Met His Thr Arg Leu Lys Tyr
                270                 275                 280 tcc atc att ggg cag gtg cca cca tca ccc acc cta ttt tct atg cat     1337
Ser Ile Ile Gly Gln Val Pro Pro Ser Pro Thr Leu Phe Ser Met His
        285                 290                 295 cca act aca ggc gtg atc acc aca aca tca tct cag cta gac aga gag     1385
Pro Thr Thr Gly Val Ile Thr Thr Thr Ser Ser Gln Leu Asp Arg Glu
        300                 305                 310 tta att gac aag tac cag ttg aaa ata aaa gta caa gac atg gat ggt     1433
Leu Ile Asp Lys Tyr Gln Leu Lys Ile Lys Val Gln Asp Met Asp Gly
315                 320                 325                 330 cag tat ttt ggt cta cag aca act tca act tgt atc att aac att gat     1481
Gln Tyr Phe Gly Leu Gln Thr Thr Ser Thr Cys Ile Ile Asn Ile Asp
                335                 340                 345 gat gta aat gac cac ttg cca aca ttt act cgt act tct tat gtg aca     1529
```

```
                Asp Val Asn Asp His Leu Pro Thr Phe Thr Arg Thr Ser Tyr Val Thr
                                350                 355                 360 tca gtg gaa gaa aat aca gtt gat gtg gaa atc tta cga gtt act gtt            1577
Ser Val Glu Glu Asn Thr Val Asp Val Glu Ile Leu Arg Val Thr Val
            365                 370                 375 gag gat aag gac tta gtg aat act gct aac tgg aga gct aat tat acc            1625
Glu Asp Lys Asp Leu Val Asn Thr Ala Asn Trp Arg Ala Asn Tyr Thr
        380                 385                 390 att tta aag ggc aat gaa aat ggc aat ttt aaa att gta aca gat gcc            1673
Ile Leu Lys Gly Asn Glu Asn Gly Asn Phe Lys Ile Val Thr Asp Ala
395                 400                 405                 410 aaa acc aat gaa gga gtt ctt tgt gta gtt aag cct ttg aat tat gaa            1721
Lys Thr Asn Glu Gly Val Leu Cys Val Val Lys Pro Leu Asn Tyr Glu
                415                 420                 425 gaa aag caa cag atg atc ttg caa att ggt gta gtt aat gaa gct cca            1769
Glu Lys Gln Gln Met Ile Leu Gln Ile Gly Val Val Asn Glu Ala Pro
            430                 435                 440 ttt tcc aga gag gct agt cca aga tca gcc atg agc aca gca aca gtt            1817
Phe Ser Arg Glu Ala Ser Pro Arg Ser Ala Met Ser Thr Ala Thr Val
        445                 450                 455 act gtt aat gta gaa gat cag gat gag ggc cct gag tgt aac cct cca            1865
Thr Val Asn Val Glu Asp Gln Asp Glu Gly Pro Glu Cys Asn Pro Pro
    460                 465                 470 ata cag act gtt cgc atg aaa gaa aat gca gaa gtg gga aca aca agc            1913
Ile Gln Thr Val Arg Met Lys Glu Asn Ala Glu Val Gly Thr Thr Ser
475                 480                 485                 490 aat gga tat aaa gca tat gac cca gaa aca aga agt agc agt ggc ata            1961
Asn Gly Tyr Lys Ala Tyr Asp Pro Glu Thr Arg Ser Ser Ser Gly Ile
                495                 500                 505 agg tat aag aaa tta act gat cca aca ggg tgg gtc acc att gat gaa            2009
Arg Tyr Lys Lys Leu Thr Asp Pro Thr Gly Trp Val Thr Ile Asp Glu
            510                 515                 520 aat aca gga tca atc aaa gtt ttc aga agc ctg gat aga gag gca gag            2057
Asn Thr Gly Ser Ile Lys Val Phe Arg Ser Leu Asp Arg Glu Ala Glu
        525                 530                 535 acc atc aaa aat ggc ata tat aat att aca gtc ctt gca tca gac caa            2105
Thr Ile Lys Asn Gly Ile Tyr Asn Ile Thr Val Leu Ala Ser Asp Gln
    540                 545                 550 gga ggg aga aca tgt acg ggg aca ctg ggc att ata ctt caa gac gtg            2153
Gly Gly Arg Thr Cys Thr Gly Thr Leu Gly Ile Ile Leu Gln Asp Val
555                 560                 565                 570 aat gat aac agc cca ttc ata cct aaa aag aca gtg atc atc tgc aaa            2201
Asn Asp Asn Ser Pro Phe Ile Pro Lys Lys Thr Val Ile Ile Cys Lys
                575                 580                 585 ccc acc atg tca tct gcg gag att gtt gcg gtt gat cct gat gag cct            2249
Pro Thr Met Ser Ser Ala Glu Ile Val Ala Val Asp Pro Asp Glu Pro
            590                 595                 600 atc cat ggc cca ccc ttt gac ttt agt ctg gag agt tct act tca gaa            2297
Ile His Gly Pro Pro Phe Asp Phe Ser Leu Glu Ser Ser Thr Ser Glu
        605                 610                 615 gta cag aga atg tgg aga ctg aaa gca att aat gat aca gca gca cgt            2345
Val Gln Arg Met Trp Arg Leu Lys Ala Ile Asn Asp Thr Ala Ala Arg
    620                 625                 630 ctt tcc tat cag aat gat cct cca ttt ggc tca tat gta gta cct ata            2393
Leu Ser Tyr Gln Asn Asp Pro Pro Phe Gly Ser Tyr Val Val Pro Ile
635                 640                 645                 650 aca gtg aga gat aga ctt ggc atg tct agt gtc act tca ttg gat gtt            2441
Thr Val Arg Asp Arg Leu Gly Met Ser Ser Val Thr Ser Leu Asp Val
                655                 660                 665
```

```
aca ctg tgt gac tgc att acc gaa aat gac tgc aca cat cgt gta gat    2489
Thr Leu Cys Asp Cys Ile Thr Glu Asn Asp Cys Thr His Arg Val Asp
            670                 675                 680 cca agg att ggc ggt gga gga gta caa ctt gga aag tgg gcc atc ctt    2537
Pro Arg Ile Gly Gly Gly Gly Val Gln Leu Gly Lys Trp Ala Ile Leu
                685                 690                 695 gca ata ttg ttg ggc ata gca ttg ctc ttt tgc atc ctg ttt acg ctg    2585
Ala Ile Leu Leu Gly Ile Ala Leu Leu Phe Cys Ile Leu Phe Thr Leu
    700                 705                 710 gtc tgt ggg gct tct ggg acg tct aaa caa cca aaa gta att cct gat    2633
Val Cys Gly Ala Ser Gly Thr Ser Lys Gln Pro Lys Val Ile Pro Asp
715                 720                 725                 730 gat tta gcc cag cag aac cta att gta tca aac aca gaa gct cct gga    2681
Asp Leu Ala Gln Gln Asn Leu Ile Val Ser Asn Thr Glu Ala Pro Gly
                735                 740                 745 gat gac aaa gtg tat tct gcg aat ggc ttc aca acc caa act gtg ggc    2729
Asp Asp Lys Val Tyr Ser Ala Asn Gly Phe Thr Thr Gln Thr Val Gly
            750                 755                 760 gct tct gct cag gga gtt tgt ggc acc gtg gga tca gga atc aaa aac    2777
Ala Ser Ala Gln Gly Val Cys Gly Thr Val Gly Ser Gly Ile Lys Asn
    765                 770                 775 gga ggt cag gag acc atc gaa atg gtg aaa gga gga cac cag acc tcg    2825
Gly Gly Gln Glu Thr Ile Glu Met Val Lys Gly Gly His Gln Thr Ser
780                 785                 790 gaa tcc tgc cgg ggg gct ggc cac cat cac acc ctg gac tcc tgc agg    2873
Glu Ser Cys Arg Gly Ala Gly His His His Thr Leu Asp Ser Cys Arg
                795                 800                 805                 810 gga gga cac acg gag gtg gac aac tgc aga tac act tac tcg gag tgg    2921
Gly Gly His Thr Glu Val Asp Asn Cys Arg Tyr Thr Tyr Ser Glu Trp
            815                 820                 825 cac agt ttt act cag ccc cgt ctt ggt gaa aaa gtg tat ctg tgt aat    2969
His Ser Phe Thr Gln Pro Arg Leu Gly Glu Lys Val Tyr Leu Cys Asn
                830                 835                 840 caa gat gaa aat cac aag cat gcc caa gac tat gtc ctg aca tat aac    3017
Gln Asp Glu Asn His Lys His Ala Gln Asp Tyr Val Leu Thr Tyr Asn
            845                 850                 855 tat gaa gga aga gga tcg gtg gct ggg tct gta ggt tgt tgc agt gaa    3065
Tyr Glu Gly Arg Gly Ser Val Ala Gly Ser Val Gly Cys Cys Ser Glu
                860                 865                 870 cga caa gaa gaa gat ggg ctt gaa ttt ttg gat aat ttg gag ccc aaa    3113
Arg Gln Glu Glu Asp Gly Leu Glu Phe Leu Asp Asn Leu Glu Pro Lys
875                 880                 885                 890 ttt agg aca cta gca gaa gca tgc atg aag aga tgagtgtgtt ctaataagtc 3166
Phe Arg Thr Leu Ala Glu Ala Cys Met Lys Arg
                895                 900 tctgaaagcc agtggcttta tgactttaa aaaaaattac aaaccaagaa tttttaaag   3226 cagaagatgc tatttgtggg ggttttctc tcattatttg gatggaatct ctttggtcaa   3286
atgcacattt acagagagac actataaaca agtacacaaa tttttcaatt tttacatatt  3346
tttaaattac ttatcttcta tccaaggagg tctacagaga aattaaagtc tgccttattt   3406
gttacatttg gtataatga caacagccaa tttatagtgc aataaaatgt aattaattca    3466
agtccttatt atagactatt tgaagcacaa cctaatggaa aattgtagag accttgcttt   3526
aacattatct ccagttaatt aagtgttcat gtggtgcttg gaaactgttg ttttcctgaa   3586
catctaaagt gtgtagactg cattcttgct attatttat tcttgtaatg tgacctttc     3646 actgtgcaaa gggagatttc tagccaggca ttgactatta caattttcatt ttggtggagt  3706 ttagttttag gttttattgt atataaaaatc ctgcactgaa tctgtgtctc ctctgttacc  3766
```

```
tactttgcc agtgaaattt aagttttaaa atactttcag aatgtatttt tactactgca   3826
agttttggt ctttaaaatg tcaagtagca tctctctctt tctctctgtc tctttctgtt   3886
tctctctcca gtttttttt ttttttaat ttccatatgg gctaaagaat ccaaatattt    3946
taaaaatctg tctctctttt cttctctcat aaagtgaatt attccttttt tttgttttat   4006
gtaagtgtat atattcttag ttttcttga atcattgta atgttaactt tgttgtttca    4066
aatatcttgg tgattgcttc attatctctt caacaaaaaa aacctttaat tttgccattg   4126
aaactgtaga actatgccat gctttatta gaagcagtgc tctgtgttaa caacaagaat   4186
ggtgtaatta gaattgggat gtggatattt actgtatgac aacacattta cagttctgta   4246
atgcaaggat gcagtttaaa aatgtgaagt agtgatggtt tttgaaataa gctttaaaat   4306
atagggatct tgaaggctcc ctggggtaac tattttataa cttagataaa atggctagtc   4366
atatctgtgt gtttgtaaag ttattttttt aatattttaa gattacaatt ttaacaaatg   4426
tagaaatgag ccaaactatt taaattttaa aacagtaaaa caaaatgaaa cttaatagct   4486
cacaaaattc cagtccatgt ttcatgactt attttagtca atgaattttc tatttatact   4546
aaacatatgg acattttaaa tgtgtttcta atatttttga ttatctataa tgtgcctgtc   4606
ttcaattcac aagattgggt tataacaatt atttgccaga ttaacactag ggaattattt   4666
gataaccagc ttatcttatc agtagtttta ttgctgatca ggcaaaaata gttttccaaa   4726
gttattttta ataagtata tacaaaattc ttatatatta ctagtcatga taagtaaat    4786
taagcagttt ttaaaactta gtgtgagttt gttcatcaca ggtctgatat gagtttaagg   4846
gatttcgcac tccctgaatc agagaagtaa gacccctttcc ttagattcct gttatacatt   4906
ttttaaaatg tagagtttgt tttggagaca ttttcagtgc attgttattg ccatatttat   4966
ataatatgac tattctaaag gctgtgaggc catggggtat tggttaagtt gcttgctttt   5026
gctttgtcca ttttcatcat tttaaaatgg gggataataa cagaacttgt ttcctagggc   5086
cattgtaagt cacttgaata aaaaatagtt ttgaagcaaa aaaaaaaaa aaaa         5140
```

<210> SEQ ID NO 4
<211> LENGTH: 901
<212> TYPE: PRT
<213> ORGANISM: Homo sapiens

<400> SEQUENCE: 4

```
Met Glu Ala Ala Arg Pro Ser Gly Ser Trp Asn Gly Ala Leu Cys Arg
1               5                   10                  15

Leu Leu Leu Leu Thr Leu Ala Ile Leu Ile Phe Ala Ser Asp Ala Cys
            20                  25                  30

Lys Asn Val Thr Leu His Val Pro Ser Lys Leu Asp Ala Glu Lys Leu
        35                  40                  45

Val Gly Arg Val Asn Leu Lys Glu Cys Phe Thr Ala Ala Asn Leu Ile
    50                  55                  60

His Ser Asp Pro Asp Phe Gln Ile Leu Glu Asp Gly Ser Val Tyr
65                  70                  75                  80

Thr Thr Asn Thr Ile Leu Leu Ser Ser Glu Lys Arg Ser Phe Thr Ile
                85                  90                  95

Leu Leu Ser Asn Thr Glu Asn Gln Glu Lys Lys Ile Phe Val Phe
            100                 105                 110

Leu Glu His Gln Thr Lys Val Leu Lys Lys Arg His Thr Lys Glu Lys
        115                 120                 125
```

-continued

```
Val Leu Arg Arg Ala Lys Arg Arg Trp Ala Pro Ile Pro Cys Ser Met
            130                 135                 140
Leu Glu Asn Ser Leu Gly Pro Phe Pro Leu Phe Leu Gln Gln Val Gln
145                 150                 155                 160
Ser Asp Thr Ala Gln Asn Tyr Thr Ile Tyr Tyr Ser Ile Arg Gly Pro
                165                 170                 175
Gly Val Asp Gln Glu Pro Arg Asn Leu Phe Tyr Val Glu Arg Asp Thr
            180                 185                 190
Gly Asn Leu Tyr Cys Thr Arg Pro Val Asp Arg Glu Gln Tyr Glu Ser
        195                 200                 205
Phe Glu Ile Ile Ala Phe Ala Thr Thr Pro Asp Gly Tyr Thr Pro Glu
210                 215                 220
Leu Pro Leu Pro Leu Ile Ile Lys Ile Glu Asp Glu Asn Asp Asn Tyr
225                 230                 235                 240
Pro Ile Phe Thr Glu Glu Thr Tyr Thr Phe Thr Ile Phe Glu Asn Cys
                245                 250                 255
Arg Val Gly Thr Thr Val Gly Gln Val Cys Ala Thr Asp Lys Asp Glu
            260                 265                 270
Pro Asp Thr Met His Thr Arg Leu Lys Tyr Ser Ile Ile Gly Gln Val
        275                 280                 285
Pro Pro Ser Pro Thr Leu Phe Ser Met His Pro Thr Thr Gly Val Ile
290                 295                 300
Thr Thr Thr Ser Ser Gln Leu Asp Arg Glu Leu Ile Asp Lys Tyr Gln
305                 310                 315                 320
Leu Lys Ile Lys Val Gln Asp Met Asp Gly Gln Tyr Phe Gly Leu Gln
                325                 330                 335
Thr Thr Ser Thr Cys Ile Ile Asn Ile Asp Asp Val Asn Asp His Leu
            340                 345                 350
Pro Thr Phe Thr Arg Thr Ser Tyr Val Thr Ser Val Glu Glu Asn Thr
        355                 360                 365
Val Asp Val Glu Ile Leu Arg Val Thr Val Glu Asp Lys Asp Leu Val
370                 375                 380
Asn Thr Ala Asn Trp Arg Ala Asn Tyr Thr Ile Leu Lys Gly Asn Glu
385                 390                 395                 400
Asn Gly Asn Phe Lys Ile Val Thr Asp Ala Lys Thr Asn Glu Gly Val
                405                 410                 415
Leu Cys Val Val Lys Pro Leu Asn Tyr Glu Glu Lys Gln Gln Met Ile
            420                 425                 430
Leu Gln Ile Gly Val Val Asn Glu Ala Pro Phe Ser Arg Glu Ala Ser
        435                 440                 445
Pro Arg Ser Ala Met Ser Thr Ala Thr Val Thr Val Asn Val Glu Asp
450                 455                 460
Gln Asp Glu Gly Pro Glu Cys Asn Pro Pro Ile Gln Thr Val Arg Met
465                 470                 475                 480
Lys Glu Asn Ala Glu Val Gly Thr Thr Ser Asn Gly Tyr Lys Ala Tyr
                485                 490                 495
Asp Pro Glu Thr Arg Ser Ser Gly Ile Arg Tyr Lys Lys Leu Thr
            500                 505                 510
Asp Pro Thr Gly Trp Val Thr Ile Asp Glu Asn Thr Gly Ser Ile Lys
        515                 520                 525
Val Phe Arg Ser Leu Asp Arg Glu Ala Glu Thr Ile Lys Asn Gly Ile
530                 535                 540
Tyr Asn Ile Thr Val Leu Ala Ser Asp Gln Gly Gly Arg Thr Cys Thr
```

```
                545                 550                 555                 560
Gly Thr Leu Gly Ile Ile Leu Gln Asp Val Asn Asp Asn Ser Pro Phe
                565                 570                 575
Ile Pro Lys Lys Thr Val Ile Ile Cys Lys Pro Thr Met Ser Ser Ala
                580                 585                 590
Glu Ile Val Ala Val Asp Pro Asp Glu Pro Ile His Gly Pro Pro Phe
                595                 600                 605
Asp Phe Ser Leu Glu Ser Ser Thr Ser Glu Val Gln Arg Met Trp Arg
                610                 615                 620
Leu Lys Ala Ile Asn Asp Thr Ala Ala Arg Leu Ser Tyr Gln Asn Asp
625                 630                 635                 640
Pro Pro Phe Gly Ser Tyr Val Val Pro Ile Thr Val Arg Asp Arg Leu
                645                 650                 655
Gly Met Ser Ser Val Thr Ser Leu Asp Val Thr Leu Cys Asp Cys Ile
                660                 665                 670
Thr Glu Asn Asp Cys Thr His Arg Val Asp Pro Arg Ile Gly Gly Gly
                675                 680                 685
Gly Val Gln Leu Gly Lys Trp Ala Ile Leu Ala Ile Leu Leu Gly Ile
                690                 695                 700
Ala Leu Leu Phe Cys Ile Leu Phe Thr Leu Val Cys Gly Ala Ser Gly
705                 710                 715                 720
Thr Ser Lys Gln Pro Lys Val Ile Pro Asp Asp Leu Ala Gln Gln Asn
                725                 730                 735
Leu Ile Val Ser Asn Thr Glu Ala Pro Gly Asp Asp Lys Val Tyr Ser
                740                 745                 750
Ala Asn Gly Phe Thr Thr Gln Thr Val Gly Ala Ser Ala Gln Gly Val
                755                 760                 765
Cys Gly Thr Val Gly Ser Gly Ile Lys Asn Gly Gly Gln Glu Thr Ile
                770                 775                 780
Glu Met Val Lys Gly Gly His Gln Thr Ser Glu Ser Cys Arg Gly Ala
785                 790                 795                 800
Gly His His His Thr Leu Asp Ser Cys Arg Gly Gly His Thr Glu Val
                805                 810                 815
Asp Asn Cys Arg Tyr Thr Tyr Ser Glu Trp His Ser Phe Thr Gln Pro
                820                 825                 830
Arg Leu Gly Glu Lys Val Tyr Leu Cys Asn Gln Asp Glu Asn His Lys
                835                 840                 845
His Ala Gln Asp Tyr Val Leu Thr Tyr Asn Tyr Glu Gly Arg Gly Ser
                850                 855                 860
Val Ala Gly Ser Val Gly Cys Cys Ser Glu Arg Gln Glu Glu Asp Gly
865                 870                 875                 880
Leu Glu Phe Leu Asp Asn Leu Glu Pro Lys Phe Arg Thr Leu Ala Glu
                885                 890                 895
Ala Cys Met Lys Arg
                900

<210> SEQ ID NO 5
<211> LENGTH: 29
<212> TYPE: DNA
<213> ORGANISM: artificial
<220> FEATURE:
<223> OTHER INFORMATION: An artificially synthesized primer sequence for
      construction of expression vector.

<400> SEQUENCE: 5
```
aatattaatt aactccatgg aggcagccc                                  29

<210> SEQ ID NO 6
<211> LENGTH: 33
<212> TYPE: DNA
<213> ORGANISM: artificial
<220> FEATURE:
<223> OTHER INFORMATION: An artificially synthesized primer sequence for
      construction of expression vector.

<400> SEQUENCE: 6
atcgggatcc tctcttcatg catgcttctg cta                             33

<210> SEQ ID NO 7
<211> LENGTH: 24
<212> TYPE: DNA
<213> ORGANISM: artificial
<220> FEATURE:
<223> OTHER INFORMATION: An artificially synthesized primer sequence for
      construction of expression vector.

<400> SEQUENCE: 7
aataggatcc tccaccgcca atcc                                       24

<210> SEQ ID NO 8
<211> LENGTH: 21
<212> TYPE: DNA
<213> ORGANISM: artificial
<220> FEATURE:
<223> OTHER INFORMATION: An artificially synthesized primer sequence for
      RT-PCR.

<400> SEQUENCE: 8
gtgcctgtct tcaattcaca a                                          21

<210> SEQ ID NO 9
<211> LENGTH: 20
<212> TYPE: DNA
<213> ORGANISM: artificial
<220> FEATURE:
<223> OTHER INFORMATION: An artificially synthesized primer sequence for
      RT-PCR.

<400> SEQUENCE: 9
tctgattcag ggagtgcgaa                                            20

<210> SEQ ID NO 10
<211> LENGTH: 23
<212> TYPE: DNA
<213> ORGANISM: artificial
<220> FEATURE:
<223> OTHER INFORMATION: An artificially synthesized primer sequence for
      RT-PCR.

<400> SEQUENCE: 10
gtatttgatg gtgacctggg aat                                        23

<210> SEQ ID NO 11
<211> LENGTH: 22
<212> TYPE: DNA
<213> ORGANISM: artificial
<220> FEATURE:
<223> OTHER INFORMATION: An artificially synthesized primer sequence for
      RT-PCR.

<400> SEQUENCE: 11
cccctgggtc tttatttcat ct                                         22

-continued

<210> SEQ ID NO 12
<211> LENGTH: 20
<212> TYPE: DNA
<213> ORGANISM: artificial
<220> FEATURE:
<223> OTHER INFORMATION: An artificially synthesized primer sequence for
      RT-PCR.

<400> SEQUENCE: 12
gtcagtggtg gacctgacct                                                    20

<210> SEQ ID NO 13
<211> LENGTH: 23
<212> TYPE: DNA
<213> ORGANISM: artificial
<220> FEATURE:
<223> OTHER INFORMATION: An artificially synthesized primer sequence for
      RT-PCR.

<400> SEQUENCE: 13
ggttgagcac agggtacttt att                                                23

<210> SEQ ID NO 14
<211> LENGTH: 21
<212> TYPE: DNA
<213> ORGANISM: artificial
<220> FEATURE:
<223> OTHER INFORMATION: An artificially synthesized primer sequence for
      RT-PCR.

<400> SEQUENCE: 14
gaggtgatag cattgctttc g                                                  21

<210> SEQ ID NO 15
<211> LENGTH: 21
<212> TYPE: DNA
<213> ORGANISM: artificial
<220> FEATURE:
<223> OTHER INFORMATION: An artificially synthesized primer sequence for
      RT-PCR.

<400> SEQUENCE: 15
caagtcagtg tacaggtaag c                                                  21

<210> SEQ ID NO 16
<211> LENGTH: 130
<212> TYPE: PRT
<213> ORGANISM: Homo sapiens

<400> SEQUENCE: 16

Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Asn
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Lys Tyr Asn Pro Ser Leu Lys
    50                  55                  60

Ser Arg Val Ala Ile Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Arg Val Pro Phe Asp Trp Phe His Pro Pro Gly Glu Pro Pro Phe Tyr
            100                 105                 110

Tyr Tyr Tyr Gly Met Asp Val Trp Gly Gln Gly Thr Thr Val Thr Val
            115                 120                 125

Ser Ser
    130

<210> SEQ ID NO 17
<211> LENGTH: 112
<212> TYPE: PRT
<213> ORGANISM: Homo sapiens

<400> SEQUENCE: 17

His Val Ile Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Pro Gly
            100                 105                 110

<210> SEQ ID NO 18
<211> LENGTH: 118
<212> TYPE: PRT
<213> ORGANISM: Homo sapiens

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Phe Trp Ser Trp Ile Arg Gln Ala Pro Gly Lys Gly Leu Glu Trp Ile
            35                  40                  45

Gly Glu Ile Asn His Ser Gly Ser Thr Ser Tyr Asn Pro Ser Leu Lys
        50                  55                  60

Ser Arg Val Thr Met Thr Ile Asp Thr Ser Arg Lys Gln Phe Ser Leu
65                  70                  75                  80

Lys Leu Ser Ser Val Thr Ala Ala Asp Ala Ala Val Tyr Tyr Cys Ala
                85                  90                  95

Arg Gly Gln Gly Tyr Tyr Ser Ser Leu Asp Pro Trp Gly Gln Gly Thr
            100                 105                 110

Leu Val Thr Val Ser Ser
        115

<210> SEQ ID NO 19
<211> LENGTH: 111
<212> TYPE: PRT
<213> ORGANISM: Homo sapiens

<400> SEQUENCE: 19

Ser Tyr Glu Leu Thr Gln Pro Pro Ser Ala Ser Gly Thr Pro Gly Gln
```

```
1               5                   10                  15
Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110

<210> SEQ ID NO 20
<211> LENGTH: 136
<212> TYPE: PRT
<213> ORGANISM: Mus musculus

<400> SEQUENCE: 20

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Val His Tyr Tyr Tyr Phe Asp Tyr Trp Gly Gln
        115                 120                 125

Gly Thr Thr Leu Thr Val Ser Ser
            130                 135

<210> SEQ ID NO 21
<211> LENGTH: 123
<212> TYPE: PRT
<213> ORGANISM: Mus musculus

<400> SEQUENCE: 21

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
```

```
                  85                  90                  95
Asn Leu Glu Pro Glu Asp Ile Ala Thr Tyr Tyr Cys Leu Gln Tyr Asp
                100                 105                 110

Asn Leu Trp Thr Phe Gly Gly Gly Thr Lys Leu
            115                 120

<210> SEQ ID NO 22
<211> LENGTH: 134
<212> TYPE: PRT
<213> ORGANISM: Mus musculus

<400> SEQUENCE: 22

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ser Met His Trp Val Lys Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Trp Leu Leu Phe Asp Tyr Trp Gly Gln Gly Thr
        115                 120                 125

Thr Leu Thr Val Ser Ser
    130

<210> SEQ ID NO 23
<211> LENGTH: 130
<212> TYPE: PRT
<213> ORGANISM: Mus musculus

<400> SEQUENCE: 23

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ser Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

Phe Cys Gln Gln His Tyr Ser Thr Pro Leu Thr Phe Gly Ala Gly Thr
        115                 120                 125

Lys Leu
    130
```

<210> SEQ ID NO 24
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 24
aattttcttg tccaccttgg tg                                           22

<210> SEQ ID NO 25
<211> LENGTH: 26
<212> TYPE: DNA
<213> ORGANISM: Artificial
<220> FEATURE:
<223> OTHER INFORMATION: An artificially synthesized primer for RT-PCR

<400> SEQUENCE: 25
ctaacactca ttcctgttga agctct                                       26

<210> SEQ ID NO 26
<211> LENGTH: 7
<212> TYPE: PRT
<213> ORGANISM: Mus musculus

<400> SEQUENCE: 26

Phe Ser Ser Phe Gly Met His
1               5

<210> SEQ ID NO 27
<211> LENGTH: 16
<212> TYPE: PRT
<213> ORGANISM: Mus musculus

<400> SEQUENCE: 27

Tyr Ile Ser Ser Gly Ser Ser Thr Ile Tyr Tyr Ala Asp Thr Val Lys
1               5                   10                  15

<210> SEQ ID NO 28
<211> LENGTH: 8
<212> TYPE: PRT
<213> ORGANISM: Mus musculus

<400> SEQUENCE: 28

Val His Tyr Tyr Tyr Phe Asp Tyr
1               5

<210> SEQ ID NO 29
<211> LENGTH: 11
<212> TYPE: PRT
<213> ORGANISM: Mus musculus

<400> SEQUENCE: 29

Lys Ala Ser Gln Asp Ile Asn Lys Tyr Ile Ala
1               5                   10

<210> SEQ ID NO 30
<211> LENGTH: 7
<212> TYPE: PRT
<213> ORGANISM: Mus musculus

<400> SEQUENCE: 30

Tyr Thr Ser Thr Leu Gln Pro
1               5

```
<210> SEQ ID NO 31
<211> LENGTH: 7
<212> TYPE: PRT
<213> ORGANISM: Mus musculus

<400> SEQUENCE: 31

Leu Gln Tyr Asp Asn Leu Trp
1               5

<210> SEQ ID NO 32
<211> LENGTH: 5
<212> TYPE: PRT
<213> ORGANISM: Mus musculus

<400> SEQUENCE: 32

Asp Tyr Ser Met His
1               5

<210> SEQ ID NO 33
<211> LENGTH: 17
<212> TYPE: PRT
<213> ORGANISM: Mus musculus

<400> SEQUENCE: 33

Trp Ile Asn Thr Glu Thr Gly Glu Pro Thr Tyr Ala Asp Asp Phe Lys
1               5                   10                  15

Gly

<210> SEQ ID NO 34
<211> LENGTH: 6
<212> TYPE: PRT
<213> ORGANISM: Mus musculus

<400> SEQUENCE: 34

Trp Leu Leu Phe Asp Tyr
1               5

<210> SEQ ID NO 35
<211> LENGTH: 17
<212> TYPE: PRT
<213> ORGANISM: Mus musculus

<400> SEQUENCE: 35

Lys Ser Ser Gln Ser Leu Leu Asn Ser Asn Gln Lys Asn Tyr Leu
1               5                   10                  15

Ala

<210> SEQ ID NO 36
<211> LENGTH: 7
<212> TYPE: PRT
<213> ORGANISM: Mus musculus

<400> SEQUENCE: 36

Phe Ala Ser Thr Arg Glu Ser
1               5

<210> SEQ ID NO 37
<211> LENGTH: 8
<212> TYPE: PRT
<213> ORGANISM: Mus musculus

<400> SEQUENCE: 37

Gln Gln His Tyr Ser Thr Pro Leu
1               5
```

<210> SEQ ID NO 38
<211> LENGTH: 390
<212> TYPE: DNA
<213> ORGANISM: Homo sapiens

<400> SEQUENCE: 38

```
caggtgcagc tacagcagtg gggcgcagga ctgttgaagc cttcggagac cctgtccctc      60
acctgcgctg tctatggtgg gtccttcagt ggtaactact ggagctggat ccgccagccc     120
ccagggaagg ggctggagtg gattggggaa atcaatcata gtggaaacac caagtacaac     180
ccgtccctca agagtcgagt cgccatatcg gcagacacgt ccaagaacca gttctccctg     240
aagctgagct ctgtgaccgc cgcggacacg gctgtgtatt actgtgcgag agtgcccttt     300
gactggttcc acccacccgg tgagcccccc ttttactact actacggtat ggacgtctgg     360
ggccaaggga ccacggtcac cgtctcgagc                                      390
```

<210> SEQ ID NO 39
<211> LENGTH: 5
<212> TYPE: PRT
<213> ORGANISM: Homo sapiens

<400> SEQUENCE: 39

Gly Asn Tyr Trp Ser
1               5

<210> SEQ ID NO 40
<211> LENGTH: 16
<212> TYPE: PRT
<213> ORGANISM: Homo sapiens

<400> SEQUENCE: 40

Glu Ile Asn His Ser Gly Asn Thr Lys Tyr Asn Pro Ser Leu Lys Ser
1               5                   10                  15

<210> SEQ ID NO 41
<211> LENGTH: 22
<212> TYPE: PRT
<213> ORGANISM: Homo sapiens

<400> SEQUENCE: 41

Val Pro Phe Asp Trp Phe His Pro Pro Gly Glu Pro Pro Phe Tyr Tyr
1               5                   10                  15

Tyr Tyr Gly Met Asp Val
            20

<210> SEQ ID NO 42
<211> LENGTH: 330
<212> TYPE: PRT
<213> ORGANISM: Homo sapiens

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Pro His Asn His Tyr Thr
305                 310                 315                 320

Gln Lys Ser Leu Ser Leu Ser Pro Gly Lys
                325                 330

<210> SEQ ID NO 43
<211> LENGTH: 657
<212> TYPE: DNA
<213> ORGANISM: Homo sapiens

<400> SEQUENCE: 43
cacgttatac tgactcaacc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttgg     300
gtgttcggcg gagggaccaa gctgaccgtc ccaggtcagc ccaaggctgc ccctcggtc      360 actctgttcc cgccctcctc tgaggagctt caagccaaca ggccacact ggtgtgtctc      420 ataagtgact tctacccggg agccgtgaca gtggcctgga aggcagatag cagccccgtc     480
aaggcgggag tggagaccac cacacccctc aaacaaggca caacaagta cgcggccagc     540 agctacctga gcctgacgcc tgagcagtgg aagtcccaca aaagctacag ctgccaggtc     600

```
acgcatgaag ggagcaccgt ggagaagaca gtggccccta cagaatgttc ggcgcgc       657
```

<210> SEQ ID NO 44
<211> LENGTH: 14
<212> TYPE: PRT
<213> ORGANISM: Homo sapiens

<400> SEQUENCE: 44

Thr Gly Ser Ser Ser Asn Ile Gly Ala Gly Tyr Asp Val His
1               5                   10

<210> SEQ ID NO 45
<211> LENGTH: 7
<212> TYPE: PRT
<213> ORGANISM: Homo sapiens

<400> SEQUENCE: 45

Gly Asn Ser Asn Arg Pro Ser
1               5

<210> SEQ ID NO 46
<211> LENGTH: 11
<212> TYPE: PRT
<213> ORGANISM: Homo sapiens

<400> SEQUENCE: 46

Gln Ser Tyr Asp Ser Ser Leu Ser Gly Trp Val
1               5                   10

<210> SEQ ID NO 47
<211> LENGTH: 105
<212> TYPE: PRT
<213> ORGANISM: Homo sapiens

<400> SEQUENCE: 47

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Gly Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 48
<211> LENGTH: 354
<212> TYPE: DNA
<213> ORGANISM: Homo sapiens

<400> SEQUENCE: 48

```
caggtgcagc tccagcagtg gggcgcagga ctgttgaagc cttcggagac cctgtccctc       60
acctgcgctg tctatggtgg gtccttcagt ggttacttct ggagttggat ccgccaggcc      120
ccagggaagg ggctggagtg gattggggaa atcaatcata gtggaagcac cagctacaac      180
ccgtccctca agagtcgagt caccatgaca atagacacgt ccaggaagca gttctccctg      240
```

```
aagctgagct ctgtgaccgc cgcggacgcg gctgtctatt actgtgcgag aggccaggga    300
tattactcat ctttggaccc ctggggccag ggaaccctgg tcaccgtctc gagc          354
```

<210> SEQ ID NO 49
<211> LENGTH: 5
<212> TYPE: PRT
<213> ORGANISM: Homo sapiens

<400> SEQUENCE: 49

```
Gly Tyr Phe Trp Ser
1               5
```

<210> SEQ ID NO 50
<211> LENGTH: 16
<212> TYPE: PRT
<213> ORGANISM: Homo sapiens

<400> SEQUENCE: 50

```
Glu Ile Asn His Ser Gly Ser Thr Ser Tyr Asn Pro Ser Leu Lys Ser
1               5                   10                  15
```

<210> SEQ ID NO 51
<211> LENGTH: 10
<212> TYPE: PRT
<213> ORGANISM: Homo sapiens

<400> SEQUENCE: 51

```
Gly Gln Gly Tyr Tyr Ser Ser Leu Asp Pro
1               5                   10
```

<210> SEQ ID NO 52
<211> LENGTH: 654
<212> TYPE: DNA
<213> ORGANISM: Homo sapiens

<400> SEQUENCE: 52

```
tcctatgagc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggttccct    180
gaccgattct ctggctccaa gtctggcacc tcagcctccc tggccatcag tgggctccag   240
tctgaggatg aggctgatta ttactgtgca gcatgggatg acagcctgaa tggtgtggta   300
ttcggcggag ggaccaagct gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca acaagtacgc ggccagcagc   540
tatctgagcc tgacgcctga gcagtggaag tcccacagaa gctacagctg ccaggtcacg   600
catgaaggga gcaccgtgga agacagtg gcccctacag aatgttcggc gcgc           654
```

<210> SEQ ID NO 53
<211> LENGTH: 13
<212> TYPE: PRT
<213> ORGANISM: Homo sapiens

<400> SEQUENCE: 53

```
Ser Gly Ser Ser Ser Asn Ile Gly Ser Asn Thr Val Asn
1               5                   10
```

```
<210> SEQ ID NO 54
<211> LENGTH: 7
<212> TYPE: PRT
<213> ORGANISM: Homo sapiens

<400> SEQUENCE: 54

Ser Asn Asn Gln Arg Pro Ser
1               5

<210> SEQ ID NO 55
<211> LENGTH: 11
<212> TYPE: PRT
<213> ORGANISM: Homo sapiens

<400> SEQUENCE: 55

Ala Ala Trp Asp Asp Ser Leu Asn Gly Val Val
1               5                  10

<210> SEQ ID NO 56
<211> LENGTH: 105
<212> TYPE: PRT
<213> ORGANISM: Homo sapiens

<400> SEQUENCE: 56

Gln Pro Lys Ala Ala Pro Ser Val Thr Leu Phe Pro Pro Ser Ser Glu
1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 57
<211> LENGTH: 15
<212> TYPE: DNA
<213> ORGANISM: Homo sapiens

<400> SEQUENCE: 57
ggtaactact ggagc                                                      15

<210> SEQ ID NO 58
<211> LENGTH: 48
<212> TYPE: DNA
<213> ORGANISM: Homo sapiens

<400> SEQUENCE: 58
gaaatcaatc atagtggaaa caccaagtac aacccgtccc tcaagagt                  48

<210> SEQ ID NO 59
<211> LENGTH: 66
<212> TYPE: DNA
<213> ORGANISM: Homo sapiens

<400> SEQUENCE: 59
```

```
gtgcccttg actggttcca cccacccggt gagccccct tttactacta ctacggtatg    60
gacgtc                                                              66

<210> SEQ ID NO 60
<211> LENGTH: 42
<212> TYPE: DNA
<213> ORGANISM: Homo sapiens

<400> SEQUENCE: 60
actgggagca gctccaacat cggggcaggt tatgatgtac ac                     42

<210> SEQ ID NO 61
<211> LENGTH: 21
<212> TYPE: DNA
<213> ORGANISM: Homo sapiens

<400> SEQUENCE: 61
ggtaacagca atcggccctc a                                            21

<210> SEQ ID NO 62
<211> LENGTH: 33
<212> TYPE: DNA
<213> ORGANISM: Homo sapiens

<400> SEQUENCE: 62
cagtcctatg acagcagcct gagtggttgg gtg                               33

<210> SEQ ID NO 63
<211> LENGTH: 15
<212> TYPE: DNA
<213> ORGANISM: Homo sapiens

<400> SEQUENCE: 63
ggttacttct ggagt                                                   15

<210> SEQ ID NO 64
<211> LENGTH: 48
<212> TYPE: DNA
<213> ORGANISM: Homo sapiens

<400> SEQUENCE: 64
gaaatcaatc atagtggaag caccagctac aacccgtccc tcaagagt               48

<210> SEQ ID NO 65
<211> LENGTH: 30
<212> TYPE: DNA
<213> ORGANISM: Homo sapiens

<400> SEQUENCE: 65
ggccagggat attactcatc tttggacccc                                   30

<210> SEQ ID NO 66
<211> LENGTH: 39
<212> TYPE: DNA
<213> ORGANISM: Homo sapiens

<400> SEQUENCE: 66
tctggaagca gctccaacat cggaagtaat actgtaaac                         39

<210> SEQ ID NO 67
<211> LENGTH: 21
<212> TYPE: DNA
<213> ORGANISM: Homo sapiens
```

<400> SEQUENCE: 67
agtaataatc agcggccctc a                                           21

<210> SEQ ID NO 68
<211> LENGTH: 33
<212> TYPE: DNA
<213> ORGANISM: Homo sapiens

<400> SEQUENCE: 68
gcagcatggg atgacagcct gaatggtgtg gta                              33

<210> SEQ ID NO 69
<211> LENGTH: 408
<212> TYPE: DNA
<213> ORGANISM: Mus musculus

<400> SEQUENCE: 69
atggactcca ggctcaattt agttttcctt gtccttattt taaaaggtgt ccagtgtgat    60
gtgcagctgg tggagtctgg gggaggctta gtgcagcctg agggtcccg gaaactctcc   120 tgtgcagcct ctggattcac tttcagtagc tttggaatgc actgggttcg tcaggctcca   180
gagaaggggc tggagtgggt cgcatacatt agtagtggca gtagtaccat ctactatgca   240
gacacagtga agggccgatt caccatctcc agagacaatc ccaagaacac cctgttcctg   300
caaatgacca gtctaaggtc tgaggacacg gccatgtatt actgtgcaag agttcattac   360
tactactttg actactgggg ccaaggcacc actctcacag tctcctca              408

<210> SEQ ID NO 70
<211> LENGTH: 21
<212> TYPE: DNA
<213> ORGANISM: Mus musculus

<400> SEQUENCE: 70
ttcagtagct ttggaatgca c                                           21

<210> SEQ ID NO 71
<211> LENGTH: 48
<212> TYPE: DNA
<213> ORGANISM: Mus musculus

<400> SEQUENCE: 71
tacattagta gtggcagtag taccatctac tatgcagaca cagtgaag              48

<210> SEQ ID NO 72
<211> LENGTH: 24
<212> TYPE: DNA
<213> ORGANISM: Mus musculus

<400> SEQUENCE: 72
gttcattact actactttga ctac                                        24

<210> SEQ ID NO 73
<211> LENGTH: 369
<212> TYPE: DNA
<213> ORGANISM: Mus musculus

<400> SEQUENCE: 73
atgagaccgt ctattcagtt cctggggctc ttgttgttct ggcttcatgg tgctcagtgt    60
gacatccaga tgacacagtc tccatcctca ctgtctgcat ctctgggagg caaagtcacc   120

```
atcacttgca aggcaagcca agacattaac aagtatatag cttggtacca acacaagcct    180
ggaaaaggtc ctaggctgct catacattac acatctacat tacagccagg catcccatca    240
aggttcagtg gaagtgggtc tgggagagat tattccttca gcatcagcaa cctggagcct    300
gaagatattg caacttatta ttgtctacag tatgataatc tgtggacgtt cggtggaggc    360
accaagctg                                                            369
```

```
<210> SEQ ID NO 74
<211> LENGTH: 33
<212> TYPE: DNA
<213> ORGANISM: Mus musculus

<400> SEQUENCE: 74
aaggcaagcc aagacattaa caagtatata gct                                  33
```

```
<210> SEQ ID NO 75
<211> LENGTH: 21
<212> TYPE: DNA
<213> ORGANISM: Mus musculus

<400> SEQUENCE: 75
tacacatcta cattacagcc a                                               21
```

```
<210> SEQ ID NO 76
<211> LENGTH: 21
<212> TYPE: DNA
<213> ORGANISM: Mus musculus

<400> SEQUENCE: 76
ctacagtatg ataatctgtg g                                               21
```

```
<210> SEQ ID NO 77
<211> LENGTH: 402
<212> TYPE: DNA
<213> ORGANISM: Mus musculus

<400> SEQUENCE: 77
atggcttggg tgtggacctt gctattcctg atggcagctg cccaaagtat ccaagcacag     60
atccagttgg tgcagtctgg acctgagctg aagaagcctg gagagacagt caagatctcc    120
tgcaaggctt ctggttatac cttcacagac tattcaatgc actgggtgaa gcaggctcca    180
ggaaagggtt taaagtggat gggctggata aacactgaga ctggtgagcc aacatatgca    240
gatgacttca agggacggtt tgccttctct ttggaaacct ctgccagcac tgcctatttg    300
cagatcaaca acctcaaaaa tgaggacacg gctacatatt tctgtgctag atggttactc    360
tttgactact ggggccaagg caccactctc acagtctcct ca                       402
```

```
<210> SEQ ID NO 78
<211> LENGTH: 15
<212> TYPE: DNA
<213> ORGANISM: Mus musculus

<400> SEQUENCE: 78
gactattcaa tgcac                                                      15
```

```
<210> SEQ ID NO 79
<211> LENGTH: 51
<212> TYPE: DNA
<213> ORGANISM: Mus musculus

<400> SEQUENCE: 79
```

```
tggataaaca ctgagactgg tgagccaaca tatgcagatg acttcaaggg a        51

<210> SEQ ID NO 80
<211> LENGTH: 18
<212> TYPE: DNA
<213> ORGANISM: Mus musculus

<400> SEQUENCE: 80
tggttactct ttgactac                                             18

<210> SEQ ID NO 81
<211> LENGTH: 390
<212> TYPE: DNA
<213> ORGANISM: Mus musculus

<400> SEQUENCE: 81
atggaatcac agacccaggt cctcatgttt cttctgctct gggtatctgg tgcctgtgca    60
gacattgtga tgacacagtc tccatcctcc ctggctatgt cagtaggaca gaaggtcact   120
atgagctgca gtccagtca gagccttta aatagtagca atcaaaagaa ctatttggcc    180
tggtaccagc agaaaccagg acagtctcct aaacttctgg tatactttgc atccactagg   240
gaatctgggg tccctgatcg cttcataggc agtggatctg ggacagattt cactcttacc   300
atcagcagtg tgcaggctga agacctggca gattacttct gtcagcaaca ttatagcact   360
ccgctcacgt cggtgctgg gaccaagctg                                    390

<210> SEQ ID NO 82
<211> LENGTH: 51
<212> TYPE: DNA
<213> ORGANISM: Mus musculus

<400> SEQUENCE: 82
aagtccagtc agagcctttt aaatagtagc aatcaaaaga actatttggc c           51

<210> SEQ ID NO 83
<211> LENGTH: 21
<212> TYPE: DNA
<213> ORGANISM: Mus musculus

<400> SEQUENCE: 83
tttgcatcca ctagggaatc t                                          21

<210> SEQ ID NO 84
<211> LENGTH: 24
<212> TYPE: DNA
<213> ORGANISM: Mus musculus

<400> SEQUENCE: 84
cagcaacatt atagcactcc gctc                                       24

<210> SEQ ID NO 85
<211> LENGTH: 8759
<212> TYPE: DNA
<213> ORGANISM: Artificial
<220> FEATURE:
<223> OTHER INFORMATION: An artificially synthesized expression cassette
      sequence

<400> SEQUENCE: 85
tccgcgttac ataacttacg gtaaatggcc cgcctggctg accgcccaac gacccccgcc    60
cattgacgtc aataatgacg tatgttccca tagtaacgcc aatagggact tccattgac    120
```

```
gtcaatgggt ggagtattta cggtaaactg cccacttggc agtacatcaa gtgtatcata      180
tgccaagtac gcccectatt gacgtcaatg acggtaaatg gcccgcctgg cattatgccc      240
agtacatgac cttatgggac tttcctactt ggcagtacat ctacgtatta gtcatcgcta      300
ttaccatggt gatgcggttt tggcagtaca tcaatgggcg tggatagcgg tttgactcac      360
ggggatttcc aagtctccac cccattgacg tcaatgggat tttgttttgg caccaaaatc      420
aacgggactt tccaaaatgt cgtaacaact ccgccccatt gacgcaaatg gcggtaggc      480 gtgtacggtg gaggtctat ataagcagag ctcaataaaa gagcccacaa cccctcactc      540
ggcgcgccag tcttccgata gactgcgtcg cccgggtacc cgtattccca ataaagcctc      600
ttgctgtttg catccgaatc gtggtctcgc tgttccttgg gagggtctcc tctgagtgat      660
tgactaccca cgacgggggt cttcattg gggctcgtc cgggatttgg agaccctgc       720 ccagggacca ccgacccacc accgggaggt aagctggcca gcaacttatc tgtgtctgtc      780
cgattgtcta gtgtctatgt tgatgttat gcgcctgcgt ctgtactagt tagctaacta      840
gctctgtatc tggcggaccc gtggtggaac tgacgagttc tgaacacccg gccgcaaccc      900
tgggagacgt cccagggact ttgggggccg ttttttgtggc ccgacctgag aagggagtc      960 gatgtggaat ccgacccgt caggatatgt ggttctggta ggagacgaga acctaaaaca     1020 gttccgcct ccgtctgaat ttttgctttc ggtttggaac cgaagccgcg cgtcttgtct     1080
gctgcagcgc tgcagcatcg ttctgtgttg tctctgtctg actgtgtttc tgtatttgtc     1140
tgaaaattag ggccagactg ttaccactcc cttaagtttg accttaggtc actggaaaga     1200
tgtcgagcgg atcgctcaca accagtcggt agatgtcaag aagagacgtt gggttacctt     1260
ctgctctgca gaatggccaa cctttaacgt cggatggccg cgagacggca cctttaaccg     1320
agacctcatc acccaggtta agatcaaggt cttttcacct ggcccgcatg gacacccaga     1380
ccaggtcccc tacatcgtga cctgggaagc cttggctttt gacccccctc cctgggtcaa     1440
gccctttgta cacctaagc ctccgcctcc tcttcctcca tccgcccgt ctctccccct      1500 tgaacctcct cgttcgaccc cgcctcgatc ctccctttat ccagccctca ctccttctct     1560
aggcgccgga attgaagatc tgggggatcg atcctctaga gtccgttaca taacttacgg     1620
taaatggccc gcctggctga ccgcccaacg accccgccc attgacgtca ataatgacgt     1680
atgttcccat agtaacgcca tagggactt ccattgacg tcaatgggtg gagtatttac       1740
ggtaaactgc ccacttggca gtacatcaag tgtatcatat gccaagtacg cccectattg     1800 acgtcaatga cggtaaatgg cccgcctggc attatgccca gtacatgacc ttatgggact     1860
ttcctacttg gcagtacatc tacgtattag tcatcgctat taccatggtg atgcggtttt     1920
ggcagtacat caatgggcgt gaatagcggt ttgactcacg ggatttcca agtctccacc       1980 ccattgacgt caatgggagt ttgttttggc accaaaatca acgggacttt ccaaaatgtc      2040
gtaacaactc cgccccattg acgcaaatgg gcggtaggcg tgtacggtgg aggtctata      2100 taagcagagc tcgtttagtg aaccgtcaga tcgcctggag acgccatcca cgctgttttg     2160
acctccatag aagacaccgg gaccgatcca gcctccgcgg ccgggaacgg tgcattggaa     2220
cgctgcagga attgatccgc ggccgcaccg gtaggcctcg tacgcttaat taacggatcc     2280
gcctccacca agggcccatc ggtcttcccc ctggcaccct cctccaagag cacctctggg     2340
ggcacagcgg ccctgggctg cctggtcaag gactacttcc ccgaaccggt gacggtgtcg     2400
tggaactcag gcgccctgac cagcggcgtg cacaccttcc cggctgtcct acagtcctca     2460
```

```
ggactctact ccctcagcag cgtggtgacc gtgccctcca gcagcttggg cacccagacc   2520
tacatctgca acgtgaatca caagcccagc aacaccaagg tggacaagaa agttgagccc   2580
aaatcttgtg acaaaactca cacatgccca ccgtgcccag cacctgaact cctgggggga   2640
ccgtcagtct tcctcttccc cccaaaaccc aaggacaccc tcatgatctc ccggacccct   2700
gaggtcacat gcgtggtggt ggacgtgagc cacgaagacc ctgaggtcaa gttcaactgg   2760
tacgtggacg gcgtggaggt gcataatgcc aagacaaagc cgcgggagga gcagtacaac   2820
agcacgtacc gtgtggtcag cgtcctcacc gtcctgcacc aggactggct gaatggcaag   2880
gagtacaagt gcaaggtctc caacaaagcc ctcccagccc ccatcgagaa aaccatctcc   2940
aaagccaaag gcagccccg agaaccacag gtgtacaccc tgcccccatc ccgggatgag   3000
ctgaccaaga accaggtcag cctgacctgc ctggtcaaag gcttctatcc cagcgacatc   3060
gccgtggagt gggagagcaa tgggcagccg gagaacaact acaagaccac gcctcccgtg   3120
ctggactccg acggctcctt cttcctctac agcaagctca ccgtggacaa gagcaggtgg   3180
cagcagggga acgtcttctc atgctccgtg atgcatgagg ctctgcacaa ccactacacg   3240
cagaagagcc tctccctgtc tccgggtaaa tgagatccgg aattccgccc ctctccctcc   3300 cccccccta acgttactgg ccgaagccgc ttggaataag gccggtgtgc gtttgtctat   3360
atgttatttt ccaccatatt gccgtctttt ggcaatgtga gggcccggaa acctggccct   3420
gtcttcttga cgagcattcc tagggtctt tcccctctcg ccaaaggaat gcaaggtctg   3480
ttgaatgtcg tgaaggaagc agttcctctg gaagcttctt gaagacaaac aacgtctgta   3540
gcgacccttt gcaggcagcg gaaccccca cctggcgaca ggtgcctctg cggccaaaag   3600
ccacgtgtat aagatacacc tgcaaaggcg gcacaacccc agtgccacgt tgtgagttgg   3660
atagttgtgg aaagagtcaa atggctctcc tcaagcgtag tcaacaaggg gctgaaggat   3720
gcccagaagg tacccattg tatgggaatc tgatctgggg cctcggtgca catgctttac   3780
atgtgtttag tcgaggttaa aaaacgtcta ggccccccga accacgggga cgtggttttc   3840
ctttgaaaaa cacgatgata agcttgccac aacccgtacc aaagatggat agatccggaa   3900
agcctgaact caccgcgacg tctgtcgaga agtttctgat cgaaaagttc gacagcgtct   3960
ccgacctgat gcagctctcg gagggcgaag aatctcgtgc tttcagcttc gatgtaggag   4020
ggcgtggata tgtcctgcgg gtaaatagct gcgccgatgg tttctacaaa gatcgttatg   4080
tttatcggca ctttgcatcg gccgcgctcc cgattccgga agtgcttgac attggggaat   4140
tcagcgagag cctgacctat tgcatctccc gccgtgcaca gggtgtcacg ttgcaagacc   4200
tgcctgaaac cgaactgccc gctgttctgc agccggtcgc ggaggccatg gatgcgatcg   4260
ctgcggccga tcttagccag acgagcgggt tcggcccatt cggaccgcaa ggaatcggtc   4320
aatacactac atggcgtgat ttcatatgcg cgattgctga tccccatgtg tatcactggc   4380
aaaactgtga tggacgacac cgtcagtgcg tccgtcgcgca ggctctcgat gagctgatgc   4440
tttgggccga ggactgcccc gaagtccggc acctcgtgca cgcggatttc ggctccaaca   4500
atgtcctgac ggacaatggc cgcataacag cggtcattga ctggagcgag gcgatgttcg   4560
gggattccca atacgaggtc gccaacatct tcttctggag gccgtggttg gcttgtatgg   4620
agcagcagac gcgctacttc gagcggaggc atccggagct tgcaggatcg ccgcggctcc   4680
gggcgtatat gctccgcatt ggtcttgacc aactctatca gagcttggtt gacggcaatt   4740
tcgatgatga gcttgggcg cagggtcgat gcgacgcaat cgtccgatcc ggagccggga   4800
ctgtcgggcg tacacaaatc gcccgcagaa gcgcggccgt ctggaccgat ggctgtgtag   4860
```

-continued

```
aagtactcgc cgatagtgga aaccgacgcc ccagcactcg tccgagggca aaggaataga    4920
gtagatgccg accgaacaag agctgatttc gagaacgcct cagccagcaa ctcgcgcgag    4980
cctagcaagg caaatgcgag agaacggcct tacgcttggt ggcacagttc tcgtccacag    5040
ttcgctaagc tcgctcggct gggtcgcggg agggccggtc gcagtgattc aggcccttct    5100
ggattgtgtt ggtccccagg gcacgattgt catgccacg cactcgggtg atctgactga     5160
tcccgcagat tggagatcgc cgcccgtgcc tgccgattgg gtgcagatct agtcgagggc    5220
tgcagcgctg cagaggccga gtgcagaact gctccaaagg gacctcaagg ctttccgagg    5280
gacactaggc tgactccatc gagccagtgt agagataagc ttatcgatta gtccaatttg    5340
ttaaagacag gatatcagtg gtccaggctc tagttttgac tcaacaatat caccagctga    5400
agcctataga gtacgagcca tagataaaat aaaagatttt atttagtctc cagaaaaagg    5460
ggggaatgaa agaccccacc tgtaggtttg gcaagctagc ttaagtaacg ccattttgca    5520
aggcatggaa aaatacataa ctgagaatag agaagttcag atcaaggtca ggaacagatg    5580
gaacagggtc gaccctagag aaccatcaga tgtttccagg gtgccccaag gacctgaaat    5640
gaccctgtgc cttatttgaa ctaaccaatc agttcgcttc tcgcttctgt tcgcgcgctt    5700
ctgctccccg agctcaataa aagagcccac aaccctcac tcggggcgcc agtcctccga     5760
ttgactgagt cgcccgggta cccgtgtatc caataaaccc tcttgcagtt gcatccgact    5820
tgtggtctcg ctgttccttg ggagggtctc ctctgagtga ttgactaccc gtcagcgggg    5880
gtctttcatt tgggggctcg tccgggatcg ggagacccct gcccagggac caccgaccca    5940
ccaccgggag gtaagctggc tgcctcgcgc gtttcggtga tgacggtgaa acctctgac     6000
acatgcagct cccggagacg gtcacagctt gtctgtaagc ggatgccggg agcagacaag    6060
cccgtcaggg cgcgtcagcg ggtgttggcg ggtgtcgggg cgcagccatg acccagtcac    6120
gtagcgatag cggagtgtag atccggctgt ggaatgtgtg tcagttaggg tgtggaaagt    6180
ccccaggctc cccagcaggc agaagtatgc aaagcatgca tctcaattag tcagcaacca    6240
ggtgtggaaa gtccccaggc tccccagcag gcagaagtat gcaaagcatg catctcaatt    6300
agtcagcaac catagtcccg cccctaactc cgcccatccc gccctaact ccgcccagtt     6360
ccgcccattc tccgccccat ggctgactaa ttttttttat ttatgcagag gccgaggccg    6420
cctcggcctc tgagctattc cagaagtagt gaggaggctt ttttggaggc ctaggctttt    6480
gcaaaaagct tactggctta actatgcggc atcagagcag attgtactga gagtgcacca    6540
tatgcggtgt gaaataccgc acagatgcgt aaggagaaaa taccgcatca ggcgctcttc    6600
cgcttcctcg ctcactgact cgctgcgctc ggtcgttcgg ctgcggcgag cggtatcagc    6660
tcactcaaag gcggtaatac ggttatccac agaatcaggg gataacgcag gaaagaacat    6720
gtgagcaaaa ggccagcaaa aggccaggaa ccgtaaaaag gccgcgttgc tggcgttttt    6780
ccataggctc cgcccccctg acgagcatca caaaaatcga cgctcaagtc agaggtggcg    6840
aaacccgaca ggactataaa gataccaggc gtttccccct ggaagctccc tcgtgcgctc    6900
tcctgttccg accctgccgc ttaccggata cctgtccgcc tttctccctt cgggaagcgt    6960
ggcgctttct catagctcac gctgtaggta tctcagttcg gtgtaggtcg ttcgctccaa    7020
gctgggctgt gtgcacgaac ccccgttca gcccgaccgc tgcgccttat ccggtaacta     7080
tcgtcttgag tccaacccgg taagacacga cttatcgcca ctggcagcag ccactggtaa    7140
caggattagc agagcgaggt atgtaggcgg tgctacagag ttcttgaagt ggtggcctaa    7200
```

-continued

```
ctacggctac actagaagga cagtatttgg tatctgcgct ctgctgaagc cagttacctt    7260
cggaaaaaga gttggtagct cttgatccgg caaacaaacc accgctggta gcggtggttt    7320
ttttgtttgc aagcagcaga ttacgcgcag aaaaaaagga tctcaagaag atcctttgat    7380
cttttctacg gggtctgacg ctcagtggaa cgaaaactca cgttaaggga ttttggtcat    7440
gagattatca aaaaggatct tcacctagat ccttttaaat taaaaatgaa gttttaaatc    7500
aatctaaagt atatatgagt aaacttggtc tgacagttac caatgcttaa tcagtgaggc    7560
acctatctca gcgatctgtc tatttcgttc atccatagtt gcctgactcc ccgtcgtgta    7620
gataactacg atacgggagg gcttaccatc tggccccagt gctgcaatga taccgcgaga    7680
cccacgctca ccggctccag atttatcagc aataaaccag ccagccggaa gggccgagcg    7740
cagaagtggt cctgcaactt tatccgcctc catccagtct attaattgtt gccgggaagc    7800
tagagtaagt agttcgccag ttaatagttt gcgcaacgtt gttgccattg ctgcaggcat    7860
cgtggtgtca cgctcgtcgt ttggtatggc ttcattcagc tccggttccc aacgatcaag    7920
gcgagttaca tgatccccca tgttgtgcaa aaaagcggtt agctccttcg gtcctccgat    7980
cgttgtcaga agtaagttgg ccgcagtgtt atcactcatg gttatggcag cactgcataa    8040
ttctcttact gtcatgccat ccgtaagatg cttttctgtg actggtgagt actcaaccaa    8100
gtcattctga gaatagtgta tgcggcgacc gagttgctct tgcccggcgt caacacggga    8160
taataccgcg ccacatagca gaactttaaa agtgctcatc attggaaaac gttcttcggg    8220
gcgaaaactc tcaaggatct taccgctgtt gagatccagt tcgatgtaac ccactcgtgc    8280
acccaactga tcttcagcat cttttacttt caccagcgtt tctgggtgag caaaaacagg    8340
aaggcaaaat gccgcaaaaa agggaataag ggcgacacgg aaatgttgaa tactcatact    8400 cttcctttttt caatattatt gaagcattta tcagggttat tgtctcatga gcggatacat    8460
atttgaatgt atttagaaaa ataaacaaat aggggttccg cgcacatttc cccgaaaagt    8520
gccacctgac gtctaagaaa ccattattat catgacatta acctataaaa ataggcgtat    8580
cacgaggccc tttcgtcttc aagaattagc ttggccattg catacgttgt atccatatca    8640
taatatgtac atttatattg gctcatgtcc aacattaccg ccatgttgac attgattatt    8700
gactagttat taatagtaat caattacggg gtcattagtt catagcccat atatggagt    8759
```

<210> SEQ ID NO 86
<211> LENGTH: 7501
<212> TYPE: DNA
<213> ORGANISM: Artificial
<220> FEATURE:
<223> OTHER INFORMATION: An artificially synthesized expression cassette
      sequence

<400> SEQUENCE: 86

```
tccgcgttac ataacttacg gtaaatggcc cgcctggctg accgcccaac gacccccgcc     60
cattgacgtc aataatgacg tatgttccca tagtaacgcc aatagggact ttccattgac    120
gtcaatgggt ggagtattta cggtaaactg cccacttggc agtacatcaa gtgtatcata    180
tgccaagtac gccccctatt gacgtcaatg acggtaaatg gcccgcctgg cattatgccc    240
agtacatgac cttatgggac tttcctactt ggcagtacat ctacgtatta gtcatcgcta    300
ttaccatggt gatgcggttt tggcagtaca tcaatgggcg tggatagcgg tttgactcac    360
ggggatttcc aagtctccac cccattgacg tcaatgggag tttgttttgg caccaaaatc    420
aacgggactt tccaaaatgt cgtaacaact ccgccccatt gacgcaaatg ggcggtaggc    480
```

```
gtgtacggtg ggaggtctat ataagcagag ctcaataaaa gagcccacaa cccctcactc      540
ggcgcgccag tcttccgata gactgcgtcg cccgggtacc cgtattccca ataaagcctc      600
ttgctgtttg catccgaatc gtggtctcgc tgttccttgg gagggtctcc tctgagtgat      660
tgactaccca cgacggggt ctttcatttg ggggctcgtc cgggatttgg agaccctgc       720 ccagggacca ccgacccacc accgggaggt aagctggcca gcaacttatc tgtgtctgtc      780
cgattgtcta gtgtctatgt ttgatgttat gcgcctgcgt ctgtactagt tagctaacta      840
gctctgtatc tggcggaccc gtggtggaac tgacgagttc tgaacacccg gccgcaaccc      900
tgggagacgt cccagggact tggggggccg ttttgtggc ccgacctgag aagggagtc       960 gatgtggaat ccgaccccgt caggatatgt ggttctggta ggagacgaga acctaaaaca     1020
gttcccgcct ccgtctgaat ttttgctttc ggtttggaac cgaagccgcg cgtcttgtct     1080
gctgcagcgc tgcagcatcg ttctgtgttg tctctgtctg actgtgtttc tgtatttgtc     1140
tgaaaattag ggcagactg ttaccactcc cttaagtttg accttaggtc actggaaaga      1200
tgtcgagcgg atcgctcaca accagtcggt agatgtcaag aagagacgtt gggttacctt     1260
ctgctctgca gaatggccaa cctttaacgt cggatggccg cgagacggca cctttaaccg     1320
agacctcatc acccaggtta agatcaaggt cttttcacct ggcccgcatg gacacccaga     1380
ccaggtcccc tacatcgtga cctgggaagc cttggctttt gacccccctc cctgggtcaa     1440
gccctttgta caccctaagc ctccgcctcc tcttcctcca tccgcccgt ctctccccct      1500 tgaacctcct cgttcgaccc cgcctcgatc ctcccttat ccagccctca ctccttctct      1560
aggcgccgga attgaagatc tgggggatcg atcctctaga gtccgttaca taacttacgg     1620
taaatggccc gcctggctga ccgcccaacg accccgcc attgacgtca ataatgacgt       1680
atgttcccat agtaacgcca atagggactt tccattgacg tcaatgggtg gagtatttac     1740
ggtaaactgc ccacttggca gtacatcaag tgtatcatat gccaagtacg cccctatg      1800 acgtcaatga cggtaaatgg cccgcctggc attatgccca gtacatgacc ttatgggact     1860
ttcctacttg gcagtacatc tacgtattag tcatcgctat taccatggtg atgcggtttt     1920
ggcagtacat caatgggcgt gaatagcggt ttgactcacg gggatttcca agtctccacc     1980
ccattgacgt caatgggagt ttgttttggc accaaaatca acgggacttt ccaaaatgtc     2040
gtaacaactc cgccccattg acgcaaatgg gcggtaggcg tgtacggtgg gaggtctata     2100
taagcagagc tcgtttagtg aaccgtcaga tcgcctggag acgccatcca cgctgttttg     2160
acctccatag aagacaccgg gaccgatcca gcctccgcgg ccgggaacgg tgcattggaa     2220
cgctgcagga attgatccgc ggccgcaccg gtaggcctcg tacgcttaat aacggatcc      2280 gaaatcaaac gaactgtggc tgcaccatct gtcttcatct tcccgccatc tgatgagcag     2340
ttgaaatctg gaactgcctc tgttgtgtgc ctgctgaata acttctatcc cagagaggcc     2400
aaagtacagt ggaaggtgga taacgccctc caatcggta actcccagga gagtgtcaca     2460
gagcaggaca gcaaggacag cacctacagc ctcagcagca ccctgacgct gagcaaagca     2520
gactacgaga aacacaaagt ctacgcctgc gaagtcaccc atcagggcct gagctcgccc     2580
gtcacaaaga gcttcaacag gggagagtgt tagagatccg gaattccgcc cctctccctc     2640 cccccccct aacgttactg gccgaagccg cttggaataa ggccggtgtg cgtttgtcta     2700
tatgttattt tccaccatat tgccgtcttt tggcaatgtg agggcccgga aacctggccc     2760
tgtcttcttg acgagcattc ctaggggtct ttccctctc gccaaaggaa tgcaaggtct     2820
gttgaatgtc gtgaaggaag cagttcctct ggaagcttct tgaagacaaa caacgtctgt     2880
```

```
agcgacccctt tgcaggcagc ggaaccccc  acctggcgac aggtgcctct gcggccaaaa   2940
gccacgtgta taagatacac ctgcaaaggc ggcacaaccc cagtgccacg ttgtgagttg   3000
gatagttgtg gaaagagtca aatggctctc ctcaagcgta ttcaacaagg ggctgaagga   3060
tgcccagaag gtaccccatt gtatgggatc tgatctgggg cctcggtgca catgctttac   3120
atgtgtttag tcgaggttaa aaaacgtcta ggccccccga accacgggga cgtggttttc   3180
ctttgaaaaa cacgatgata agcttgccac aacccacaag gagacgacct tccatgaccg   3240
agtacaagcc cacggtgcgc ctcgccaccc gcgacgacgt cccccgggcc gtacgcaccc   3300
tcgccgccgc gttcgccgac taccccgcca cgcgccacac cgtcgacccg gaccgccaca   3360
tcgagcgggt caccgagctg caagaactct cctcacgcg  cgtcgggctc gacatcggca   3420
aggtgtgggt cgcggacgac ggcgccgcgg tggcggtctg gaccacgccg gagagcgtcg   3480
aagcgggggc ggtgttcgcc gagatcggcc cgcgcatggc cgagttgagc ggttcccggc   3540
tggccgcgca gcaacagatg gaaggcctcc tggcgccgca ccggcccaag gagcccgcgt   3600
ggttcctggc caccgtcggc gtctcgcccg accaccaggg caagggtctg ggcagcgccg   3660
tcgtgctccc cggagtggag gcggccgagc gcgccggggt gcccgccttc ctggagacct   3720
ccgcgccccg caacctcccc ttctacgagc ggctcggctt caccgtcacc gccgacgtcg   3780
agtgcccgaa ggaccgcgcg acctggtgca tgacccgcaa gccggtgcc  tgacgcccgc   3840
cccacgaccc gcagcgcccg accgaaagga gcgcacgacc ccatggctcc gaccgaagcc   3900
gacccgggcg gccccgccga ccccgcaccc gcccccgagg cccaccgact ctagtcgagg   3960
gctgcagcgc tgcagaggcc gagtgcagaa ctgctccaaa gggacctcaa ggctttccga   4020
gggacactag gctgactcca tcgagccagt gtagagataa gcttatcgat tagtccaatt   4080
tgttaaagac aggatatcag tggtccaggc tctagttttg actcaacaat atcaccagct   4140
gaagcctata gagtacgagc catagataaa ataaaagatt ttatttagtc tccagaaaaa   4200
ggggggaatg aaagacccca cctgtaggtt tggcaagcta gcttaagtaa cgccattttg   4260
caaggcatgg aaaatacat  aactgagaat agagaagttc agatcaaggt caggaacaga   4320
tggaacaggg tcgaccctag agaaccatca gatgtttcca gggtgcccca aggacctgaa   4380
atgaccctgt gccttatttg aactaaccaa tcagttcgct tctcgcttct gttcgcgcgc   4440
ttctgctccc cgagctcaat aaaagagccc acaaccctc  actcggggcg ccagtcctcc   4500
gattgactga gtcgcccggg tacccgtgta tccaataaac cctcttgcag ttgcatccga   4560
cttgtggtct cgctgttcct tgggagggtc tcctctgagt gattgactac ccgtcagcgg   4620
gggtctttca tttgggggct cgtccggat  cgggagaccc ctgccaggg  accaccgacc   4680
caccaccggg aggtaagctg gctgcctcgc gcgtttcggt gatgacggtg aaaacctctg   4740
acacatgcag ctcccggaga cggtcacagc ttgtctgtaa gcggatgccg ggagcagaca   4800
agcccgtcag ggcgcgtcag cgggtgttgg cgggtgtcgg ggcgcagcca tgacccagtc   4860
acgtagcgat agcggagtgt agatccggct gtggaatgtg tgtcagttag ggtgtggaaa   4920
gtccccaggc tccccagcag gcagaagtat gcaaagcatg catctcaatt agtcagcaac   4980
caggtgtgga aagtccccag gctccccagc aggcagaagt atgcaaagca tgcatctcaa   5040
ttagtcagca accatagtcc cgcccctaac tccgcccatc ccgcccctaa ctccgcccag   5100
ttccgcccat tctccgcccc atggctgact aatttttttt atttatgcag aggccgaggc   5160
cgcctcggcc tctgagctat tccagaagta gtgaggaggc ttttttggag gcctaggctt   5220
```

```
ttgcaaaaag cttactggct taactatgcg gcatcagagc agattgtact gagagtgcac   5280
catatgcggt gtgaaatacc gcacagatgc gtaaggagaa aataccgcat caggcgctct   5340
tccgcttcct cgctcactga ctcgctgcgc tcggtcgttc ggctgcggcg agcggtatca   5400
gctcactcaa aggcggtaat acggttatcc acagaatcag gggataacgc aggaaagaac   5460
atgtgagcaa aaggccagca aaaggccagg aaccgtaaaa aggccgcgtt gctggcgttt   5520
ttccataggc tccgcccccc tgacgagcat cacaaaaatc gacgctcaag tcagaggtgg   5580
cgaaacccga caggactata aagataccag gcgtttcccc ctggaagctc cctcgtgcgc   5640
tctcctgttc cgaccctgcc gcttaccgga tacctgtccg cctttctccc ttcgggaagc   5700
gtggcgcttt ctcatagctc acgctgtagg tatctcagtt cggtgtaggt cgttcgctcc   5760
aagctgggct gtgtgcacga accccccgtt cagcccgacc gctgcgcctt atccggtaac   5820
tatcgtcttg agtccaaccc ggtaagacac gacttatcgc cactggcagc agccactggt   5880
aacaggatta gcagagcgag gtatgtaggc ggtgctacag agttcttgaa gtggtggcct   5940
aactacggct acactagaag gacagtattt ggtatctgcg ctctgctgaa gccagttacc   6000
ttcggaaaaa gagttggtag ctcttgatcc ggcaaacaaa ccaccgctgg tagcggtggt   6060
ttttttgttt gcaagcagca gattacgcgc agaaaaaaag gatctcaaga agatcctttg   6120
atcttttcta cggggtctga cgctcagtgg aacgaaaact cacgttaagg gattttggtc   6180
atgagattat caaaaaggat cttcacctag atccttttaa attaaaaatg aagttttaaa   6240
tcaatctaaa gtatatatga gtaaacttgg tctgacagtt accaatgctt aatcagtgag   6300
gcacctatct cagcgatctg tctatttcgt tcatccatag ttgcctgact ccccgtcgtg   6360
tagataacta cgatacggga gggcttacca tctggcccca gtgctgcaat gataccgcga   6420
gacccacgct caccggctcc agatttatca gcaataaacc agccagccgg aagggccgag   6480
cgcagaagtg gtcctgcaac tttatccgcc tccatccagt ctattaattg ttgccgggaa   6540
gctagagtaa gtagttcgcc agttaatagt ttgcgcaacg ttgttgccat tgctgcaggc   6600
atcgtggtgt cacgctcgtc gtttggtatg gcttcattca gctccggttc caacgatca   6660 aggcgagtta catgatcccc catgttgtgc aaaaaagcgg ttagctcctt cggtcctccg   6720
atcgttgtca agtaagtt ggccgcagtg ttatcactca tggttatggc agcactgcat   6780
aattctctta ctgtcatgcc atccgtaaga tgcttttctg tgactggtga gtactcaacc   6840
aagtcattct gagaatagtg tatgcggcga ccgagttgct cttgcccggc gtcaacacgg   6900
gataataccg cgccacatag cagaacttta aaagtgctca tcattggaaa acgttcttcg   6960
gggcgaaaac tctcaaggat cttaccgctg ttgagatcca gttcgatgta acccactcgt   7020
gcacccaact gatcttcagc atcttttact ttcaccagcg tttctgggtg agcaaaaaca   7080
ggaaggcaaa atgccgcaaa aaagggaata agggcgacac ggaaatgttg aatactcata   7140
ctcttccttt ttcaatatta ttgaagcatt tatcagggtt attgtctcat gagcggatac   7200
atatttgaat gtatttagaa aaataaacaa ataggggttc cgcgcacatt tccccgaaaa   7260
gtgccacctg acgtctaaga aaccattatt atcatgacat taacctataa aaataggcgt   7320
atcacgaggc cctttcgtct tcaagaatta gcttggccat tgcatacgtt gtatccatat   7380
cataatatgt acatttatat tggctcatgt ccaacattac cgccatgttg acattgatta   7440
ttgactagtt attaatagta atcaattacg ggtcattag ttcatagccc atatatggag   7500
t                                                                    7501
```